(12) United States Patent
Wanker et al.

(10) Patent No.: US 8,710,088 B2
(45) Date of Patent: Apr. 29, 2014

(54) PHARMACEUTICAL AND DIAGNOSTIC COMPOSITIONS FOR USE IN THE TREATMENT AND DIAGNOSIS OF NEURODEGENERATIVE DISEASES OR AMYLOID DISEASES

(75) Inventors: Erich Wanker, Berlin (DE); Sabine Engemann, Berlin (DE); Susanne Rautenberg, Berlin (DE); Annett Boeddrich, Falkensee (DE); Phoebe Markovic, Berlin (DE); Dagmar Ehrnhöfer, Vancouver (CA); Martin Herbst, Berlin (DE); Jacqueline Walther, Teltow (DE)

(73) Assignee: Max-Delbruck-Centrum fur Molekulare Medizin, Berlin (DE)

( * ) Notice: Subject to any disclaimer, the term of this patent is extended or adjusted under 35 U.S.C. 154(b) by 917 days.

(21) Appl. No.: 10/589,276

(22) PCT Filed: Feb. 11, 2005

(86) PCT No.: PCT/EP2005/001389
§ 371 (c)(1), (2), (4) Date: Mar. 10, 2008

(87) PCT Pub. No.: WO2005/077343
PCT Pub. Date: Aug. 25, 2005

(65) Prior Publication Data
US 2009/0117040 A1 May 7, 2009

(30) Foreign Application Priority Data
Feb. 11, 2004 (DE) .......................... 10 2004 007 384

(51) Int. Cl.
*A61K 31/425* (2006.01)
(52) U.S. Cl.
USPC ............ 514/367; 514/326; 514/336; 514/370
(58) Field of Classification Search
USPC ........... 424/729, 1.65; 514/27, 129, 453, 456, 514/643, 252, 253, 292, 367, 370, 268, 293, 514/294, 326, 336
See application file for complete search history.

(56) References Cited

U.S. PATENT DOCUMENTS

| | | | |
|---|---|---|---|
| 3,502,647 A | 3/1970 | Paragamian et al. | 260/209 |
| 3,957,992 A | 5/1976 | Taylor | 424/251 |
| 3,980,782 A | 9/1976 | Paragamian et al. | 424/251 |
| 3,985,880 A | 10/1976 | Paragamian et al. | 424/251 |
| 4,826,860 A * | 5/1989 | Johnson et al. | 514/367 |
| 5,089,497 A * | 2/1992 | Jaen et al. | 514/252.18 |
| 5,696,148 A * | 12/1997 | Lundbech et al. | 514/419 |
| 5,795,903 A * | 8/1998 | Chapelle et al. | 514/367 |
| 2002/0086067 A1 * | 7/2002 | Choi et al. | 424/729 |
| 2002/0151506 A1 * | 10/2002 | Castillo et al. | 514/27 |
| 2005/0209291 A1 * | 9/2005 | Ramnauth et al. | 514/367 |

FOREIGN PATENT DOCUMENTS

| | | |
|---|---|---|
| DE | 243 026 A1 | 2/1987 |
| EP | 0 001 558 A1 | 5/1979 |
| EP | 0 154 190 A1 | 9/1985 |
| WO | 03/015772 A1 | 2/2003 |
| WO | WO-03/013442 * | 2/2003 |
| WO | WO03015772 * | 2/2003 |
| WO | 03/094878 A1 | 11/2003 |

OTHER PUBLICATIONS

Behl, C., et al., Antioxidant Neuroprotection in Alzheimer's Disease as Preventive and Therapeutic Approach, Free Radical Biology & Medicine, 33:182-191 (2002).
Mandel, S., et al., Cell Signaling Pathways in the Neuroprotective Actions of the Green Tea Polyphenol (−)-epigallocatechin-3-gallate: Implications for Neurodegenerative Diseases, Journal of Neurochemistry, 88:1555-1569 (2004).

* cited by examiner

*Primary Examiner* — Michael G Hartley
*Assistant Examiner* — Jagadishwar Samala
(74) *Attorney, Agent, or Firm* — Pillsbury Winthrop Shaw Pittman LLP

(57) ABSTRACT

The present invention relates to pharmaceutical and diagnostic compositions as well as to the use of the active substances contained therein for preparing a pharmaceutical or a diagnostic composition for the treatment or diagnosis of neurodegenerative disorders or amyloid diseases.

13 Claims, 36 Drawing Sheets

Figure 1:
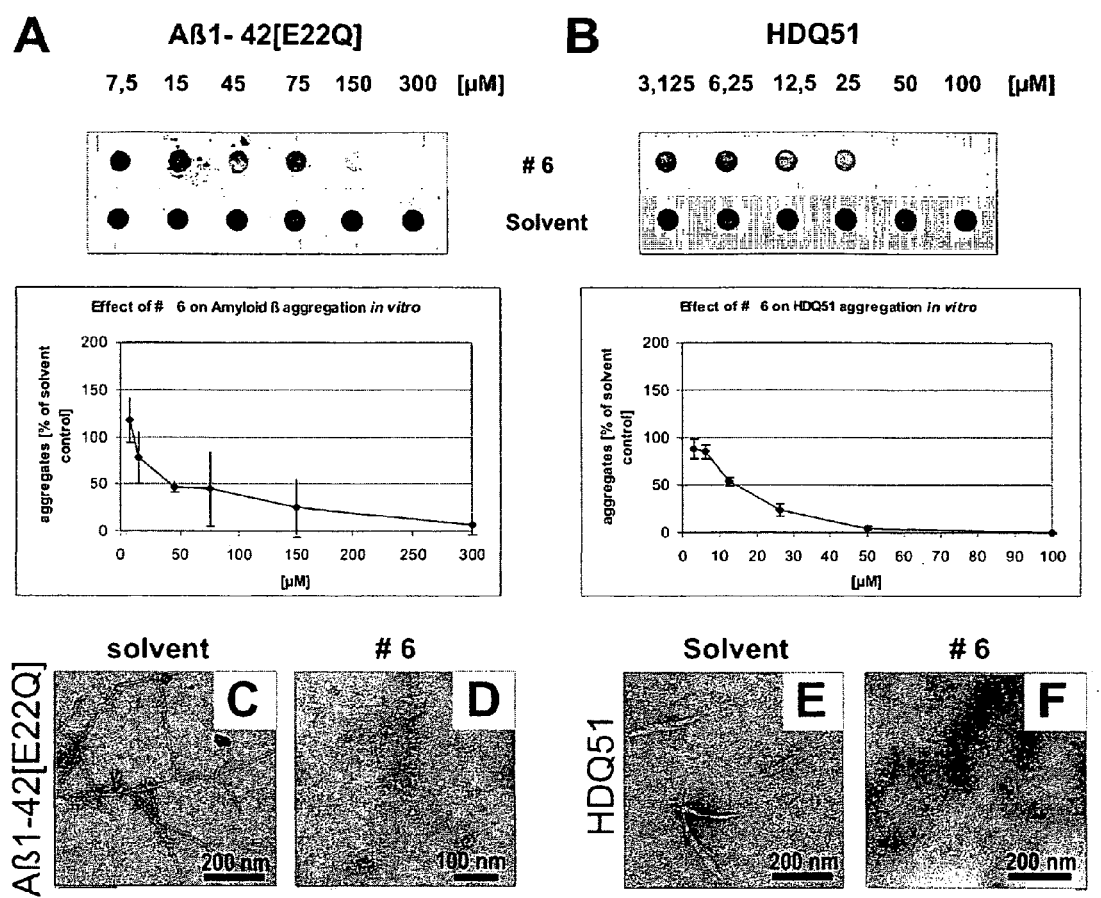

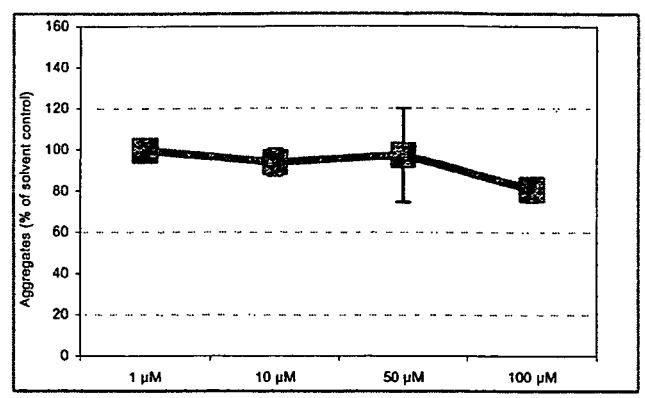
A
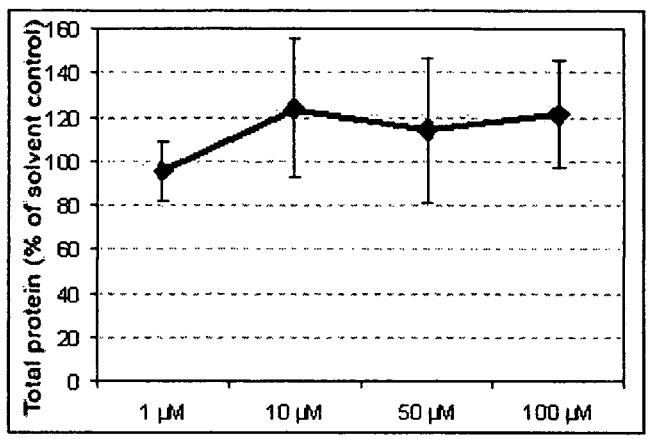
B
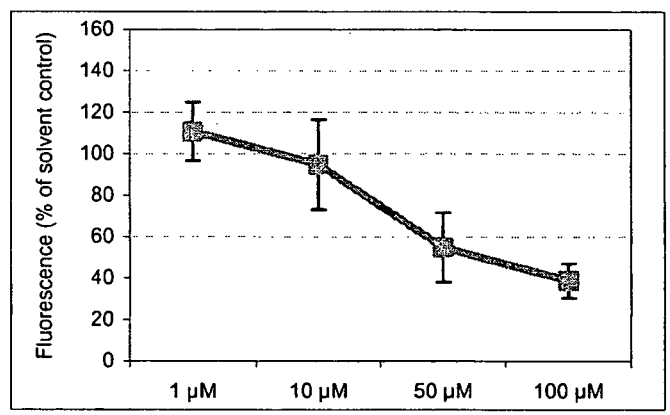
C
Figure 2

S1 = 2-(1H-Imidazole-4-yl)-1H-perimidine
S2 = 1- Ethyl-1H-perimidine
S3 = 2-Pyridine-3-yl-1H-perimidine
S4 = 2-p-Tolyl-1H-perimidine S1 = 1,2-Dimethyl-1H-perimidine
S2 = 4-(1H-Perimidine-2-yl)-benzonitrile
S3 = 1H,3H-Perimidine-2-thione
S4 = 3-(1H-Perimidine-2-yl)-phenylamine Example:
Substance: 3-(1H-Perimidine-2-yl)-phenylamine Substance: (1-Methyl-1H-perimidine-2-yl)-methanol Substance: 2-Pyridine-4-yl-2,3, dihydro-1H-perimidine Aggregates/Protein
(% of solvent
control)

Substance concentration

Blue: Protein concentration in the cell lysate (as a measure of cell growth in the presence of the substance)
Pink: Amount of SDS-insoluble protein aggregates
Substance: 8-Fluoro-1,2-dimethyl-4,5-dihydro-pyrrolo[3,2,1-ij]quinoline-6-one Blue: Protein concentration in the cell lysate (as a measure of cell growth in the presence of the substance)
Pink: Amount of SDS-insoluble protein aggregates
Substance: 8-Fluoro-1,2-dimethyl-4,5-dihydro-pyrrolo[3,2,1-ij]quinoline-6-one Aggregates (% of solvent control)

Example: 2-Furan-2-yl-2,3,4,9-tetrahydro-1H-indenol[2,3-c]pyridine-3-carboxylic acid methyl ester

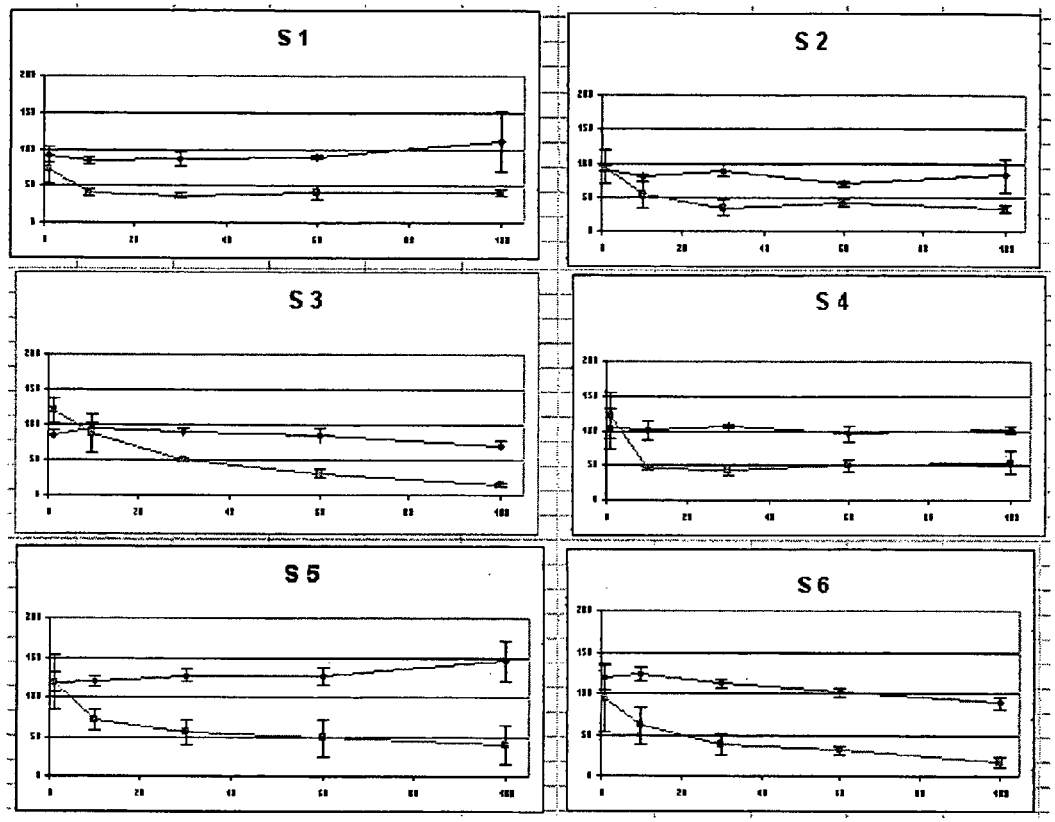

Ordinate: Aggregates/Protein (% of solvent control)
Abscissa: Substance concentration (µM)
Blue: Protein concentration in the cell lysate (as a measure of cell growth in the presence of the substance)
Pink: Amount of SDS-insoluble protein aggregates Substances:
S1 = 3H-Phenoxazine
S2 = Phenoxazine-3-one
S3 = 7-Amino-1,9-dimethyl-phenoxazine-3-one
S4 = Beta-amino-orcein
S5 = Alpha-amino-orcein
S6 = Alpha-hydroxy-orcein

Figure 11

Substance: 1,9-Dimethyl-phenoxazine-3-one

Substance: 7-Hydroxy-1,9-dimethyl-phenoxazine-3-one

Substance: Alpha-amino-orcein

Substance: Beta-hydroxy-orcein

| Substance concentration/µM | 6.25 | 205 | 100 |

+ Amyloid-ß

− Amyloid-ß

Example: Alpha-amino-orcein

Example: Alpha-amino-orcein

Substance: Dihydroxyanthraquinone (Danthron)

Aggregates
(% of solvent
control)

Substance: Chrysarobin

Ordinate: Aggregates/Protein
(% of solvent
control)

Substance concentration

Blue Protein concentration in the cell lysate (as a measure of cell growth in the presence of the substance)
Pink: Amount of SDS-insoluble protein aggregates
Substance: Thiophene-2-yl-acetic acid 4-(4-acetyl-piperazine-1-yl)-phenyl ester Substance: Thiophene-2-yl-acetic acid 4-(4-acetyl-piperazine-1-yl)-phenyl ester Aggregates/Protein
(% of solvent
control)

Substance concentration (µM)

Substance: 5-[4-(Thiazole-2-ylcarbamoyl)-phenyl]-furan-2-carboxylic acid thiazole-2-ylamide Aggregates/Protein
(% of solvent
control)

Substance concentration (μM)

Blue: Protein concentration in the cell lysate (as a measure of cell growth in the presence of the substance)
Pink: Amount of SDS-insoluble protein aggregates
Substance: 4-Methyl-2-[3-(3-phenyl-[1,2,4]thiadiazole-5-yl)-ureido]-pentanoic acid ethyl ester Substance: 4-Methyl-2-(3-phenyl-[1,2,4]thiadiazole-5-yl)-pentanoic acid ethyl ester Substance abbreviations:
EGCG: Epigallocatechin gallate
GCG: Gallocatechin gallate
GC: Gallocatechin
EGC: Epigallocatechin Substance abbreviations:
EGCG: Epigallocatechin gallate
GCG: Gallocatechin gallate
GC: Gallocatechin
EGC: Epigallocatechin Blue: Protein concentration in the cell lysate (as a measure of cell growth in the presence of the substance)
Pink: Amount of SDS-insoluble protein aggregates
S1     = 2-Amino-7-oxo-6,7-dihydro-thiazolo[4,5-f]quinoline-8-carbonitrile Blue: Protein concentration in the cell lysate (as a measure of cell growth in the presence of the substance)
Pink: Amount of SDS-insoluble protein aggregates
S2 = 2-(3-Dimethylamino-propylamino)-7-oxo-6,7-dihydro-thiazolo[4,5-f]quinoline-8-carbonitrile Blue: Protein concentration in the cell lysate (as a measure of cell growth in the presence of the substance)
Pink: Amount of SDS-insoluble protein aggregates
S3 = N-(8-Cyano-7-oxo-6,7-dihydro-thiazolo[4,5-f]quinoline-2-yl)-N-(3-dimethylamino-propyl)-formamide Blue: Protein concentration in the cell lysate (as a measure of cell growth in the presence of the substance)
Pink: Amount of SDS-insoluble protein aggregates
S4 = N-(8-Cyano-7-oxo-6,7-dihydro-thiazolo[4,5-f]quinoline-2-yl)-acetamide Blue: Protein concentration in the cell lysate (as a measure of cell growth in the presence of the substance)
Pink: Amount of SDS-insoluble protein aggregates
S5     = N-(8-Cyano-7-oxo-6,7-dihydro-thiazolo[4,5-f]quinoline-2-yl)-N-(2-dimethylamino-ethyl)-formamide Blue: Protein concentration in the cell lysate (as a measure of cell growth in the presence of the substance)
Pink: Amount of SDS-insoluble protein aggregates
S6 = N-(8-Cyano-7-oxo-6,7-dihydro-thiazolo[4,5-f]quinoline-2-yl)-N-(2-dimethylamino-ethyl)-acetamide Blue: Protein concentration in the cell lysate (as a measure of cell growth in the presence of the substance)
Pink: Amount of SDS-insoluble protein aggregates
S7 = 7-Oxo-2-(2-piperidine-1-yl-ethylamino)-6,7-dihydro-thiazolo[4,5-f]quinoline-8-carbonitrile Blue: Protein concentration in the cell lysate (as a measure of cell growth in the presence of the substance)
Pink: Amount of SDS-insoluble protein aggregates
S8 = 2-[4-(3-Hydroxy-propyl)-piperazine-1-yl]-7-oxo-6,7-dihydro-thiazolo[4,5-f]quinoline-8-carbonitrile Blue: Protein concentration in the cell lysate (as a measure of cell growth in the presence of the substance)
Pink: Amount of SDS-insoluble protein aggregates
S9 = 2-[Benzyl-(2-dimethylamino-ethyl)-amino]-7-oxo-6,7-dihydro-thiazolo[4,5-f]quinoline-8-carbonitrile Blue: Protein concentration in the cell lysate (as a measure of cell growth in the presence of the substance)
Pink: Amount of SDS-insoluble protein aggregates
S10 = 2-{(2-Diethylamino-ethyl)-ethyl-amino]-7-oxo-6,7-dihydro-thiazolo[4,5-f]quinoline-8-carbonitrile

PHARMACEUTICAL AND DIAGNOSTIC COMPOSITIONS FOR USE IN THE TREATMENT AND DIAGNOSIS OF NEURODEGENERATIVE DISEASES OR AMYLOID DISEASES

The present invention relates to pharmaceutical and diagnostic compositions as well as to the use of the active substances contained therein for producing a pharmaceutical or a diagnostic composition for the treatment or diagnosis of neurodegenerative disorders or amyloid diseases.

Various documents are cited in the text of the present description. The disclosure content of the cited documents (including all manufacturer descriptions, information etc.) is herewith incorporated by reference into the present description.

In the prior art, small chemical compounds were identified which can inhibit the aggregation of polyglutamine-containing proteins or amyloid-forming proteins. Patent applications directed to these compounds were filed (Wanker, E. E., Heiser, V., Lehrach, H., Broeker, W., Dunkel, I., Böttcher, H., Barnickel, G., Herhaus, C. (2001) "Inhibitors of PolyQ-Aggregation" EP 01105088.7 and Wanker, E. E., Sittler, A. and Hartl, U. (2001) "Novel compounds useful in the prevention or treatment of diseases associated with protein aggregation and amyloid formation" EP 0110769.5). Excerpts of these inventions and other relevant results were published (Heiser, V., Scherzinger, E., Boeddrich, A., Nordhoff, E., Lurz, R., Schugardt, N., Lehrach, H. and Wanker, E. E. (2000) *Proc Natl Acad Sci USA.* 97, 6739-6744; Heiser, V., Engemann, S., Brocker, W., Dunkel, I., Boeddrich, A., Waelter, S., Nordhoff, E., Lurz, R., Schugardt, N., Rautenberg, S. et al., (2002) *Proc Natl Acad Sci USA,* 99 Suppl 4, 16400-16406 and Sittler, A., Lurz, R., Lueder, G., Priller, J., Hayer-Hartl, M. K., Hartl, F. U., Lehrach, H. and Wanker, E. E. (2001), *Hum Mol* Genet, 10, 1307-1315).

Other working groups as well described positive effects of chemical compounds on the aggregate formation in Huntington's chorea (Ferrante, R. J., Andreassen, O. A., Dedeoglu, A., Ferrante, K. L., Jenkins, B. G., Hersch, S. M. and Beal, M. F. (2002) *J. Neuroscience* 22, 1592-1599, Dedeoglu, A. et al. (2002), *J. Neuroscience* 22, 8942-8950 and Keene, C. D., Rodrigues, C. M. P., Eich, T., Chhabra, M. S., Steer, C. J. and Low, W. C. (2002) *Proc. Natl. Acad. Sci. USA* 99, 10671-10676).

Furthermore, several small molecules were described which inhibit the aggregation of the amyloid β-peptide relevant for Alzheimer's disease. This includes the following publications: Lashuel, H., Hartley, D. M., Balakhaneh, D., Aggarwal, A., Teichberg, S. and Callaway, D. J. E. (2002), *J. Biol. Chem.* 277, 42881-42890; Merlini, G., Ascari, E., Amboldi, N., Bellotti, V., Arbustini, E., Perfetti, V., Ferrari, M., Zorzoli, I., Marione, M. G., Garini, P. et al. (1995), *Proc. Natl. Acad. Sci. USA* 92, 2959-2963; Salomon, A. R., Marcinowski, K. J., Friedland, R. F. and Zagorski, M. G. (1996) *Biochemistry* 35, 13568-13578; Lorenzo, A. and Yankner, B. A. (1994), *Proc. Natl. Acad. Sci. USA* 91, 12243-12247; Tomiyama, T., Shoji, A., Kataoka, K., Suwa, Y., Asano, S., Kaneko, H., Endo, N. (1996), *J. Biol. Chem.* 271, 6839-6844; Howlett, D. R., Perry, A. E., Godfrey, F., Swatton, J. E., Jennings, K. H., Spitzfaden, C., Wadsworth, H., Wood, S. J. and Markwell, R. E. (1999) *Biochem. J.* 340, 283-289; Luo, Y. et al. (2002), *Proc. Natl. Acad. Sci. USA* 99, 12197-12202; J., E. and Lee, M. (2003) *Biochem. Biophys. Res. Comm.* 303, 576-579 and the publication by Howlett, D. R., George, A. R., Owen, D. E., Ward, R. V. and Markwell, R. E. (1999) *Biochem. J.* 343, 419-423. These and other relevant results include the three U.S. Pat. Nos. 6,001,331; 5,972,956 and 5,955,472, the patents WO 9628471, WO 9832754-A, JP 090954222, EP 1018511 and the patent SKF-74652.

Other approaches to the treatment of Alzheimer's disease include preventing the formation of pathological amyloid β-aggregates by using peptides (in this connection, cf. Soto C. (1999), *Rev. Mol. Med.* 5; 343-350).

For the treatment of spinocerebellar ataxia (type 3) the use of small molecules was described by Shirasaki H, Ishida C, Nakajima T, Kamei H, Koide T, Fukuhara N. (2003) [A quantitative evaluation of spinocerebellar degeneration by an acoustic analysis—the effect of taltirelin hydrate on patients with Machado-Joseph disease] Rinsho Shinkeigaku 43, 143-148 and Sakai, T. (1996) [A possibility of therapeutic trial with tetrahydrobiopterin, which was suggested by the administration of sulfamethoxazole-trimethoprim] Rinsho Shinkeigaku 12, 1324-1325.

Furthermore, additional patents and scientific publications are relevant with respect to the catechins of green tea. For instance, several patents have been granted or applied for which are directed to the ingredients of green tea. The U.S. patent 20020151506 ("Catechins for the treatment of fibrillogenesis in Alzheimer's disease, Parkinson's disease, systemic AA amyloidosis and other amyloid disorders"), U.S. patent 20020086067 ("Catechins and green tea extract for the treatment of amyloidosis in Alzheimer's disease and other amyloidoses") are especially relevant. An examination of the delivery of the catechins of green tea to the brain was described by Yoshida, H. et al. (1999) *Biochemical Pharmacology,* 58, 1695-1703. Levites et al. described a neuroprotective effect of EGCG on neuroblastoma cells that had been damaged with the Alzheimer peptide amyloid β-peptide (Levites, Y., Amit, T., Mandel, S. and Youdim, M. B. H. (2003) *FASEB J.* 17, 952-954). The application of the catechins of green tea was not explicitly described and protected for polyglutamine disorders. However, we were able to observe a visible effect in disease models of polyglutamine disorders and would therefore like to seek protection for the application specifically for this group of disorders.

Many of the known compounds are not aimed at a direct interaction with the aggregate-forming proteins but to an indirect interaction, e.g. via heat shock proteins (HSPs). However, it is more useful to influence the formation of aggregates directly since according to current knowledge, they play an essential role in the development of the disease in the case of most disorders. Furthermore, an approach with chemical agents is superior to one with peptides since the latter are generally not delivered to the brain in an efficient manner and, most of the time, also decompose very quickly.

To sum up, it has to be noted that to this date disorders wherein the pathological deposit of proteins is part of the essential disease mechanisms can to a large extent only be treated symptomatically. There is therefore a demand for additional or more effective treatment options for these disorders.

It was therefore the object of the present invention to provide means and methods for the treatment and diagnosis of neurodegenerative disorders and amyloid diseases.

This object is achieved by the provision of the embodiments characterized in the claims.

Consequently, the present invention relates to a pharmaceutical or diagnostic composition comprising one or more active substances wherein the one or more active substance(s) is/are selected from a group consisting of:

(a) active substances with a structure according to formula I-1 to I-9

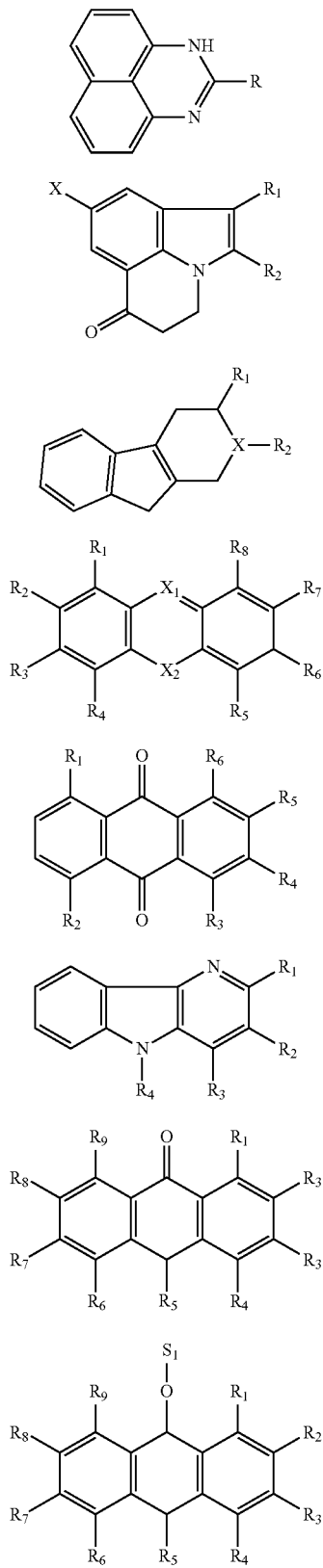

Formula I-1

Formula I-2

Formula I-3

Formula I-4

Formula I-5

Formula I-6

Formula I-7

Formula I-8

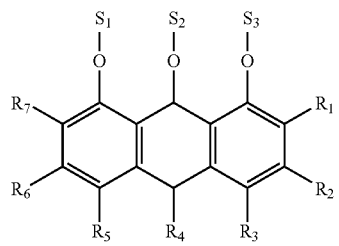

Formula I-9 wherein X in formulas I-2 and I-3 is H, OH, $NH_2$ or a halogen atom and $X_1$ and $X_2$ in formula I-4 are any heteroatom;

(b) active substances with a structure according to formula II-1 or II-2

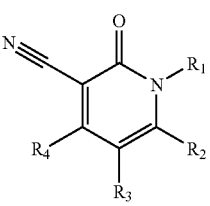

Formula II-1

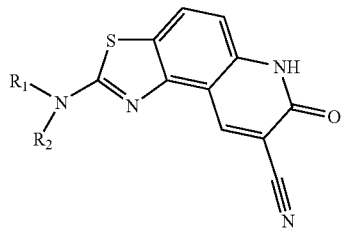

Formula II-2

(c) active substances with a structure according to formula III-1 to III-6

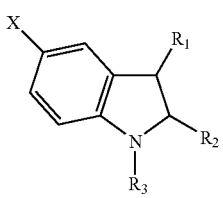

Formula III-1

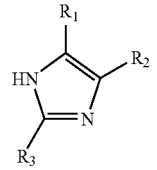

Formula III-2

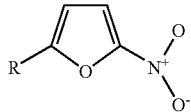

Formula III-3

Formula III-4

Formula III-5

Formula III-6 wherein X in formula III-1 and $X_1$ and $X_2$ in formula III-5 are H, OH, $NH_2$ or a halogen atom;

(d) active substances with a structure according to formula IV-1 to IV-6

Formula IV-1

Formula IV-2

Formula IV-3

Formula IV-4

Formula IV-5

Formula IV-6

$X_1$ and $X_2$ in formula IV-6 are selected from H, F, I, Br or Cl, OH or OA, SH or SA, $NH_2$, $NHA_1$ or $NA_1A_2$ or A and wherein A and/or $A_1$ and $A_2$ is/are a branched, straight-chain or cyclic alkyl or heteroalkyl group with up to 7 carbon atoms;

(e) active substances with a structure according to formula V-1 to V-4

Formula V-1

Formula V-2

-continued

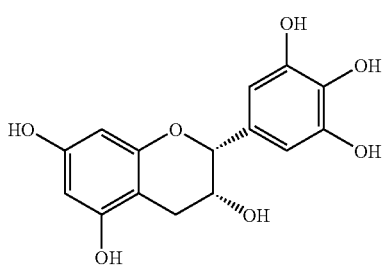

Formula V-3

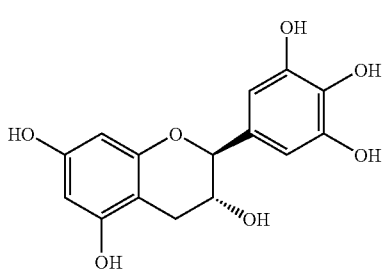

Formula V-4

(f) active substances with a structure according to formula VI-1 or VI-2

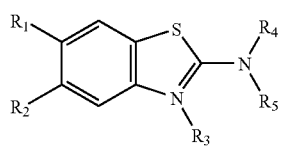

Formula VI-1

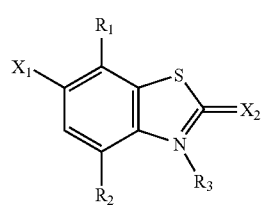

Formula VI-2 wherein $R_1$ to $R_9$ and $S_1$ to $S_3$ are selected from
(i) H, OH, $NH_2$ or a halogen atom;
(ii) single- or multi-branched or straight-chain alkyl or heteroalkyl groups with one or two rings and up to 10 carbon atoms;
(iii) cyclic alkyl or heteroalkyl groups with 1 or 2 rings or aryl or heteroaryl groups with up to 10 carbon atoms each.

The mentioned single- or multi-branched or straight-chain alkyl or heteroalkyl groups comprise 1, 2, 3, 4, 5, 6, 7, 8, 9 or 10 carbon atoms. The ring or ring systems possible in groups $R_1$ to $R_9$ and $S_1$ to $S_3$ in turn comprise 1, 2, 3, 4, 5, 6, 7, 8, 9 or 10 carbon atoms so that the mentioned groups can comprise a total of up to 20 carbon atoms, whereby any number lower than 20 is specifically envisaged as well. However, it is especially preferred that the number of carbon atoms in groups $R_1$ to $R_9$ and $S_1$ to $S_3$ does not exceed a total of 10. Again, any number lower than 10 is specifically envisaged as well.

The person skilled in the art is familiar with the term "heteroatom". In this context, the term particularly refers to, but is not limited to, N, O, Cl, F, Br, I and S. It is preferred that the heteroatoms be present in the form of amides, esters, nitrites and ether compounds.

All the active substances or chemical agents inhibit the aggregation of proteins relevant to a disease which in the case of certain diseases, also known in the prior art as "amyloid diseases", are deposited in the form of amyloids. These diseases include in particular neurodegenerative disorders.

The active substances or chemical agents are suitable for both the diagnosis and the treatment of these disorders. Within the framework of the present invention, the term "active substance" is also used in connection with diagnostic compositions. This is because binding of the active substance to amyloids or aggregates has to occur to allow a positive diagnosis of an amyloid or aggregate formation. This binding is subsumed under the term "effect". In other words, the term "effect" is not restricted to a therapeutic effect.

The conversion of the protein-containing deposits to a form that can be broken down more easily by the organism by means of small molecules or the prevention of the formation of protein aggregates are possibilities of preventing these disorders, slowing their progress or even leading to an improvement and the disappearance of the symptoms. The active substances or chemical agents we identified have the potential of affecting the protein aggregation accordingly. They are not only useful for a therapeutic application or the development thereof but they can also potentially be used for the diagnosis or the evaluation of the progress of diseases based on the pathological deposit of proteins.

The invention offers several advantages compared to known pharmaceutical compositions and methods of treatment:

An essential characteristic of the pathogenesis mechanism of different neurodegenerative diseases—especially Alzheimer's disease, Parkinson's disease and polyglutamine disorders such as Huntington's chorea—is the insolubilization and the deposit of aggregates of disease-specific proteins: In the case of Alzheimer's disease, it is amyloid-beta, in the case of Parkinson's disease, alpha-synuclein, in the case of polyglutamine disorders, huntingtin or ataxins. The substances presented by us are highly suitable for the treatment of these disorders because they attack at a presumably very early stage of the disease mechanism, namely the deposit of aggregated proteins, and therefore could represent a causal treatment to a much higher degree than previous forms of therapy.

The chemical agents of the present invention are characterized in that due to their size, structure and distribution coefficient in an octanol/water mixture, they can potentially be delivered to the brain and are therefore suitable for treating disorders of the central nervous system.

Another advantage is the fact that the substances are relatively easy to synthesize. In the case of catechin derivatives, which are ingredients of green tea, they are even easily accessible natural products.

The selected substances are stable for an extended period of time.

A particular advantage lies in the fact that we have been able to prove for a number of these chemical agents that they are not only able to inhibit the aggregation of an individual protein but even the aggregation of different proteins such as huntingtin, ataxin-3 or amyloid-beta. These compounds can therefore potentially be useful in the treatment of not only one but several diseases.

The substances have already been tested for toxicity in different cell culture models and toxic substances have been eliminated.

The ingredients of green tea—catechin derivatives—have been proven to be well tolerated and have already been administered to patients in several clinical studies— however, in the course of treatments of cancerous diseases—and the lack of toxic effects has been demonstrated.

Since there are indications that at least a part of the substances binds directly to protein aggregates (especially of huntingtin and ataxin-3) there is the possibility of using these compounds in diagnostics as well. For this purpose, the molecules could be labeled—e.g. radioactively—and an accumulation in brain tissue could for example be detected by means of PET (positron emission tomography) technology. This way, a use in diagnostics (especially significant in the case of Alzheimer's disease and Parkinson's disease) and as surrogate markers in the observation of the course of an illness, for example in clinical studies of polyglutamine disorders (Huntington's chorea), would be possible.

The active substances contained in the pharmaceutical and diagnostic compositions according to the present invention can be used as such or after their pharmacological properties have been improved.

Accordingly, the present invention also encompasses pharmaceutical and diagnostic compositions whose above-mentioned active substances have been subjected to an improvement of their pharmacological properties. For this purpose, the molecular scaffold of the active substance is modified further in order to obtain a modified binding site, a modified activity spectrum, a modified organ specificity, an improved activity, a reduced toxicity (an improved therapeutic index), reduced side-effects, a delayed onset of the therapeutic effectiveness or the duration of the therapeutic effectiveness, modified pharmacokinetic parameters (resorption, distribution, metabolism or excretion), modified physicochemical parameters (solubility, hygroscopic properties, color, taste, smell, stability, state of matter), an improved general specificity, organ or tissue specificity, and/or an optimized form and route of administration. This can be achieved by the esterification of carboxy groups, hydroxy groups with carboxylic acids, hydroxy groups to e.g. phosphates, pyrophosphates, sulfates, "hemisuccinates" or the formation of pharmaceutically acceptable salts, pharmaceutically acceptable complexes or the synthesis of pharmacologically active polymers, or the introduction of hydrophilic groups, the introduction and/or the replacement of substituents in aromatics or side chains, the alteration of the substituent pattern or the modification by introducing isosteric or bioisosteric groups, or the synthesis of homologous compounds, and/or the introduction of branched side chains, the conversion of alkyl substituents to cyclic analogues, the derivatization of hydroxy groups to ketals or acetals, the N-acetylation to amides, phenyl carbamates, the synthesis of Mannich bases and/or imines, or the conversion of ketones, aldehydes in Schiff bases, oximes, acetals, ketals, enol esters, oxazolidines, thiazolidines or combinations thereof.

The different measures described above are generally known. They include or are based on quantitative analyses of structure-activity relationships (QSAR); cf. Kubinyi, "Hausch-Analysis and Related Approaches", Publishing House VCH, Weinheim 1992, as well as combinatory (bio)chemistry, classical chemistry and other approaches; cf. e.g. Holzgrabe and Bechtold, *Deutsche Apotheker Zeitung* 140(8) (2000), 813-823.

In a preferred embodiment of the pharmaceutical or diagnostic composition, the halogen atoms are selected from a group consisting of I, Cl, Br or F. F is particularly preferred.

In a preferred embodiment of the pharmaceutical or diagnostic composition, the alkyl, heteroalkyl, aryl or heteroaryl groups comprise 1, 2, 3 or 4 heteroatoms each.

In a preferred embodiment of the pharmaceutical or diagnostic composition, the heteroatoms are selected from a group consisting of N, O, or S.

In a preferred embodiment of the pharmaceutical or diagnostic composition, the alkyl, heteroalkyl, aryl or heteroaryl groups comprise 1, 2, 3 or 4 substituents each.

In an especially preferred embodiment of the pharmaceutical or diagnostic composition, the substituents are selected from a group consisting of Cl, F, Br or I.

In a preferred embodiment of the pharmaceutical or diagnostic composition, $R_1$ and $R_2$, $R_2$ and $R_3$, $R_3$ and $R_4$, $R_4$ and $R_5$, $R_5$ and $R_6$, $R_6$ and $R_7$, $R_7$ and $R_8$ and/or $R_8$ and $R_9$ are bridged via further atoms.

In a preferred embodiment of the diagnostic composition, the active substance or at least one of the active substances is labeled. The labeling is preferably a radioactive labeling.

The binding to aggregates or amyloids as well as the binding site in the organism or a sample taken from the organism can be detected by means of imaging processes, in the case of radioactive-labeled active substances for example by means of the PET process (positron emission tomography) mentioned above. The process can be carried out in vitro, ex vivo or in vivo.

The possible nuclides are known to the person skilled in the art. They are usually short-lived nuclides with a preferred half-life between 20 minutes and 2 hours which can be prepared in a cyclotron.

The present invention also relates to the use of one or more of the active substances described above for preparing a pharmaceutical or diagnostic composition for the treatment or diagnosis of neurodegenerative disorders or amyloid diseases.

The terms "amyloid" and "amyloid disease" are known to the person skilled in the art. Amyloid is defined by three classical parameters which are used individually or in combination to detect amyloids and thus the presence of amyloid diseases:

The Congo red binding visible in transmitted light under a microscope and the green birefringence visible in polarized light. The latter indication is only pathognomic if the stringent Congo red staining according to Puchtler et. al. is applied.

The fibrillar nature of the deposited proteins, visible under the electron microscope. The fibrils have a thickness of about 10 nm, appear rigid and are partially branched. All amyloid deposits contain fibrils of a similar type. An assay (filter assay, membrane filter test) for detecting the fibrils is described in the European patent application EP 98943817.1 ("Novel method of detecting amyloid-like fibrils or protein aggregates") and herewith explicitly incorporated by reference. In this connection, reference is also made to the membrane filter tests mentioned in the examples (see also FIG. 1B), optionally using electron microscopy (FIGS. 1E and 1F).

The beta-sheet structure. All amyloid fibril proteins examined so far had a beta-sheet structure. Glenner considers this structure to be the pathogenic principle. Beta-sheet fibrils as formed by the amyloid are insoluble in normal buffers and resist enzymatic degradation. They are not recognized as foreign bodies by the organism. Glenner thus appropriately described amyloidoses as beta-fibrilloses.

Selected indications which fall under the definition "amyloid diseases", and how they are diagnosed for example in clinical medicine, are described in more detail below.

In a preferred embodiment of the pharmaceutical composition, the diagnostic composition or the use, the pharmaceutical or diagnostic composition comprises, in addition to the active substance, one or more pharmaceutically acceptable carriers, diluents or excipients.

Examples of suitable pharmaceutically acceptable carriers and/or diluents are known to the person skilled in the art and include e.g. phosphate-buffered sodium chloride solutions, water, emulsions, such as e.g. oil/water emulsions, different types of wetting agents or detergents, sterile solutions, etc. Pharmaceutical compositions comprising such substrates can be formulated according to known conventional methods. The pharmaceutical compositions can be administered to an individual in a suitable dosage. The administration can be oral or parenteral, e.g. intravenous, intraperitoneal, subcutaneous, intramuscular, local, intranasal, intrabronchial, oral or intradermal, or via a catheter into an artery. Preparations for a parenteral administration include sterile aqueous or non-aqueous solutions, suspensions and emulsions. Examples of non-aqueous solvents are propylene glycol, polyethylene glycol, vegetable oils such as e.g. olive oil, and organic ester compounds such as e.g. ethyl oleate which are suitable for injections. Aqueous substrates include water, hydroalcoholic solutions, emulsions, suspensions, salt solutions and buffered media. Parenteral substrates include sodium chloride solutions, Ringer's dextrose, dextrose and sodium chloride, lactated Ringer's solution and bonded oils. Intravenous substrates include e.g. liquid, nutritive and electrolyte supplements (such as e.g. those based on Ringer's dextrose). The pharmaceutical composition can also comprise preservatives and other additives, such as e.g. antimicrobial compounds, antioxidants, complex formers and inert gases. Furthermore, depending on the intended specific use, other active substances can be present such as e.g. interleukins, growth factors, differentiation factors, interferons, chemotactic proteins or an unspecific immunomodulator.

The type of dosage is determined by the physician in charge in accordance with the clinical factors. The person skilled in the art is aware of the fact that the type of dosage depends on different factors, such as e.g. the body height and weight, the body surface, the age, sex or general health of the patient, but also on the specific preparation to be administered, the duration and manner of administration, and on other drugs which may be administered at the same time. A typical dose can e.g. be in a range of between 0.001 and 1,000 µg, wherein doses below and above this exemplary range are also conceivable, in particular when keeping in mind the above-mentioned factors. In general, when administered regularly, the composition according to the present invention should be administered in doses in a range of between 1 µg and 10 mg units per day. In these preparations, the active substances will usually be present in a concentration of more than 10 µg/ml of a physiological buffer. However, they can also be present in solid form at a concentration of 0.1 to 99.5 wt.-% of the total mixture. Generally it has been shown to be advantageous to administer the active substance(s) in total amounts of about 0.001 to 100 mg/kg, preferably in total amounts of about 0.01 to 10 mg/kg body weight, over 24 hours, optionally as a continuous infusion or in the form of several individual doses to achieve the desired result. If the composition is administered intravenously, the dosage should be in the range of between 1 µg and 10 mg units per kilogram body weight per day. The pharmaceutical composition can be administered topically, locally or systemically.

The present invention also relates to methods for the treatment or diagnosis of neurodegenerative disorders or amyloid diseases comprising administering a pharmaceutical compositions according to the present invention or a diagnostic composition according to the present invention to a subject.

In a preferred embodiment of the method, the subject is a human being.

In a preferred embodiment of the use or the method, the neurodegenerative disorder is selected from a group consisting of Alzheimer's disease, Parkinson's syndrome and polyglutamine diseases.

Here, it is preferred that Parkinson's syndrome encompass idiopathic Parkinson's disease as well as atypical Parkinson's syndromes associated with protein aggregation; and that polyglutamine diseases encompass Huntington's chorea, spinocerebellar ataxias of types 1, 2, 3, 6, 7 and 17, dentatorubral pallidoluysian atrophy as well as spinobulbar muscular atrophy (Kennedy syndrome).

It is furthermore preferred that the amyloid disease be selected from the group consisting of: Hereditary and non-hereditary prion diseases (kuru, fatal familial insomnia, Gerstmann-Straussler-Scheinker syndrome, Creutzfeld-Jacob disease, new variant of Creutzfeld-Jacob disease), dementia with Lewy bodies, primary systemic amyloidosis, secondary systemic amyloidosis with deposits of serum amyloid A, senile systemic amyloidosis, familial amyloid polyneuropathy types I and III, familial nonneuropathic amyloidosis, familial British dementia, hereditary cerebral amyloid angiopathy, hemodialysis-associated amyloidosis, familial amyloidosis-Finnish type, diabetes mellitus type II, hereditary renal amyloidosis, injection amyloidosis with deposits of insulin, medullary carcinoma of the thyroid with deposits of calcitonin, atrial amyloidosis with deposits of ANF, inclusion body myositis.

As has already been explained in the description of the main embodiment, the active substances or chemical agents contained in the pharmaceutical or diagnostic compositions according to the present invention can be divided into 6 groups based on their chemical structure. In the following, these groups will be described in detail.

Group I

This group contains polycyclic compounds whose outstanding characteristic is the presence of at least tricyclic aromatic groups. The aromatic functional groups are either bonded to numerous hydroxy groups or contain oxo groups, or substitutions with oxygen or nitrogen atoms occur in the aromatic rings themselves.

In particular, this includes the derivatives of the following molecular scaffolds:

Molecular Scaffold I-1:

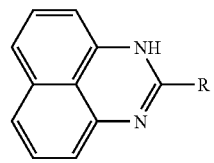

R can be:
H, OH, NH$_2$, Hal
a single- or multi-branched or straight-chain alkyl chain which can comprise 1, 2, 3, 4, 5, 6, 7, 8, 9 or 10 carbon atoms
a cyclic alkyl chain with 1 or 2 rings or an aryl compound with 1 or 2 rings which can comprise 1, 2, 3, 4, 5, 6, 7, 8, 9 or 10 carbon atoms each
the mentioned alkyl or aryl groups can also each comprise 1, 2, 3 or 4 heteroatoms such as N, O, Cl, F, Br, I or S, in particular also in the form of amides, esters, nitrites or ether compounds the cyclic compounds can be connected to the basic structure via alkyl chains which can comprise heteroatoms such as N, O, Cl, F, Br, I or S as described above Hal can represent: I, Cl, Br or F Preferred pharmaceutical or diagnostic compositions according to the present invention comprise an active substance with a structure according to formula I-1, wherein the active substance is selected from:

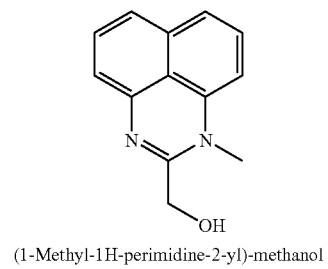

(1-Methyl-1H-perimidine-2-yl)-methanol

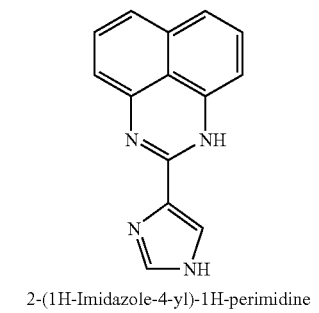

2-(1H-Imidazole-4-yl)-1H-perimidine

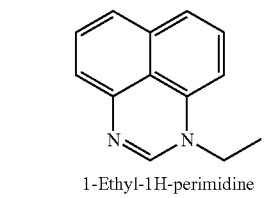

1-Ethyl-1H-perimidine

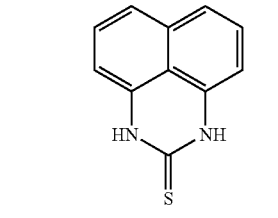

1H,3H-Perimidine-2-thione

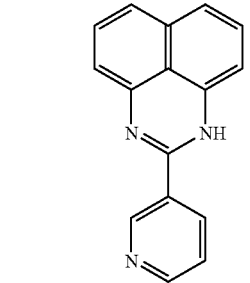

2-Pyridine-3-yl-1H-perimidine

-continued

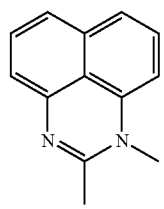

1,2-Dimethyl-1H-perimidine

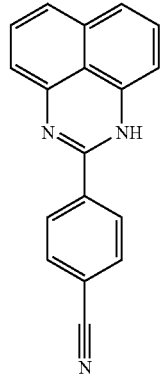

4-(1H-Perimidine-2-yl)-benzonitrile

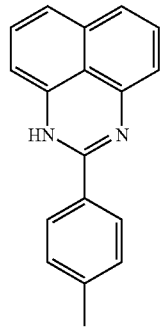

2-p-Tolyl-1H-perimidine

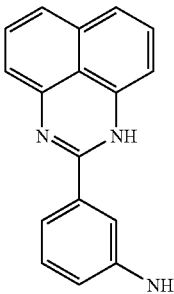

3-(1H-Perimidine-2-yl)-phenylamine

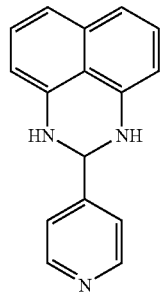

2-Pyridin-4-yl-2,3-dihydro-1H-perimidine

Other pharmaceutical or diagnostic compositions according to the present invention comprise active substances selected from the following derivatives:
2-(1H-Imidazole-4-yl)-1H-perimidine and
2-pyridine-3-yl-1H-perimidine
Molecular Scaffold I-2:

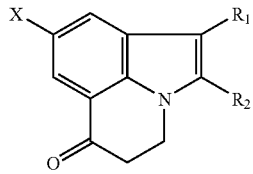

4,5-Dihydro-pyrrolo[3,2,1-ij]quinoline-6-one

X can be:
H, OH, $NH_2$, Hal
$R_1$ to $R_2$ can be:
H, OH, $NH_2$, Hal
single- or multi-branched or straight-chain alkyl chains which can comprise 1, 2, 3, 4, 5, 6, 7, 8, 9 or 10 carbon atoms each
cyclic alkyl chains with 1 or 2 rings or aryl compounds with 1 or 2 rings which can comprise 1, 2, 3, 4, 5, 6, 7, 8, 9 or 10 carbon atoms each
the mentioned alkyl or aryl groups can also each comprise 1, 2, 3 or 4 heteroatoms such as N, O, Cl, F, Br, I or S, in particular also in the form of amides, esters, nitrites or ether compounds
the cyclic compounds can be connected to the basic structure via alkyl chains which can comprise heteroatoms such as N, O, Cl, F, Br, I or S as described above
Hal can represent: I, Cl, Br or F
$R_1$ and $R_2$ can be bridged independently or via further atoms Preferred pharmaceutical or diagnostic compositions according to the present invention comprise an active substance with a structure according to formula I-2, wherein the active substance is

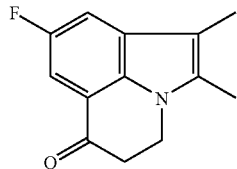

8-fluoro-1,2-dimethyl-4,5-dihydro-pyrrolo[3,2,1-ij]quinoline-6-one.
Molecular Scaffold I-3:

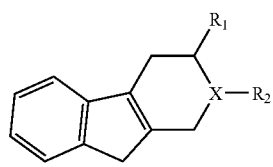

Tetrahydrofluorene
X can be any heteroatom, specifically, N, O, P and S are possible atoms $R_1$ to $R_2$ can be:
H, OH, $NH_2$, Hal
single- or multi-branched or straight-chain alkyl chains which can comprise 1, 2, 3, 4, 5, 6, 7, 8, 9 or 10 carbon atoms each
cyclic alkyl chains with 1 or 2 rings or aryl compounds with 1 or 2 rings which can comprise 1, 2, 3, 4, 5, 6, 7, 8, 9 or 10 carbon atoms each
the mentioned alkyl or aryl groups can also each comprise 1, 2, 3 or 4 heteroatoms such as N, O, Cl, F, Br, I or S, in particular also in the form of amides, esters, nitriles or ether compounds
the cyclic compounds can be connected to the basic structure via alkyl chains which can comprise heteroatoms such as N, O, Cl, F, Br, I or S as described above
Hal can represent: I, Cl, Br or F
$R_1$ to $R_2$ can be bridged independently or via further atoms The following compound shall be mentioned as an example of this subgroup:
2-Furan-2-yl-2,3,4,9-tetrahydro-1H-indenol[2,3-c]pyridine-3-carboxylic acid methyl ester
Molecular Scaffold I-4:

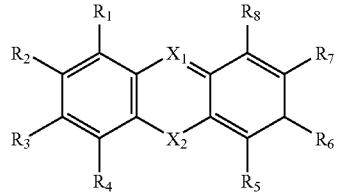

Anthracene
$X_1$ and $X_2$ can be any heteroatom, however, in particular N, O, P and S
$R_1$ to $R_8$ can be:
H, OH, $NH_2$, Hal
single- or multi-branched or straight-chain alkyl chains which can comprise 1, 2, 3, 4, 5, 6, 7, 8, 9 or 10 carbon atoms each
cyclic alkyl chains with 1 or 2 rings or aryl compounds with 1 or 2 rings which can comprise 1, 2, 3, 4, 5, 6, 7, 8, 9 or 10 carbon atoms each
the mentioned alkyl or aryl groups can also each comprise 1, 2, 3 or 4 heteroatoms such as N, O, Cl, F, Br, I or S, in particular also in the form of amides, esters, nitriles or ether compounds
the cyclic compounds can be connected to the basic structure via alkyl chains which can comprise heteroatoms such as N, O, Cl, F, Br, I or S as described above
Hal can represent: I, Cl, Br or F
$R_1$ and $R_2$, $R_2$ and $R_3$, $R_3$ and $R_4$, $R_5$ and $R_6$, $R_6$ and $R_7$, and $R_7$ and $R_8$ can be bridged independently or via further atoms Preferred pharmaceutical or diagnostic compositions according to the present invention comprise an active substance with a structure according to formula I-4, wherein the active substance is:

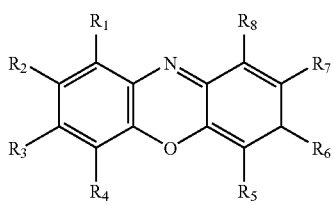

3H-Phenoxazine

Preferred pharmaceutical or diagnostic compositions according to the present invention comprise an active substance with the above structure, wherein the active substance is selected from:

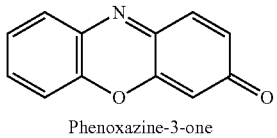

Phenoxazine-3-one

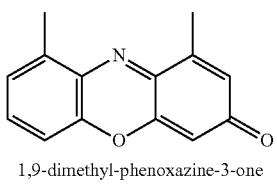

1,9-dimethyl-phenoxazine-3-one

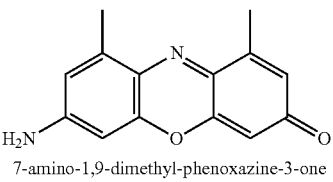

7-amino-1,9-dimethyl-phenoxazine-3-one

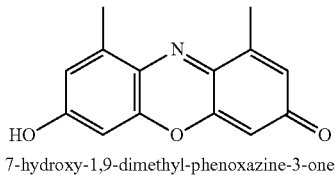

7-hydroxy-1,9-dimethyl-phenoxazine-3-one

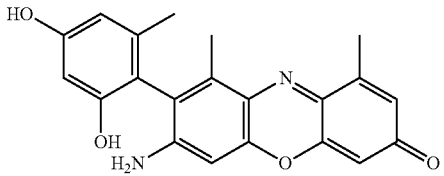

7-amino-8-(2,4-dihydroxy-6-methyl-phenyl)-1,9-dimethyl-phenoxazine-3-one (alpha-amino-orcein)

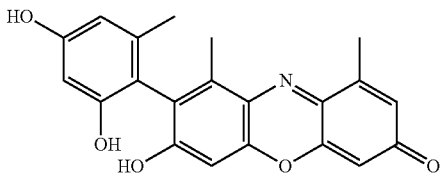

8-(2,4-dihydroxy-6-methyl-phenyl)-7-hydroxy-1,9-dimethyl-phenoxazine-one (alpha-hydroxy-orcein)

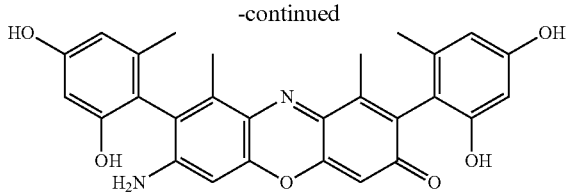

7-amino-2,8-bis-(2,4-dihydroxy-6-methyl-phenyl)-1,9-dimethyl-phenoxazine-3-one (beta-amino-orcein)

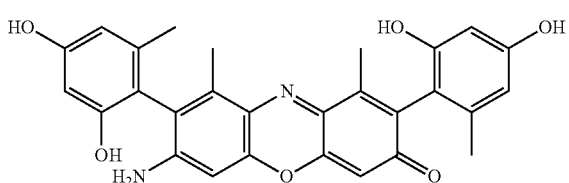

7-amino-2,8-bis-(2,4-dihydroxy-6-methyl-phenyl)-1,9-dimethyl-phenoxazine-3-one (gamma-amino-orcein)

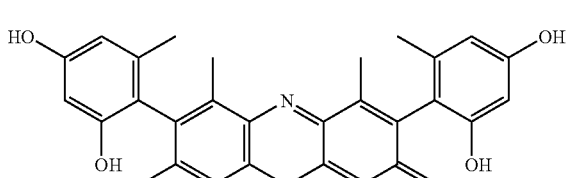

2,8-bis-(2,4-dihydroxy-6-methyl-phenyl)-7-hydroxy-1,9-dimethyl-phenoxazine-3-one (beta-hydroxy-orcein)

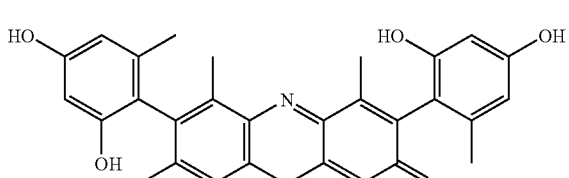

2,8-bis-(2,4-dihydroxy-6-methyl-phenyl)-7-hydroxy-1,9-dimethyl-phenoxazine-3-one (gamma hydroxy-orcein)

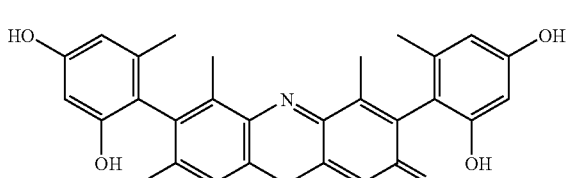

beta-amino-orceimine

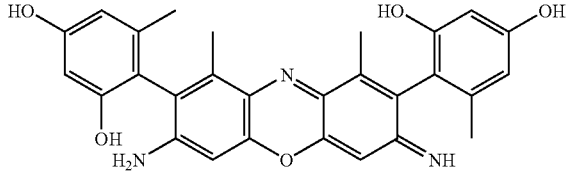

gamma-amino-orceimine

Other pharmaceutical or diagnostic compositions according to the present invention comprise active substances selected from the following derivatives:

7-Amino-8-[2,4-dihydroxy-6-methyl-phenyl)-1,9-dimethyl-phenoxazine-3-one 7-amino-1,8,10a,11-tetrahydroxy-10,12-dioxo-6,6a,7,10,10a,12-hexahydro-5aH-5-thia-naphthacene-9-carboxylic acid amide Molecular Scaffold I-5:

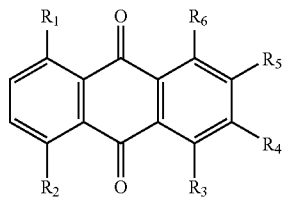

4a,9a-Dihydro-anthraquinone $R_1$ to $R_6$ can be:

H, OH, $NH_2$, Hal

- single- or multi-branched or straight-chain alkyl chains which can comprise 1, 2, 3, 4, 5, 6, 7, 8, 9 or 10 carbon atoms each
- cyclic alkyl chains with 1 or 2 rings or aryl compounds with 1 or 2 rings which can comprise 1, 2, 3, 4, 5, 6, 7, 8, 9 or 10 carbon atoms each
- the mentioned alkyl or aryl groups can also each comprise 1, 2, 3 or 4 heteroatoms such as N, O, Cl, F, Br, I or S, in particular also in the form of amides, esters, nitrites or ether compounds
- the cyclic compounds can be connected to the basic structure via alkyl chains which can comprise heteroatoms such as N, O, Cl, F, Br, I or S as described above
- Hal can represent: I, Cl, Br or F
- $R_3$ and $R_4$, $R_4$ and $R_5$, and $R_5$ and $R_6$ can be bridged independently or via further atoms Preferred pharmaceutical or diagnostic compositions according to the present invention comprise an active substance with a structure according to formula I-5 or formula I-7 described above, wherein the active substance is:

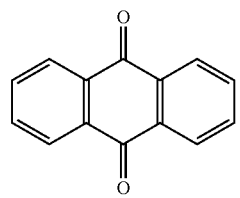
Anthraquinone

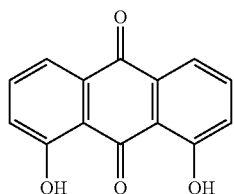
1,8-Dihydroxy-anthraqinone (Danthron)

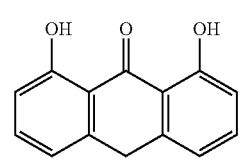
1,8-Dihydroxy-10H-anthracene-9-one (Dithranol/Anthralin)

1,8-Dihydroxy-3-methyl-10H-anthracene-9-one (Chrysarobin)

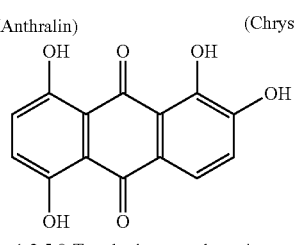
1,2,5,8-Tetrahydroxy-anthraquinone

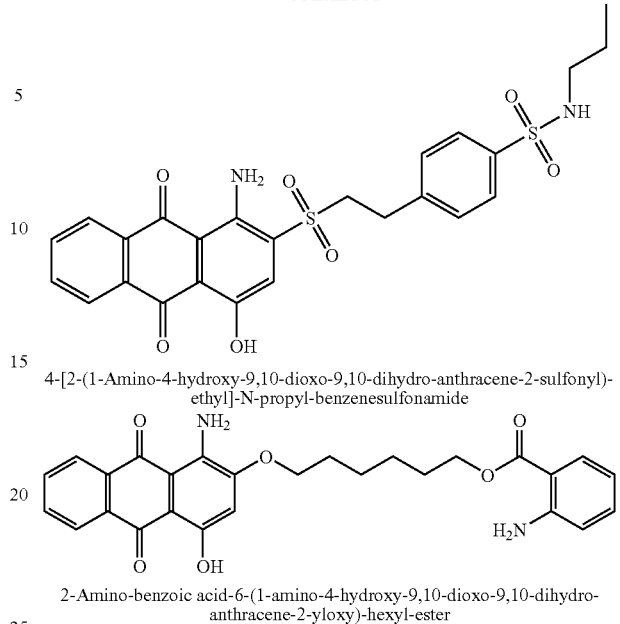

4-[2-(1-Amino-4-hydroxy-9,10-dioxo-9,10-dihydro-anthracene-2-sulfonyl)-ethyl]-N-propyl-benzenesulfonamide 2-Amino-benzoic acid-6-(1-amino-4-hydroxy-9,10-dioxo-9,10-dihydro-anthracene-2-yloxy)-hexyl-ester Other pharmaceutical or diagnostic compositions according to the present invention comprise active substances selected from the following derivatives:

4-[2-(1-Amino-4-hydroxy-9,10-dioxo-9,10-dihydro-anthracene-2-sulfonyl)-ethyl]-N-propyl-benzenesulfonamide, 2-amino-benzoic acid 6-(1-amino-4-hydroxy-9,10-dioxo-9,10-dihydro-anthracene-2-yloxy)-hexylester, 1,8-dihydroxy-3-methyl-10H-anthracene-9-one and 1,2,5,8-tetrahydroxy-anthraquinone.

Molecular Scaffold I-6:

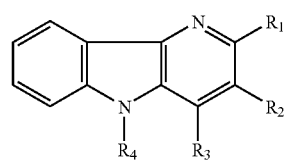

10H-Indolo[3,2b-]quinoline $R_1$ to $R_4$ can be:

H, OH, $NH_2$, Hal

- single- or multi-branched or straight-chain alkyl chains which can comprise 1, 2, 3, 4, 5, 6, 7, 8, 9 or 10 carbon atoms each
- cyclic alkyl chains with 1 or 2 rings or aryl compounds with 1 or 2 rings which can comprise 1, 2, 3, 4, 5, 6, 7, 8, 9 or 10 carbon atoms each
- the mentioned alkyl or aryl groups can also each comprise 1, 2, 3 or 4 heteroatoms such as N, O, Cl, F, Br, I or S, in particular also in the form of amides, esters, nitrites or ether compounds
- the cyclic compounds can be connected to the basic structure via alkyl chains which can comprise heteroatoms such as N, O, Cl, F, Br, I or S as described above
- Hal can represent: I, Cl, Br or F
- $R_1$ and $R_2$, $R_2$ and $R_3$, and $R_3$ and $R_4$ can be bridged independently or via further atoms An example of this group is 10-Benzyl-10H-indolo[3,2-b]quinoline-11-carboxylic acid benzyl ester Group II The chemical agents of group II comprise a 2-oxo-1,2-dihydro-pyridine-3-carbonitrile group (molecular scaffold II-1). Most substances are characterized by a special modification of this structure. This compound (2-amino-7-oxo-6,7-dihydro-thiazole[4,5-f]quinoline-8-carbonitrile) is referred to as molecular scaffold II-1 in Table 1. Table 1 lists all the structures of group II including their structure, chemical name, molecular weight and empirical formula.

Molecular Scaffold II-1

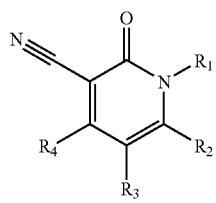

Basic Structure:
2-Oxo-1,2-Dihydro-Pyridine-3-Carbonitrile

The invention encompasses derivatives of the molecular scaffold II-1, $R_1$, $R_2$, $R_3$ and $R_4$ can be:

H, OH, $NH_2$, Hal single- or multi-branched or straight-chain alkyl chains which can comprise 1, 2, 3, 4, 5, 6, 7, 8, 9 or 10 carbon atoms each cyclic alkyl chains with 1 or 2 rings or aryl compounds with 1 or 2 rings which can comprise 1, 2, 3, 4, 5, 6, 7, 8, 9 or 10 carbon atoms each the mentioned alkyl or aryl groups can also each comprise 1, 2, 3 or 4 heteroatoms such as N, O, Cl, F, Br, I or S, in particular also in the form of amides, esters, nitrites or ether compounds the cyclic compounds can be connected to the basic structure via alkyl chains which can comprise heteroatoms such as N, O, Cl, F, Br, I or S as described above Hal can represent: I, Cl, Br or F $R_1$ and $R_2$ can be bridged independently or via further atoms As an example, in particular the compounds represented by the structural formulas below should be protected:

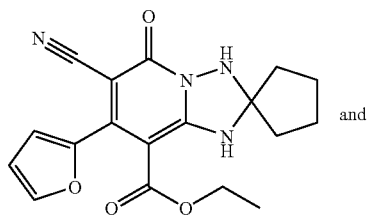

and

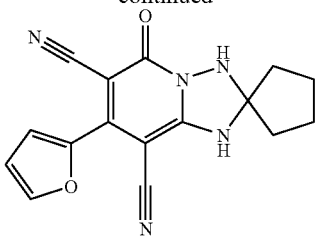

Molecular Scaffold II-2

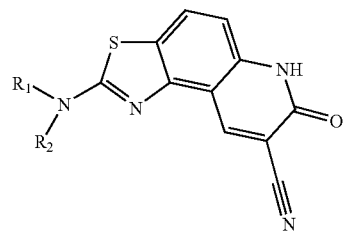

Basic structure: 2-Amino-7-oxo-6,7-dihydro-thiazolo[4,5-f]quinoline-8-carbonitrile The invention encompasses derivatives of the molecular scaffold II-2, wherein $R_1$ and $R_2$ H, OH, $NH_2$, Hal single- or multi-branched or straight-chain alkyl chains which can comprise 1, 2, 3, 4, 5, 6, 7, 8, 9 or 10 carbon atoms each cyclic alkyl chains with 1 or 2 rings or aryl compounds with 1 or 2 rings which can comprise 1, 2, 3, 4, 5, 6, 7, 8, 9 or 10 carbon atoms each the mentioned alkyl or aryl groups can also each comprise 1, 2, 3 or 4 heteroatoms such as N, O, Cl, F, Br, I or S, in particular also in the form of amides, esters, nitriles or ether compounds the cyclic compounds can be connected to the basic structure via alkyl chains which can comprise heteroatoms such as N, O, Cl, F, Br, I or S as described above Hal can represent: I, Cl, Br or F $R_1$ and $R_2$ can be bridged independently or via further atoms Preferred pharmaceutical or diagnostic compositions according to the present invention comprise an active substance with a structure according to formula II-2, wherein the active substance is selected from:

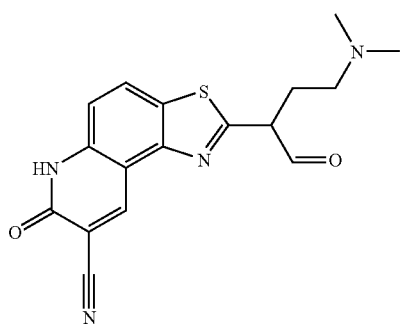

N-(8-Cyano-7-oxo-6,7-dihydro-thiazolo[4,5-f]quinolin-2-yl)-N-(2-dimethylamino-ethyl)-formamide -continued

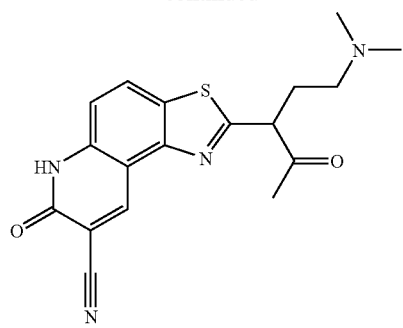

N-(8-Cyano-7-oxo-6,7-dihydro-thiazolo[4,5-f]quinolin-2-yl)-N-(2-dimethylamino-ethyl)-acetamide

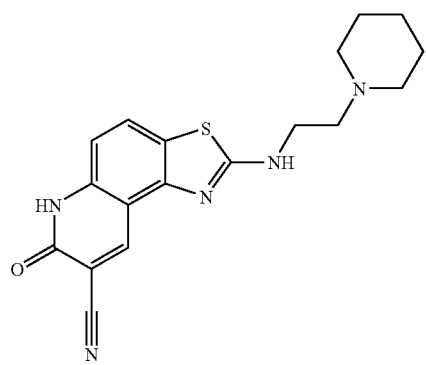

7-Oxo-2-(2-piperidin-1-yl-ethylamino)-6,7-dihydro-thiazolo[4,5-f]quinoline-8-carbonitrile

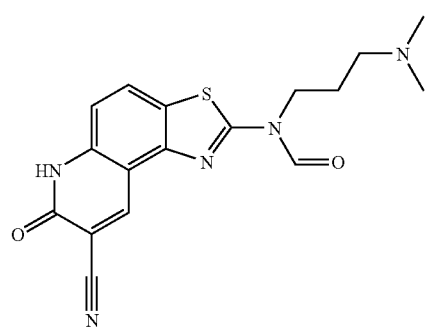

N-(8-Cyano-7-oxo-6,7-dihydro-thiazolo[4,5-f]quinolin-2-yl)-N-(3-dimethylamino-propyl)-formamide

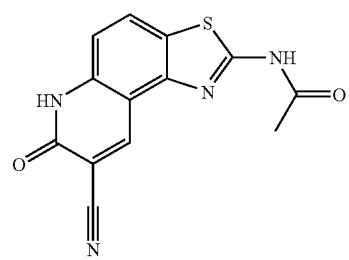

N-(8-Cyano-7-oxo-6,7-dihydro-thiazolo[4,5-f]quinolin-2-yl)-acetamide

-continued

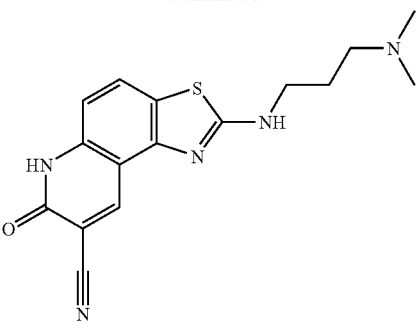

2-(3-Dimethylamino-propylamino)-7-oxo-6,7-dihydro-thiazolo[4,5-f]quinoline-8-carbonitrile

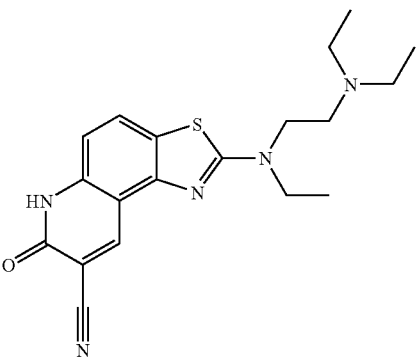

2-[(2-Diethylamino-ethyl)-ethyl-amino]-7-oxo-6,7-dihydro-thiazolo[4,5-f]quinoline-8-carbonitrile

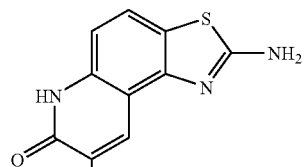

2-Amino-7-oxo-6,7-dihydro-thiazolo[4,5-f]quinoline-8-carbonitrile

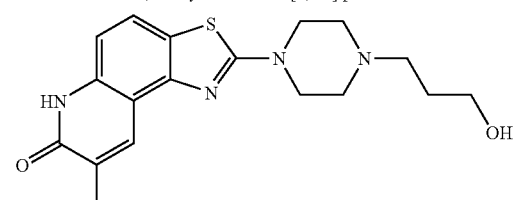

2-[4-(3-hydroxy-propyl)-piperazine-1-yl]-7-oxo-6,7-dihydro-thiazolo[4,5-f]quinoline-8-carbonitrile

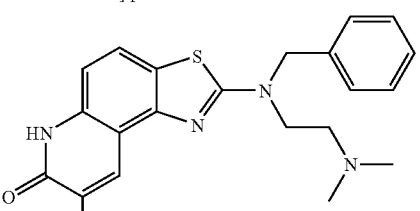

2-[Benzyl-(2-dimethylamino-ethyl)-amino]-7-oxo-6,7-dihydro-thiazolo[4,5-f]quinoline-8-carbonitrile Other pharmaceutical or diagnostic compositions according to the present invention comprise active substances selected from the following derivatives:
1. N-Benzyl-N-(8-cyano-7-oxo-6,7-dihydro-thiazolo[4,5-f] quinoline-8-carbonitrile
2. 2-(2-Hydroxy-ethylamino)-7-oxo-6,7-dihydro-thiazolo[4,5-f]quinoline-8-carbonitrile
3. N-(8-Cyano-7-oxo-6,7-dihydro-thiazolo[4,5-f]quinoline-2-yl)-N-(3-dimethylamino-propyl)-formamide
4. 2-[Benzyl-(2-dimethylamino-ethyl)-amino]7-oxo-6,7-dihydro-thiazolo[4,5-f]quinoline-8-carbonitrile
5. N-(8-Cyano-7-oxo-6,7-dihydro-thiazolo[4,5-f]quinoline-2-yl)-N-(2-dimethylamino-ethyl-formamide
6. 7-Oxo-2-(2-piperidine-1-yl-ethylamino)-6,7-dihydrothiazolo[4,5-f]quinoline-8-carbonitrile
7. N-(8-Cyano-7-oxo-6,7-dihydro-thiazolo[4,5-f]quinoline-2-yl)-N-(2-dimethylamino-ethyl)-acetamide
8. 2-[4-(3-Hydroxy-propyl)-piperazine-1-yl]-7-oxo-6,7-dihydro-thiazolo[4,5-f]quinoline-8-carbonitrile
9. 2-Ethylamino-7-oxo-6,7-dihydro-thiazolo[4,5-f]quinoline-8-carbonitrile
10. 2-Dimethylamino-7-oxo-6,7-dihydro-thiazolo[4,5-f]quinoline-8-carbonitrile
11. 2-Diisopropylamino-7-oxo-6,7-dihydro-thiazolo[4,5-f]quinoline-8-carbonitrile
12. (4-Methoxy-phenylamino)-7-oxo-6,7-dihydro-thiazolo[4,5-f]quinoline-8-carbonitrile
13. N-(-Cyano-7-oxo-6,7-dihydro-thiazolo[4,5-f]quinoline-2-yl)-acetamide
14. 2-Benzylamino-7-oxo-6,7-dihydro-thiazolo[4,5-f]quinoline-8-carbonitrile
15. 2-(4-Methoxy-benzylamino)-7-oxo-6,7-dihydro-thiazolo[4,5-f]quinoline-8-carbonitrile
16. N-(8-Cyano-7-oxo-6,7-dihydro-thiazolo[4,5-f]quinoline-2-yl)-N-(3-dimethylamino-propyl)-acetamide
17. 7-Oxo-2-(2-pyridine-2-yl-ethylamino)-6,7-dihydrothiazolo[4,5-f]quinoline-8-carbonitrile Group III Compounds of group III are characterized by the presence of a nitrogen- or oxygen-containing heterocycle. Group III includes 6 molecular scaffolds (molecular scaffolds III-1 to III-6) (Table 3).

Molecular Scaffold III-1:

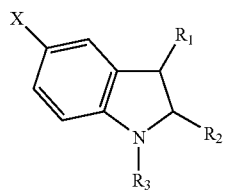

1H-Indole
  X can represent: H, OH, $NH_2$, Hal
  $R_1$ to $R_3$ can be:
  H, OH, $NH_2$, Hal
  single- or multi-branched or straight-chain alkyl chains which can comprise 1, 2, 3, 4, 5, 6, 7, 8, 9 or 10 carbon atoms each
  cyclic alkyl chains with 1 or 2 rings or aryl compounds with 1 or 2 rings which can comprise 1, 2, 3, 4, 5, 6, 7, 8, 9 or 10 carbon atoms each
  the mentioned alkyl or aryl groups can also each comprise 1, 2, 3 or 4 heteroatoms such as N, O, Cl, F, Br, I or S, in particular also in the form of amides, esters, nitrites or ether compounds
  the cyclic compounds can be connected to the basic structure via alkyl chains which can comprise heteroatoms such as N, O, Cl, F, Br, I or S as described above
  Hal can represent: I, Cl, Br or F
  $R_1$ and $R_2$ as well as $R_2$ and $R_3$ can be bridged independently or via further atoms Molecular Scaffold III-2:

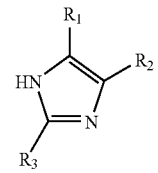

1H-Imidazole
  $R_1$ to $R_3$ can be:
  H, OH, $NH_2$, Hal
  single- or multi-branched or straight-chain alkyl chains which can comprise 1, 2, 3, 4, 5, 6, 7, 8, 9 or 10 carbon atoms each
  cyclic alkyl chains with 1 or 2 rings or aryl compounds with 1 or 2 rings which can comprise 1, 2, 3, 4, 5, 6, 7, 8, 9 or 10 carbon atoms each
  the mentioned alkyl or aryl groups can also each comprise 1, 2, 3 or 4 heteroatoms such as N, O, Cl, F, Br, I or S, in particular also in the form of amides, esters, nitriles or ether compounds
  the cyclic compounds can be connected to the basic structure via alkyl chains which can comprise heteroatoms such as N, O, Cl, F, Br, I or S as described above
  Hal can represent: I, Cl, Br or F
  $R_1$ and $R_2$ can be bridged independently or via further atoms Examples of the substance group:
3-(4-Nitro-imidazole-1-yl)-phenylamine
2-chloro-1H-benzoimidazole-5,6-diamine
5-(2,4-dihydroxy-benzylidene)-2-thioxo-imidazolidine-4-one Molecular Scaffold III-3:

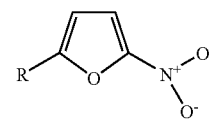

2-Nitro-furan
  R can be:
  H, OH, $NH_2$, Hal
  a single- or multi-branched or straight-chain alkyl chains which can comprise 1, 2, 3, 4, 5, 6, 7, 8, 9 or 10 carbon atoms each
  a cyclic alkyl chain with 1 or 2 rings or an aryl compound with 1 or 2 rings which can comprise 1, 2, 3, 4, 5, 6, 7, 8, 9 or 10 carbon atoms each
  the mentioned alkyl or aryl groups can also each comprise 1, 2, 3 or 4 heteroatoms such as N, O, Cl, F, Br, I or S, in particular also in the form of amides, esters, nitriles or ether compounds
  the cyclic compounds can be connected to the basic structure via alkyl chains which can comprise heteroatoms such as N, O, Cl, F, Br, I or S as described above
  Hal can represent: I, Cl, Br or F Examples of the substance group:
[3-(5-Nitro-furan-2-yl)-allylidene]-thiazole-2-yl-amine
[3,(5-nitro-furan-2-yl)-allylidene]-pyridine-2-yl-amine Molecular Scaffold III-4:

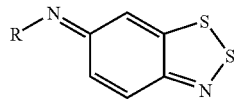

Benzo[1,2,3]dithiazole-6-ylideneamine
R can be:
H, OH, NH$_2$, Hal
a single- or multi-branched or straight-chain alkyl chain which can comprise 1, 2, 3, 4, 5, 6, 7, 8, 9 or 10 carbon atoms each
a cyclic alkyl chain with 1 or 2 rings or an aryl compound with 1 or 2 rings which can comprise 1, 2, 3, 4, 5, 6, 7, 8, 9 or 10 carbon atoms each
the mentioned alkyl or aryl groups can also each comprise 1, 2, 3 or 4 heteroatoms such as N, O, Cl, F, Br, I or S, in particular also in the form of amides, esters, nitriles or ether compounds
the cyclic compounds can be connected to the basic structure via alkyl chains which can comprise heteroatoms such as N, O, Cl, F, Br, I or S as described above
Hal can represent: I, Cl, Br or F
Examples of the substance group:
N-Benzo[1,2,3]dithiazole-6-ylidene-benzene-1,4-diamine Molecular Scaffold III-5:

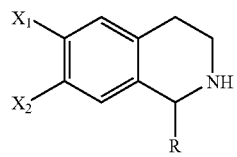

1,2,3,4-Tetrahydro-isoquinoline
X$_1$ and X$_2$ can represent:
H, OH, NH$_2$, Hal
R can be:
H, OH, NH$_2$, Hal
a single- or multi-branched or straight-chain alkyl chain which can comprise 1, 2, 3, 4, 5, 6, 7, 8, 9 or 10 carbon atoms each
a cyclic alkyl chain with 1 or 2 rings or an aryl compound with 1 or 2 rings which can comprise 1, 2, 3, 4, 5, 6, 7, 8, 9 or 10 carbon atoms each
the mentioned alkyl or aryl groups can also each comprise 1, 2, 3 or 4 heteroatoms such as N, O, Cl, F, Br, I or S, in particular also in the form of amides, esters, nitriles or ether compounds
the cyclic compounds can be connected to the basic structure via alkyl chains which can comprise heteroatoms such as N, O, Cl, F, Br, I or S as described above
Hal can represent: I, Cl, Br or F
Examples of this substance group:
1-(3,4-Dihydroxy-benzyl)-1,2,3,4-tetrahydro-isoquinoline-6,7-diol Molecular Scaffold III-6:

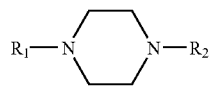

Piperazine
R$_1$ and R$_2$ can represent:
H, OH, NH$_2$, Hal
single- or multi-branched or straight-chain alkyl chains which can comprise 1, 2, 3, 4, 5, 6, 7, 8, 9 or 10 carbon atoms each
cyclic alkyl chains with 1 or 2 rings or aryl compounds with 1 or 2 rings which can comprise 1, 2, 3, 4, 5, 6, 7, 8, 9 or 10 carbon atoms each
the mentioned alkyl or aryl groups can also each comprise 1, 2, 3 or 4 heteroatoms such as N, O, Cl, F, Br, I or S, in particular also in the form of amides, esters, nitrites or ether compounds
the cyclic compounds can be connected to the basic structure via alkyl chains or aryl groups which can comprise heteroatoms as described above
Hal can represent: I, Cl, Br or F
R$_1$ and R$_2$ can be bridged independently or via further atoms
Examples of this substance group:
2,4-Bis-[4-(4-methyl-thiazole-2-yl)-piperazine-1-yl]-pyrimidine
thiophene-2-yl-acetylic acid4-(4-acetyl-piperazine-1-yl)-phenyl-ester Group IV The compounds of this group comprise acid amides which are bonded covalently to cyclic aromatic compounds. Group IV consists of a total of 6 molecular scaffolds (Table 4).

Molecular Scaffold IV-1:

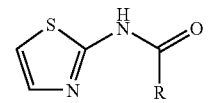

N-Thiazole-2-yl-formamide
R can be:
H, OH, NH$_2$, Hal
a single- or multi-branched or straight-chain alkyl chain which can comprise 1, 2, 3, 4, 5, 6, 7, 8, 9 or 10 carbon atoms each
a cyclic alkyl chain with 1 or 2 rings or an aryl compound with 1 or 2 rings which can comprise 1, 2, 3, 4, 5, 6, 7, 8, 9 or 10 carbon atoms each
the mentioned alkyl or aryl groups can also each comprise 1, 2, 3 or 4 heteroatoms such as N, O, Cl, F, Br, I or S, in particular also in the form of amides, esters, nitrites or ether compounds
the cyclic compounds can be connected to the basic structure via alkyl chains which can comprise heteroatoms such as N, O, Cl, F, Br, I or S as described above
Hal can represent: I, Cl, Br or F
Example of this substance group:
5-[4-(Thiazole-2-yl-carbamoyl)-phenyl]-furan-2-carboxylic acid-thiazole-2-ylamide Molecular Scaffold IV-2:

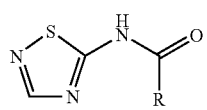

N-[1,2,4]Thiadiazole-5-yl-formamide

R can be:

H, OH, $NH_2$, Hal a single- or multi-branched or straight-chain alkyl chain which can comprise 1, 2, 3, 4, 5, 6, 7, 8, 9 or 10 carbon atoms each a cyclic alkyl chain with 1 or 2 rings or an aryl compound with 1 or 2 rings which can comprise 1, 2, 3, 4, 5, 6, 7, 8, 9 or 10 carbon atoms each the mentioned alkyl or aryl groups can also each comprise 1, 2, 3 or 4 heteroatoms such as N, O, Cl, F, Br, I or S, in particular also in the form of amides, esters, nitrites or ether compounds the cyclic compounds can be connected to the basic structure via alkyl chains which can comprise heteroatoms such as N, O, Cl, F, Br, I or S as described above Hal can represent: I, Cl, Br or F Examples of this substance group:

5-[3-(3-Phenyl-[1,2,4]thiadiazole-5-yl)-ureido]-isophthalic acid dimethyl ester 4-methyl-2-[3-(3-phenyl-[1,2,4]thiadiazole-5-yl)-ureido]-pentanoic acid ethyl ester carbazole-9-carboxylic acid (e-phenyl-[1,2,4]thiadiazole-5-yl)-amide Molecular Scaffold IV-3:

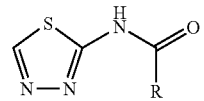

N-[1,3,4]Thiadiazole-2-yl-formamide

R can be:

H, OH, $NH_2$, Hal a single- or multi-branched or straight-chain alkyl chain which can comprise 1, 2, 3, 4, 5, 6, 7, 8, 9 or 10 carbon atoms each a cyclic alkyl chain with 1 or 2 rings or an aryl compound with 1 or 2 rings which can comprise 1, 2, 3, 4, 5, 6, 7, 8, 9 or 10 carbon atoms each the mentioned alkyl or aryl groups can also each comprise 1, 2, 3 or 4 heteroatoms such as N, O, Cl, F, Br, I or S, in particular also in the form of amides, esters, nitriles or ether compounds the cyclic compounds can be connected to the basic structure via alkyl chains which can comprise heteroatoms such as N, O, Cl, F, Br, I or S as described above Hal can represent: I, Cl, Br or F Example of this substance group:

9,10,10-Trioxo-9,10-dihydro-10I6-thioxanthene-3-carboxylic acid-[1,3,4]thiadiazole-2-ylamide Molecular Scaffold IV-4:

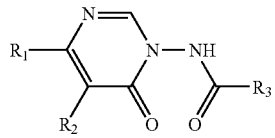

N-(6-Oxo-6H-pyrimidine-1-yl)-formamide $R_1$ to $R_3$ can be:

H, OH, $NH_2$, Hal single- or multi-branched or straight-chain alkyl chains which can comprise 1, 2, 3, 4, 5, 6, 7, 8, 9 or 10 carbon atoms each cyclic alkyl chains with 1 or 2 rings or aryl compounds with 1 or 2 rings which can comprise 1, 2, 3, 4, 5, 6, 7, 8, 9 or 10 carbon atoms each the mentioned alkyl or aryl groups can also each comprise 1, 2, 3 or 4 heteroatoms such as N, O, Cl, F, Br, I or S, in particular also in the form of amides, esters, nitrites or ether compounds the cyclic compounds can be connected to the basic structure via alkyl chains which can comprise heteroatoms such as N, O, Cl, F, Br, I or S as described above Hal can represent: I, Cl, Br or F $R_1$ and $R_2$ can be bridged independently or via further atoms Examples of this substance group:

Since no unambiguous designation of this substance could be found, the structural formula is given to identify this substance:

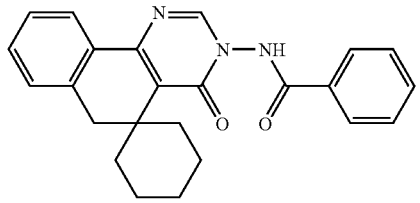 [SMILES: O=C(Nn1cnc2c(c1=O)C1(CCCCC1)Cc1ccccc1-2)c1ccccc1]

Molecular Scaffold IV-5:

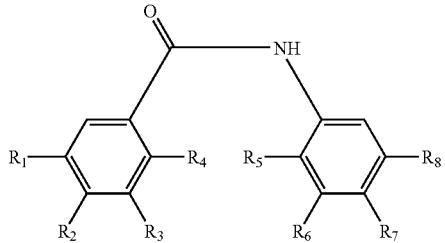

n-Phenyl-benzamide $R_1$ to $R_8$ can be:

H, H, OH, $NH_2$, Hal single- or multi-branched or straight-chain alkyl chains which can comprise 1, 2, 3, 4, 5, 6, 7, 8, 9 or 10 carbon atoms each cyclic alkyl chains with 1 or 2 rings or aryl compounds with 1 or 2 rings which can comprise 1, 2, 3, 4, 5, 6, 7, 8, 9 or 10 carbon atoms each the mentioned alkyl or aryl groups can also each comprise 1, 2, 3 or 4 heteroatoms such as N, O, Cl, F, Br, I or S, in particular also in the form of amides, esters, nitriles or ether compounds the cyclic compounds can be connected to the basic structure via alkyl chains which can comprise heteroatoms such as N, O, Cl, F, Br, I or S as described above Hal can represent: I, Cl, Br or F
Examples include:
N-[3-(3-{3-[(2-Carboxy-phenyl-1-enecarbonyl)-amino]-phenyl}-acryloyl)-phenyl]-phthlalic acid,
acetic acid 2,6-diacetoxy-4-(4-phenoxy-phenylcarbamoyl)-phenyl ester and
5-(4-chloro-benzoylamino)-2,4-dihydroxy-isophthalic acid dimethyl ester
Molecular Scaffold IV-6:

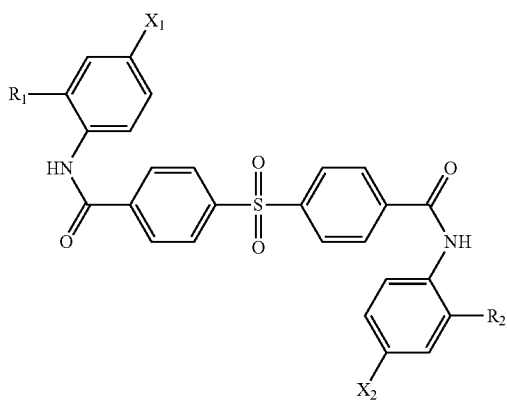

$X_1$ and $X_2$ can be:
H, F, I, Br or Cl, OH or OA, SH or SA, $NH_2$, $NHA_1$ or $NA_1A_2$ or A
A and/or $A_1$ and $A_2$ can be a branched, straight-chain or cyclic alkyl group with 1, 2, 3, 4, 5 or 6 carbon atoms, an aromatic group with 3, 4, 5, 6 or 7 carbon atoms or combinations thereof, wherein individual carbon atoms can also be replaced with 1, 2, 3 or 4 S, N or O atoms.
$R_1$ and $R_2$ can be:
H, OH, $NH_2$, Hal
single- or multi-branched or straight-chain alkyl chains which can comprise 1, 2, 3, 4, 5, 6, 7, 8, 9 or 10 carbon atoms each
cyclic alkyl chains with 1 or 2 rings or aryl compounds with 1 or 2 rings which can comprise 1, 2, 3, 4, 5, 6, 7, 8, 9 or 10 carbon atoms each
the mentioned alkyl or aryl groups can also each comprise 1, 2, 3 or 4 heteroatoms such as N, O, Cl, F, Br, I or S, in particular also in the form of amides, esters, nitrites, acetals, ketals or ether compounds
the cyclic compounds can be connected to the basic structure via alkyl chains which can comprise heteroatoms such as N, O, Cl, F, Br, I or S as described above
Hal can represent: I, Cl, Br or F
As examples, the following compounds should explicitly be protected:
2-{4-[4-(2-Cyano-phenylcarbamoyl)-benzenesulfonyl]-benzoylamino}-3-cyano-benzene and
2-{4-[4-(2-carboxy-4-hydroxy-phenylcarbamoyl)-benzenesulfonyl]-benzoylamino}-5-hydroxy-benzoic acid
Group V Group V contains 4 catechins, which are ingredients of green tea. For this group, patent protection is only sought for the use of the substances and their derivatives in the diagnosis and treatment of Huntington's chorea and other diseases wherein a pathological deposit of polyglutamine-containing proteins is observed. All the structures of group V are listed in the annex, Table 5, including their structure, chemical name, molecular weight and empirical formula. They are the following structures and their derivatives:

(−)-Epigallocatechin gallate (EGCG)(Formula V-1)

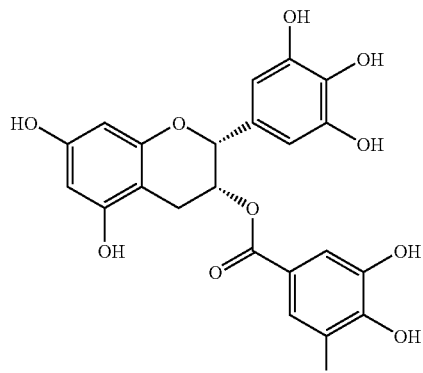

(−)-Gallocatechin gallate (GCG) (Formula V-2)

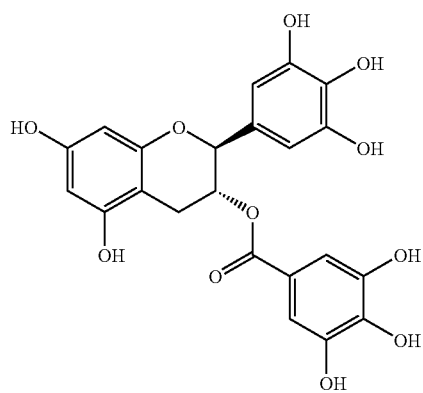

(−)-Epigallocatechin (EGC) (Formula V-3)

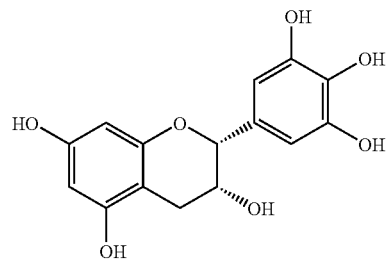 [SMILES: Oc1cc(O)c2c(c1)O[C@H](c1cc(O)c(O)c(O)c1)[C@H](O)C2]

(−)-Gallocatechin (GC) (Formula V-4)

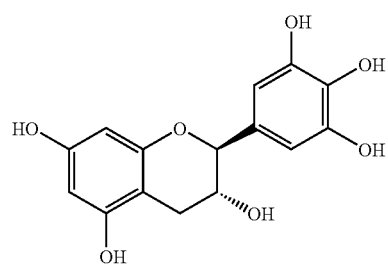 [SMILES: Oc1cc(O)c2c(c1)O[C@@H](c1cc(O)c(O)c(O)c1)[C@H](O)C2]

Group VI

The chemical agents of this group comprise benzothiazole compounds. Group VI encompasses two molecular scaffolds VI-1 and VI-2 (Table 6).

Molecular scaffold VI-1:

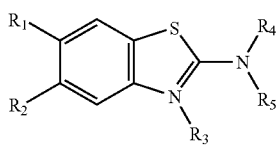

2-Aminobenzothiazole
$R_1$ to $R_5$ can be:
H, OH, $NH_2$, Hal
single- or multi-branched or straight-chain alkyl chains which can comprise 1, 2, 3, 4, 5, 6, 7, 8, 9 or 10 carbon atoms each
cyclic alkyl chains with 1 or 2 rings or aryl compounds with 1 or 2 rings which can comprise 1, 2, 3, 4, 5, 6, 7, 8, 9 or 10 carbon atoms each
the mentioned alkyl or aryl groups can also each comprise 1, 2, 3 or 4 heteroatoms such as N, O, Cl, F, Br, I or S, in particular also in the form of amides, esters, nitriles, acetals, ketals or ether compounds
the cyclic compounds can be connected to the basic structure via alkyl chains which can comprise heteroatoms such as N, O, Cl, F, Br, I or S as described above
Hal can represent: I, Cl, Br or F
$R_1$ and $R_2$, $R_3$ and $R_5$, and $R_4$ and $R_5$ can be bridged independently or via further atoms
Protection is sought explicitly for the following derivatives of molecular scaffold VI-1:
N-(6-Amino-benzothiazole-2-yl)-acetamide
(4-benzothiazole-2-yl-[1,4]diazepan-1-yl)-furan-2-yl-methanone
2-isopropylamino-6H-thiazolo[4,5-f]quinoline-7-one and
(1,3-dimethyl-1,3-dihydro-benzoimidazole-2-ylidenemethyl)-3,6-dimethyl-2,3-dihydro-benzothiazole-2-yl)-diazene
Molecular scaffold VI-2:

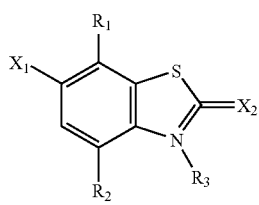

Benzothiazole
$X_1$ can be:
H, F, I, Br or Cl, OH or OA, SH or SA, $NH_2$, $NHA_1$ or $NA_1A_2$ or A
A and/or $A_1$ and $A_2$ can be a branched, straight-chain or cyclic alkyl group with 1, 2, 3, 4, 5 or 6 carbon atoms, an aromatic group with 1, 2, 3, 4, 5, 6 or 7 carbon atoms or combinations thereof, wherein individual carbon atoms can also be replaced with 1, 2, 3 or 4 S, N or O atoms.
$X_2$ can be: O or S
$R_1$ to $R_3$ can be:
H, OH, $NH_2$, Hal
single- or multi-branched or straight-chain alkyl chains which can comprise 1, 2, 3, 4, 5, 6, 7, 8, 9 or 10 carbon atoms each
cyclic alkyl chains with 1 or 2 rings or aryl compounds with 1 or 2 rings which can comprise 1, 2, 3, 4, 5, 6, 7, 8, 9 or 10 carbon atoms each
the mentioned alkyl or aryl groups can also each comprise 1, 2, 3 or 4 heteroatoms such as N, O, Cl, F, Br, I or S, in particular also in the form of amides, esters, nitriles, acetals, ketals or ether compounds
the cyclic compounds can be connected to the basic structure via alkyl chains which can comprise heteroatoms such as N, O, Cl, F, Br, I or S as described above
Hal can represent: I, Cl, Br or F
$R_2$ and $R_3$ can be bridged independently or via further atoms
Example of derivatives of molecular scaffold VI-2:
6-Methoxy-3,4,7-trimethyl-3H-benzothiazole-2-one
Derivatives The present invention also relates to pharmaceutical or diagnostic compositions comprising derivatives of one or more of the active substances mentioned above. Derivatives particularly include those that can for example be obtained by modifications such as the esterification of hydroxy groups with organic and inorganic acids, the introduction or replacement of substituents in aromatics or side chains, the derivatization of hydroxy groups to acetals or ketals, the N-acetylation to amides or phenyl carbamates, the introduction of isosteric or bioisosteric units, the synthesis of Mannich bases or imines, the introduction of branched side chains, the transformation of ketones or aldehydes into Schiff bases, oximes, acetals, ketals, enol esters, oxazolidines, thiazolidines, the replacement of simple side chains with branched side chains and vice versa, the conversion of alkyl substituents to cyclic analogues, or by combinations of these modifications.

TABLE 1

| | | Group II | | | |
|---|---|---|---|---|---|
| EMD | No | Structure | Chemical name | Molecular weight | Empirical formula |
| 45060 | Molecular scaffold II-1 | | Basic structure: 2-Oxo-1,2-dihydro-pyridine-3-carbonitrile | 120.1 | C6H4N2O |

TABLE 1-continued

Group II

| EMD | No | Structure | Chemical name | Molecular weight | Empirical formula |
|---|---|---|---|---|---|
| 220677 | #1 | 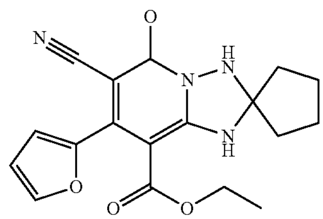 [SMILES: CCOC(=O)C1=C2NC3(CCCC3)NN2C(O)C(C#N)=C1c1ccco1] | ? | 354.4 | C18H18N4O4 |
| 208067 | #2 | 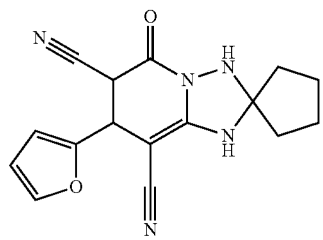 [SMILES: N#CC1=C2NC3(CCCC3)NN2C(=O)C(C#N)C1c1ccco1] | ? | 307.3 | C16H13N5O2 |
| Molecular scaffold II-2 | | | Basic structure: 2-Amino-7-oxo-6,7-dihydro-thiazolo[4,5-f]quinoline-8-carbonitrile | 242.3 | C13H6N4O2S |
| 46618 | #3 | 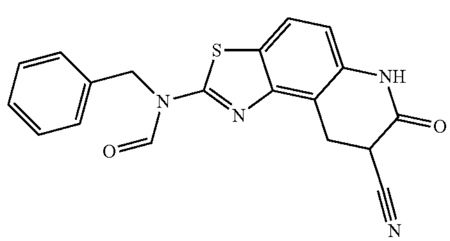 [SMILES: N#CC1Cc2c(ccc3sc(N(C=O)Cc4ccccc4)nc23)NC1=O] | N-Benzyl-N-(8-cyano-7-oxo-6,7-dihydro-thiazolo[4,5-f]quinoline-8-carbonitrile | 360.4 | C19h12N4O2S |
| 46119 | #4 | 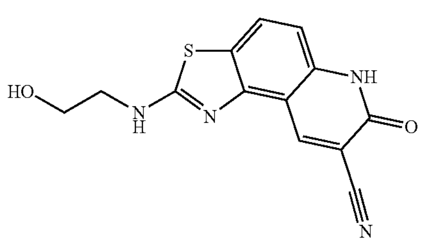 [SMILES: N#Cc1cc2c(ccc3sc(NCCO)nc32)[nH]c1=O] | 2-(2-Hydroxy-ethylamino)-7-oxo-6,7-dihydro-thiazolo[4,5-f]quinoline-8-carbonitrile | 286.3 | C13H10N4O2S |
| 46624 | #5 | 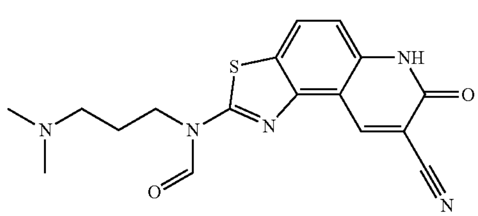 [SMILES: CN(C)CCCN(C=O)c1nc2c(ccc3[nH]c(=O)c(C#N)cc32)s1] | N-(8-Cyano-7-oxo-6,7-dihydro-thiazolo[4,5-f]quinoline-2-yl)-N-(3-dimethylamino-propyl)-formamide | 355.4 | C17H17N5O2S |

TABLE 1-continued

Group II

| EMD | No | Structure | Chemical name | Molecular weight | Empirical formula |
|---|---|---|---|---|---|
| 47659 | #6 | 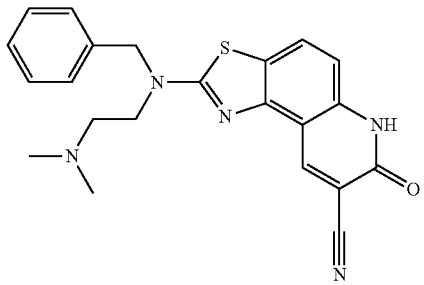 [SMILES: CN(C)CCN(Cc1ccccc1)c1nc2c(ccc3[nH]c(=O)c(C#N)cc32)s1] | 2-[Benzyl-(2-dimethylamino-ethyl)-amino]7-oxo-6,7-dihydro-thiazolo[4,5-f]quinoline-8-carbonitrile | 403.5 | C22H21N5OS |
| 46801 | #7 | 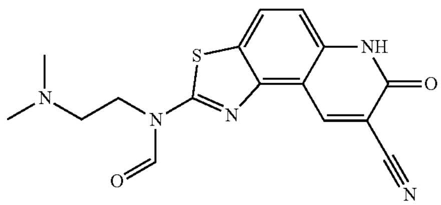 [SMILES: CN(C)CCN(C=O)c1nc2c(ccc3[nH]c(=O)c(C#N)cc32)s1] | N-(8-Cyano-7-oxo-6,7-dihydro thiazolo[4,5-f]quinoline-2-yl)-N-(2-dimethylamino-ethyl-formamide | 341.4 | C16H15N5O2S |
| 46802 | #8 | 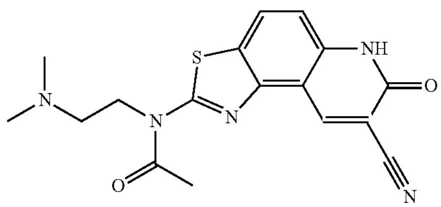 | 7-Oxo-2-(2-piperidine-1-yl-ethylamino)-6,7-dihydrothiazolo[4,5-f]quinoline 8-carbonitrile | 353.4 | C18H19N5OS |
| 46832 | #9 | 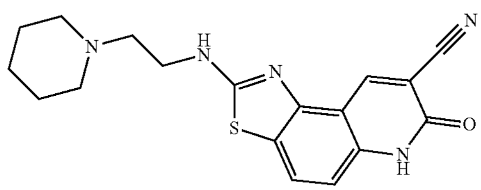 [SMILES: N#Cc1cc2c(ccc3sc(NCCN4CCCCC4)nc32)[nH]c1=O] | N-(8-Cyano-7-oxo-6,7-dihydro thiazolo[4,5-f]quinoline-2-yl)-N-(2-dimethylamino-ethyl)-acetamide | 355.4 | C17H17N5O2S |
| 47009 | #10 | 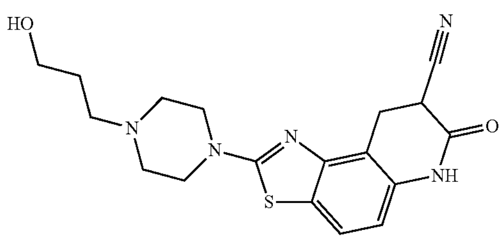 [SMILES: N#CC1Cc2c(ccc3sc(N4CCN(CCCO)CC4)nc23)NC1=O] | 2-[4-(3-Hydroxy-propyl)-piperazine-1-yl]-7-oxo-6,7-dihydro-thiazolo[4,5-f]quinoline-8-carbonitrile | 369.4 | C18H19N5O2S |
| 44837 | #11 | 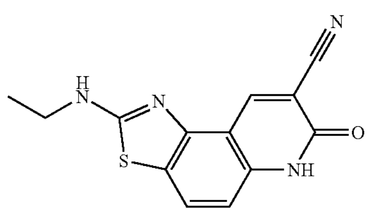 [SMILES: CCNc1nc2c(ccc3[nH]c(=O)c(C#N)cc32)s1] | 2-Ethylamino-7-oxo-6,7-dihydro-thiazolo[4,5-f]quinoline-8-carbonitrile | 270.3 | C13H10N4OS |
| 44841 | #12 | 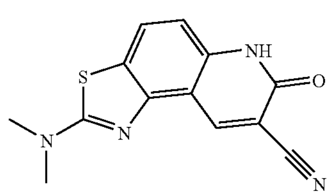 [SMILES: CN(C)c1nc2c(ccc3[nH]c(=O)c(C#N)cc32)s1] | 2-Dimethylamino-7-oxo-6,7-dihydro-thiazolo[4,5-f]quinoline-8-carbonitrile | 270.3 | C13H10N4OS |

| EMD | No | Structure | Chemical name | Molecular weight | Empirical formula |
|---|---|---|---|---|---|
| | | Group II | | | |
| 44843 | #13 | 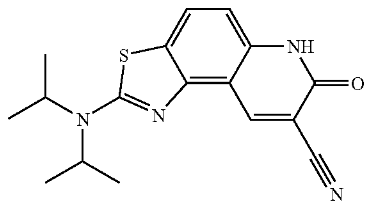 | 2-Diisopropylamino-7-oxo-6,7-dihydro-thiazolo[4,5-f]quinoline-8-carbonitrile | 326.4 | C17H18N4O2S |
| 45061 | #14 | 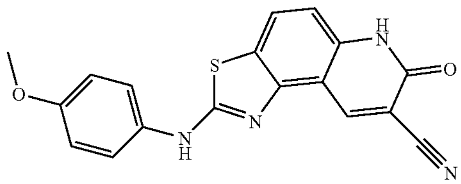 | (4-Methoxy-phenylamino)-7-oxo-6,7-dihydro-thiazolo[4,5-f]quinoline-8-carbonitrile | 348.4 | C18H12N4O2S |
| 45063 | #15 | 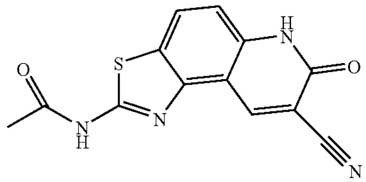 | N-(-Cyano-7-oxo-6,7-dihydro-thiazolo[4,5-f]quinoline-2-yl)-acetamide | 284.3 | C13H8N4O2S |
| 46472 | #16 | 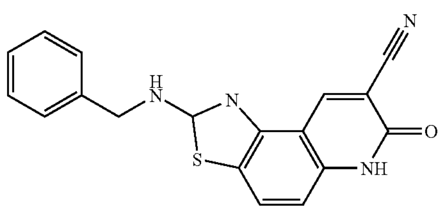 | 2-Benzylamino-7-oxo-6,7-dihydro-thiazolo[4,5-f]quinoline-8-carbonitrile | 332.4 | C18H12N4OS |
| 46622 | #17 | 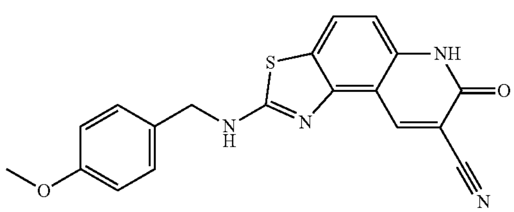 | 2-(4-Methoxy-benzylamino)-7-oxo-6,7-dihydro-thiazolo[4,5-f]quinoline-8-carbonitrile | 362.4 | C19H14N4O2S |
| 46626 | #18 | 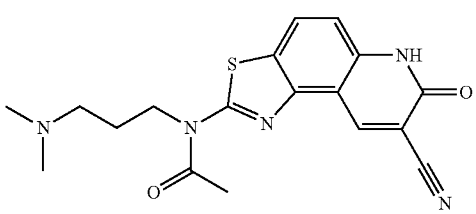 | N-(8-Cyano-7-oxo-6,7-dihydro thiazolo[4,5-f]quinoline-2-yl)-N (3-dimethylamino-propyl)-acetamide | 369.4 | C18H19N5O2S |
| 46836 | #19 | 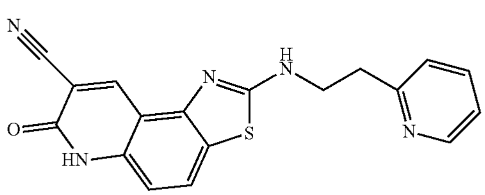 | 7-Oxo-2-(2-pyridine-2-yl-ethylamino)-6,7-dihydrothiazolo[4,5-f]quinoline 8-carbonitrile | 347.4 | C18H13N5OS |

TABLE 2

Group I

| EMD | No | Structure | Chemical name | Molecular weight | Empirical formula |
|---|---|---|---|---|---|
| Molecular scaffold I-1 | | | Basic structure: 1H-perimidine | | |
| 35222 | #1 | 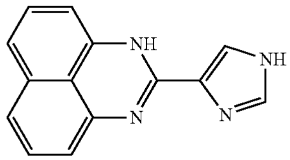 [SMILES: c1cc2c3c(cccc3c1)NC(c1c[nH]cn1)=N2] | 2-(1H-Imidazole-4-yl)-1H-perimidine | 234.3 | C14H10N4 |
| 35361 | #2 | 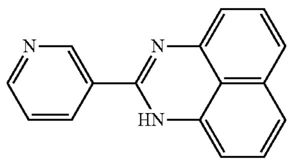 [SMILES: c1cncc(C2=Nc3cccc4cccc(c34)N2)c1] | 2-Pyridine-3-yl-1H-perimidine | 245.3 | C16H11N3 |
| Molecular scaffold I-2 | | | Basic structure: 4,5-Dihydro-pyrrolo[3,2,1-ij]quinoline-6-one | | |
| 207852 | #3 | 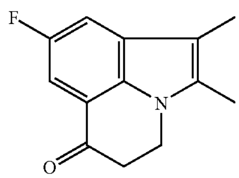 | 8-Fluoro-1,2-dimethyl-4,5-dihydro-pyrrolo[3,5-ij]quinoline-6-one | 233.3 | C16H16FNO |
| Molecular scaffold I-3 | | | Basic structure: Tetrahydro-fluorene | | |
| 127707 | #4 | 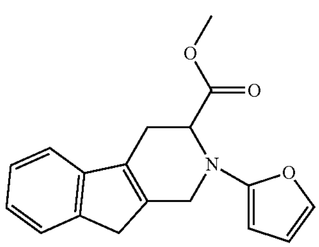 [SMILES: COC(=O)C1CC2=C(Cc3ccccc32)CN1c1ccco1] | 2-Furan-2-yl-2,3,4,9-tetrahydro-1H-indeno[2,3-c]pyridine-3-carboxylic acid methyl ester | 295.3 | C18H17NO3 |
| Molecular scaffold I-4 | | | Basic structure: Anthracene | | |

TABLE 2-continued

Group I

| EMD | No | Structure | Chemical name | Molecular weight | Empirical formula |
|---|---|---|---|---|---|
| 171360 | #5 | 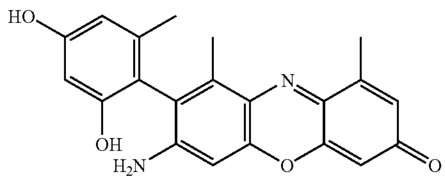 [SMILES: Cc1cc(=O)cc2oc3cc(N)c(-c4c(C)cc(O)cc4O)c(C)c3nc1-2] | 7-Amino-8-[2,4-dihydroxy-6-methyl-phenyl)-1,9-dimethyl-phenoxazine-3-one | 362.4 | C21H18N2O4 |
| 36934 | #6 | 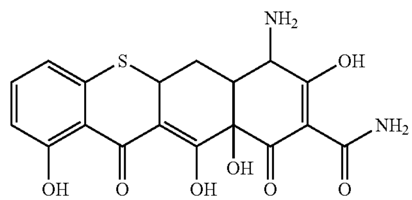 [SMILES: NC(=O)C1=C(O)C(N)C2CC3Sc4cccc(O)c4C(=O)C3=C(O)C2(O)C1=O] | 7-Amino-1,8,10a,11-tetraydroxy-10,12-dioxo-6,6a,7,10,10a,12-hexahydro-5aH-5-thia-naphthacene-9-carboxylic acid amide | 404.4 | C18H16N2O7S |
| | Molecular scaffold I-5 | | Basic structure: 4a,9a-Dihydro-anthraquinone | | |
| 79809 | #7 | 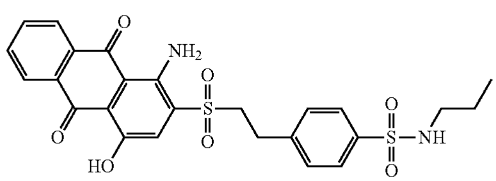 [SMILES: CCCNS(=O)(=O)c1ccc(CCS(=O)(=O)c2cc(O)c3c(c2N)C(=O)c2ccccc2C3=O)cc1] | 4-[2-(1-Amino-4-hydroxy-9,10dioxo-9,10-dihydro-anthracene-2-sulfonyl)-ethyl]-N-propyl-benzenesulfonamide | 528.6 | C25H24N2O7S2 |
| 79810 | #8 | 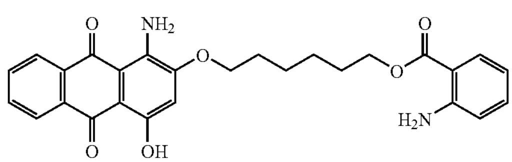 [SMILES: Nc1ccccc1C(=O)OCCCCCCOc1cc(O)c2c(c1N)C(=O)c1ccccc1C2=O] | 2-Amino-benzoic acid 6-(1-amino-4-hydroxy-9,10-dioxo-9,10-dihydro-anthracene-2-yloxy)-hexyl ester | 474.5 | C27H26N2O6 |
| 171211 | #9 | 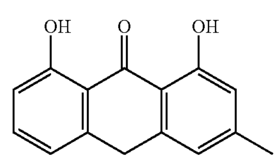 [SMILES: Cc1cc(O)c2c(c1)Cc1cccc(O)c1C2=O] | 1,8-Dihydroxy-3-methyl-10H-anthracene-9-one | 240.3 | C15H12O3 |
| 19916 | #10 | 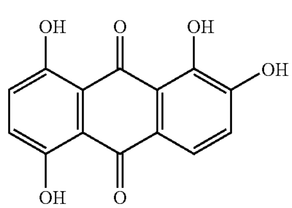 [SMILES: O=C1c2ccc(O)c(O)c2C(=O)c2c(O)ccc(O)c21] | 1,2,5,8-Tetrahydroxy-anthraquinone | 272.3 | C14H8O6 |
| | Molecular scaffold I-6 | | Basic structure: 10H-Indolo[3,2-b]quinoline | | |

TABLE 2-continued

Group I

| EMD No | Structure | Chemical name | Molecular weight | Empirical formula |
|---|---|---|---|---|
| 84508 #11 | | 10-benzyl-10H-indolo[3,2-b]quinoline-11-carboxylic acid benzyl ester | 442.5 | C30H22N2O2 |

TABLE 3

Group III

| EMD No | Structure | Chemical name | Molecular weight | Empirical formula |
|---|---|---|---|---|
| Molecular scaffold III 1 | | Basic structure: 1H-Indole | | |
| 162201 #1 | | 5-(5-Fluoro-1H-indole-3-ylmethylene)-3-methyl-2-thioxo-thiazolidine-4-one | 308.4 | C14H13FN2OS2 |
| 155938 #2 | | 1-(4-Hexyloxy-benzoyl)-1H-indole-2,3-dione | 351.4 | C21H21NO4 |
| Molecular scaffold III 2 | | Basic structure: 1H-Imidazole | | |
| 127211 #3 | | 3-(4-Nitro-imidazole-1-yl)-phenylamine | 204.19 | C9H8N4O2 |

TABLE 3-continued

| Group III | | | | | |
|---|---|---|---|---|---|
| EMD | No | Structure | Chemical name | Molecular weight | Empirical formula |
| 149571 | #4 | | 2-Chloro-1H-benzoimidazole-5,6-diamine | 182.6 | C7H7ClO4 |
| 148257 | #5 | | 5-(2,4-Dihydroxy-benzylidene)-2-thioxo-imidazolidine-4-one | 236.5 | C10H8N2O3S |
| Leitstruktur III-3 | | | Basic structure: 2-Nitro-furan | | |
| 91924 | #6 | | [3-(5-Nitro-furan-2-yl)-allylidene]-thiazole-2-yl-amine | 249.2 | C10H7N3O3S |
| 91876 | #7 | | [3,(5-Nitro-furan-2-yl)-allylidene]-pyridine-2-yl-amine | 243.2 | C12H9N3O3 |
| Molecular scaffold III 4 | | | Basic structure: Benzo[1,2,3]dithiazole-6-ylideneamine | | |
| 41693 | #8 | | N-Benzo[1,2,3]dithiazole-6-ylidene-benzene-1,4-diamine | 259.3 | C12H9N3S2 |
| Molecular scaffold III 5 | | | Basic structure: 1,2,3,4-Tetrahydro-isoquinoline | | |
| 16797 | #9 | | 1-(3,4-Dihydroxy-benzyl)-1,2,3,4-tetrahydro-isoquinoline-6,7-diol | 287.3 | C16H17NO4 |
| Molecular scaffold III 6 | | | Basic structure: Piperazine | | |

TABLE 3-continued

Group III

| EMD | No | Structure | Chemical name | Molecular weight | Empirical formula |
|---|---|---|---|---|---|
| 24445 | #10 | 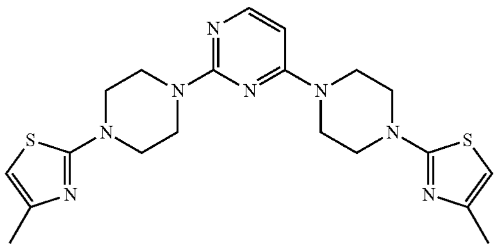 [SMILES: Cc1csc(N2CCN(c3ccnc(N4CCN(c5nc(C)cs5)CC4)n3)CC2)n1] | 2,4-Bis-[4-(4-methyl-thiazole-2-yl)-piperazine-1-yl]-pyrimidine | 442.6 | C20H26N8S2 |
| 208031 | #11 | 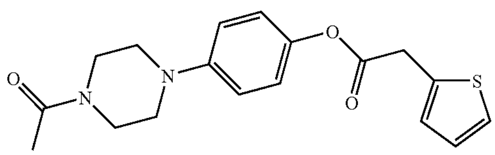 [SMILES: CC(=O)N1CCN(c2ccc(OC(=O)Cc3cccs3)cc2)CC1] | Thiophene-2-yl-acetic acid 4-(4-acetyl-piperazine-1-yl)-phenyl ester | 344.4 | C18H20N2O3S |

TABLE 4

Group IV
Molecular scaffolds L1-L6: R can be replaced by amine or aryl group or H

| EMD | No | Structure | Chemical name | Molecular weight | Empirical formula |
|---|---|---|---|---|---|
| Molecular scaffold IV-1 | | | Basic structure: N-Thiazole-2-yl-formamide | — | — |
| 156140 | #1 | 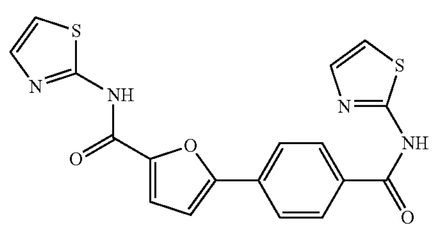 [SMILES: O=C(Nc1nccs1)c1ccc(-c2ccc(C(=O)Nc3nccs3)o2)cc1] | 5-[4-(Thiazole-2-ylcarbamoyl)-phenyl]-furan-2-carboxylic acid thiazole-2-ylamide | 396.4 | C18H12N4O3S2 |
| Molecular scaffold IV-2 | | | Basic structure: N-[1,2,4]Thiadiazole-5-yl-formamide | — | — |
| 139895 | #2 | 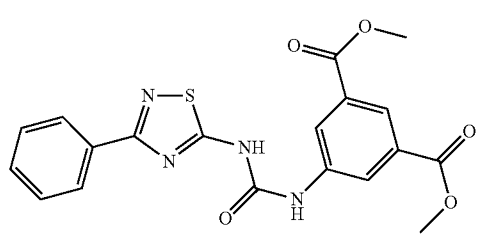 [SMILES: COC(=O)c1cc(NC(=O)Nc2nc(-c3ccccc3)ns2)cc(C(=O)OC)c1] | 5-[3-(3-Phenyl-[1,2,4]thiadiazole-5-yl)-ureido]isophthalic acid dimethylester | 412.2 | C19H16N4O5S |
| 139061 | #3 | 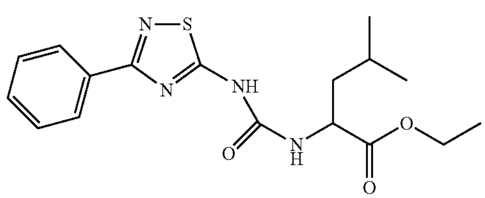 [SMILES: CCOC(=O)C(CC(C)C)NC(=O)Nc1nc(-c2ccccc2)ns1] | 4-Methyl-2-[3-(3-phenyl-[1,2,4]thiadiazole-5-yl)-ureido]pentanoic acid ethyl ester | 362.4 | C17H23N4O2S |

TABLE 4-continued

Group IV
Molecular scaffolds L1-L6: R can be replaced by amine or aryl group or H

| EMD | No | Structure | Chemical name | Molecular weight | Empirical formula |
|---|---|---|---|---|---|
| 139695 | #4 | 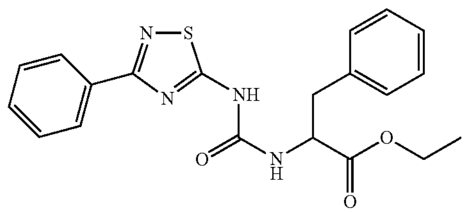 [SMILES: CCOC(=O)C(Cc1ccccc1)NC(=O)Nc1nc(-c2ccccc2)ns1] | 3-Phenyl-2-[3-(3-phenyl-[1,2,4]thiadiazole-5-yl)ureido]-propionic acid ethyl ester | 396.5 | C20H20N4O3S |
| 139815 | #5 | 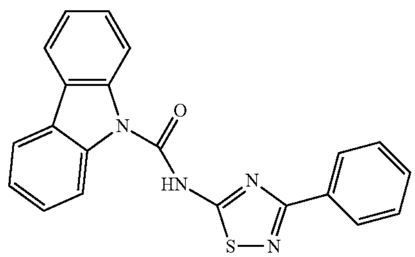 [SMILES: O=C(Nc1nc(-c2ccccc2)ns1)n1c2ccccc2c2ccccc21] | Carbazole-9-carboxylic acid (e-phenyl-[1,2,4]thiadiazole-5-yl)-amide | 370.4 | C21H14N4OS |
| | Molecular scaffold IV-3 | | Basic structure: N-[1,3,4]Thiadiazole-2-yl-formamide | — | — |
| 126117 | #6 | 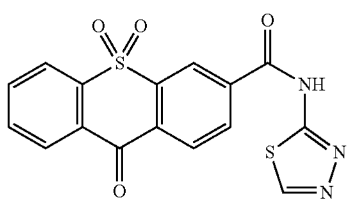 [SMILES: O=C(Nc1nncs1)c1ccc2c(c1)S(=O)(=O)c1ccccc1C2=O] | 9,10,10-Trioxo-9,10-dihydro-10λ6-thioxanthene-3-carboxylic acid [1,3,4]thiadiazole-2-ylamide | 371.4 | C16H9N3O4S2 |
| | Molecular scaffold IV-4 | | Basic structure: N-(6-Oxo-6H-pyrimidine-1-yl)-formamide | — | — |
| 133081 | #7 | 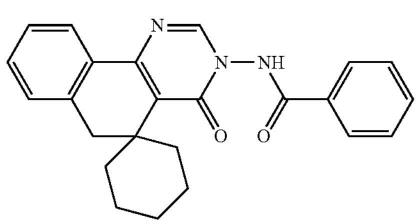 [SMILES: O=C(Nn1cnc2c(c1=O)C1(CCCCC1)Cc1ccccc1-2)c1ccccc1] | ? | 385.5 | C24H23N3O2 |
| | Molecular scaffold IV-5 | | Basic structure: n-Phenyl-benzamide | | |

TABLE 4-continued

Group IV
Molecular scaffolds L1-L6: R can be replaced by amine or aryl group or H

| EMD | No | Structure | Chemical name | Molecular weight | Empirical formula |
| --- | --- | --- | --- | --- | --- |
| 98228 | #8 | 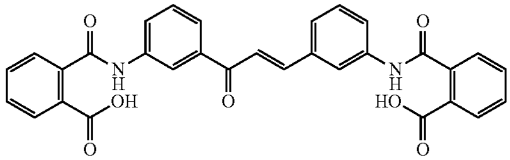 [SMILES: O=C(/C=C/c1cccc(NC(=O)c2ccccc2C(=O)O)c1)c1cccc(NC(=O)c2ccccc2C(=O)O)c1] | N-[3-(3-(3-[(2-Carboxy-phenyl-1-enecarbonyl)-amino]-phenyl]-acryloyl)-phenyl]-phthlamic acid | 534.5 | C31H22N2O7 |
| 118762 | #9 | 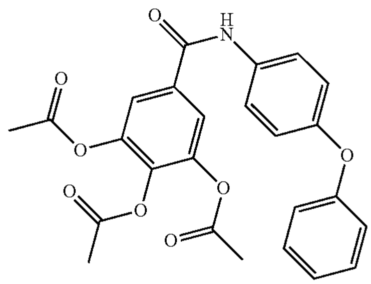 [SMILES: CC(=O)Oc1cc(C(=O)Nc2ccc(Oc3ccccc3)cc2)cc(OC(C)=O)c1OC(C)=O] | Acetic acid 2,6-diacetoxy-4-(4-phenoxy-phenylcarbamoyl)-phenyl ester | 463.4 | C25H22NO8 |
| 18024 | #10 | 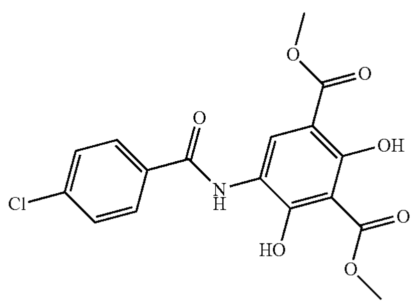 [SMILES: COC(=O)c1cc(NC(=O)c2ccc(Cl)cc2)c(O)c(C(=O)OC)c1O] | 5-(4-Chloro-benzoylamino)-2,4-dihydroxy-isophthalic acid dimethyl ester | 379 | C17H14ClNO7 |
| | Molecular scaffold IV-6 | | ? | | |
| 208123 | #11 | 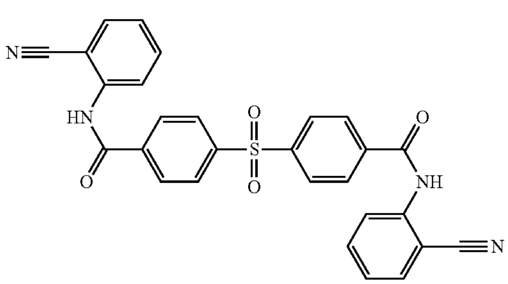 [SMILES: N#Cc1ccccc1NC(=O)c1ccc(S(=O)(=O)c2ccc(C(=O)Nc3ccccc3C#N)cc2)cc1] | 2-[4-[4-(2-Cyano-phenylcarbamoyl)-benzenesulfonyl]-benzoylamino]-3-cyano-benzene | 506.5 | C28H18N4O4S |

TABLE 4-continued

Group IV

Molecular scaffolds L1-L6: R can be replaced by amine or aryl group or H

| EMD | No | Structure | Chemical name | Molecular weight | Empirical formula |
|---|---|---|---|---|---|
| 208125 | #12 | 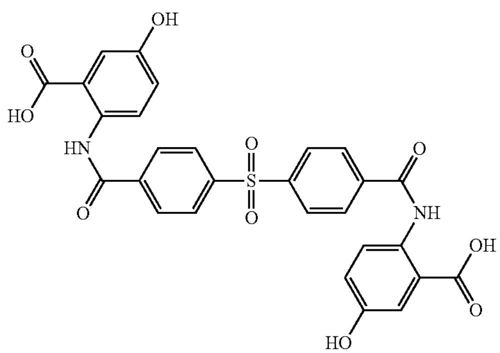 [SMILES: O=C(Nc1ccc(O)cc1C(=O)O)c1ccc(S(=O)(=O)c2ccc(C(=O)Nc3ccc(O)cc3C(=O)O)cc2)cc1] | 2-[4-[4-(2-Carboxy-4-hydroxy-phenylcarbamoyl)-benzenesulfonyl]-benzoylamino]-5-hydroxy-benzoic acid | 576.5 | C28H20N2O10S |

TABLE 5

Group V

| Name | Structure | Chemical name | Molecular weight | Empirical formula |
|---|---|---|---|---|
| EGCG | 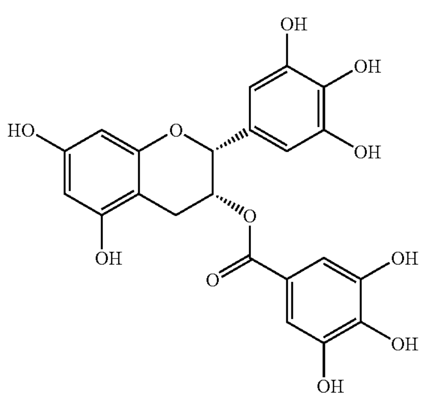 [SMILES: O=C(O[C@@H]1Cc2c(O)cc(O)cc2O[C@@H]1c1cc(O)c(O)c(O)c1)c1cc(O)c(O)c(O)c1] | (−)-Epigallocatechin gallate | 454.4 | C22H18O11 |
| GCG | 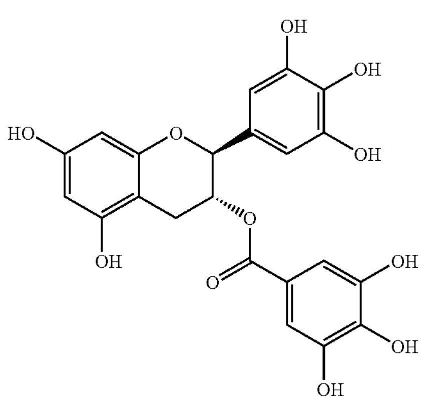 [SMILES: O=C(O[C@@H]1Cc2c(O)cc(O)cc2O[C@H]1c1cc(O)c(O)c(O)c1)c1cc(O)c(O)c(O)c1] | (−)-Gallocatechin gallate | 454.4 | C22H18O11 |

TABLE 5-continued

Group V

| Name | Structure | Chemical name | Molecular weight | Empirical formula |
|---|---|---|---|---|
| EGC | 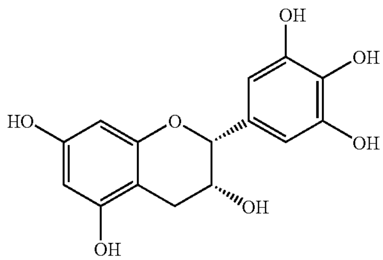 [SMILES: Oc1cc(O)c2c(c1)O[C@H](c1cc(O)c(O)c(O)c1)[C@H](O)C2] | (−)-Epigallocatechin | 306.3 | C15H14O7 |
| GC | 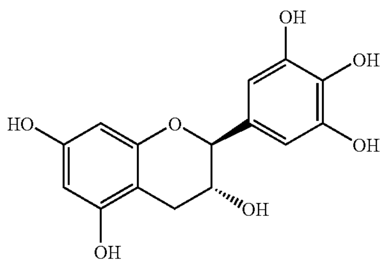 [SMILES: Oc1cc(O)c2c(c1)O[C@@H](c1cc(O)c(O)c(O)c1)[C@H](O)C2] | (−)-Gallocatechin | 306.3 | C15H14O7 |

TABLE 6

Group VI (Benzothiazoles)

| Name | | Structure | Chemical name | Molecular weight | Empirical formula |
|---|---|---|---|---|---|
| | Molecular scaffold VI-1 | (R1, R2 on benzene ring; R3 on N; R4, R5 on amino N) | Basic structure: 2-Aminobenzothiazole | | |
| 390632 | #1 | 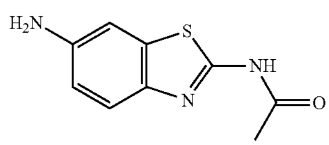 | N-(6-Amino-benzothiazole2-yl)-acetamide | 207.3 | C9H9N3OS |
| 37821 | #2 | 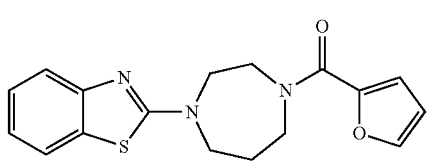 [SMILES: O=C(c1ccco1)N1CCCN(c2nc3ccccc3s2)CC1] | (4-Benzothiazole-2-yl-[1,4]diazepan-1-yl)-furan-2-yl-methanone | 327.4 | C17H17N3O2S |
| 46269 | #3 | 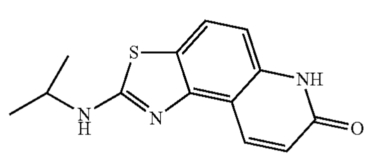 [SMILES: CC(C)Nc1nc2c(ccc3[nH]c(=O)ccc32)s1] | 2-Isopropylamino-6H-thiazolo[4,5-f]quinoline-7-one | 259.3 | C16H13N3OS |
| 124918 | #4 | 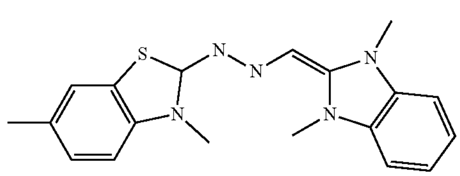 [SMILES: Cc1ccc2c(c1)SC(NNC=C1N(C)c3ccccc3N1C)N2C] | (1,3-Dimethyl-1,3-dihydro-benzoimidazole-2-ylidenemethyl)-3,6-dimethyl-2,3-dihydro-benzothiazole-2-yl)-diazene | 351.5 | C19H21N5S |

TABLE 6-continued

Group VI
(Benzothiazoles)

| Name | Structure | Chemical name | Molecular weight | Empirical formula |
|---|---|---|---|---|
| Molecular scaffold VI-2 |  Basic structure: Benzothiazole | | | |
| 478931 #5 | 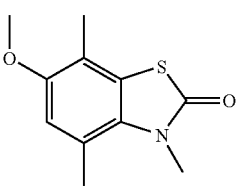 | 6-Methoxy-3,4,7-trimethyl-3H-benzothiazole-2-one | 223.3 | C11H13NO2S |

The figures show:

FIG. 1: Influence of 7-amino-8-(2,4-dihydroxy-6-methyl-phenyl)-1,9-dimethyl-phenoxazine-3-one in vitro on the aggregation von mutant huntingtin and amyloid β.

FIG. 2: Examination of the effects of 7-amino-8-(2,4-dihydroxy-6-methyl-phenyl)-1,9-dimethyl-phenoxazine-3-one in the cell culture model of Huntington's chorea.

Figure 3:
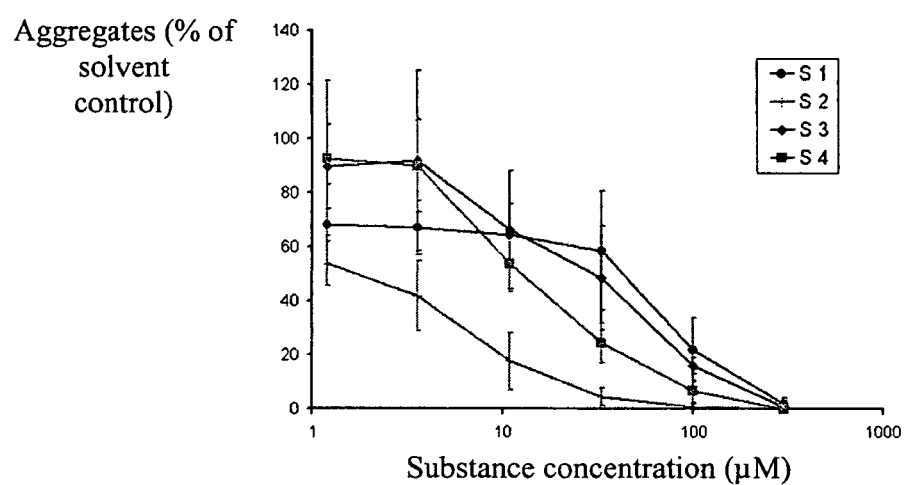

FIG. 3: Inhibition of the aggregation of wild type $A\beta_{1-42}$ (quantification of SDS-insoluble aggregates by means of membrane filter method)

Figure 4:
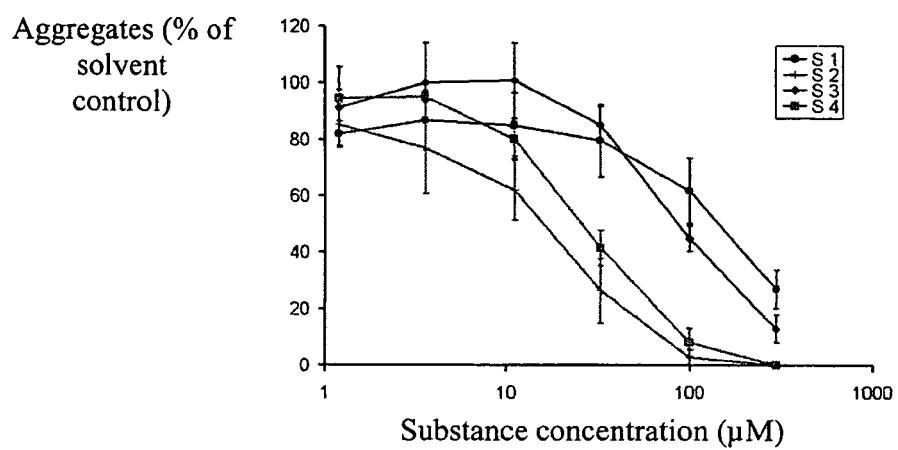

FIG. 4: Inhibition of the aggregation of wild type $A\beta_{1-42}$ (quantification of SDS-insoluble aggregates by means of membrane filter method)

Figure 5:
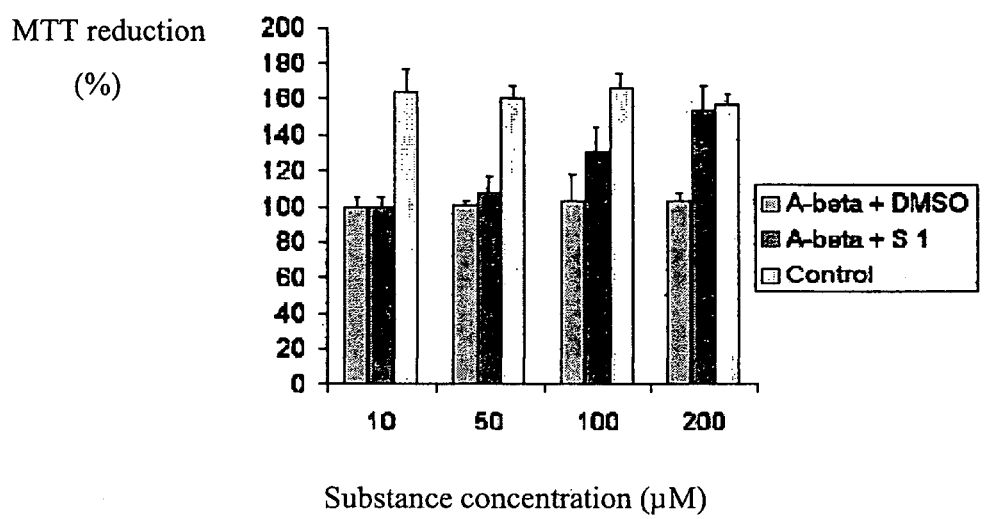

FIG. 5: Inhibition of toxicity of extracellular wild type $A\beta_{1-42}$ by the substances in mammalian cells (neuronally differentiated PC12 cells: Identification by means of MTT test) (quantification of SDS-insoluble aggregates by means of membrane filter method)

Figure 6:
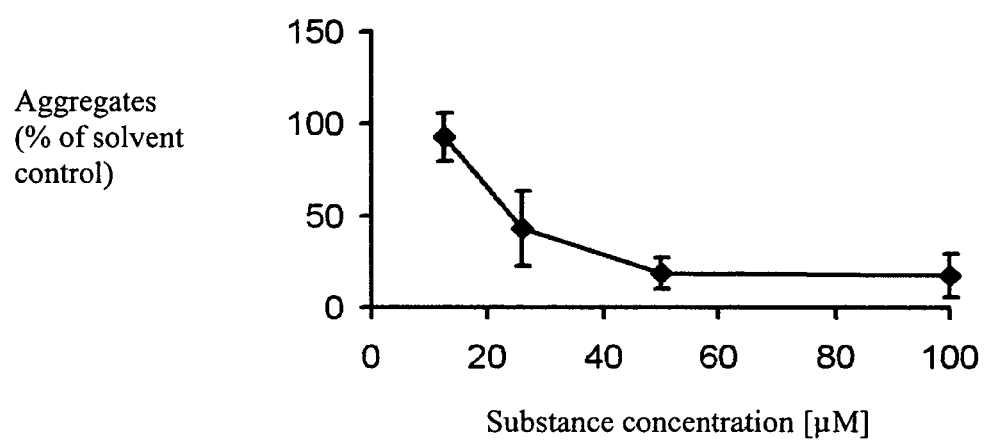

FIG. 6: Inhibition of the aggregation of huntingtin (Exon-1) (quantification of SDS-insoluble aggregates by means of membrane filter method)

Figure 7:
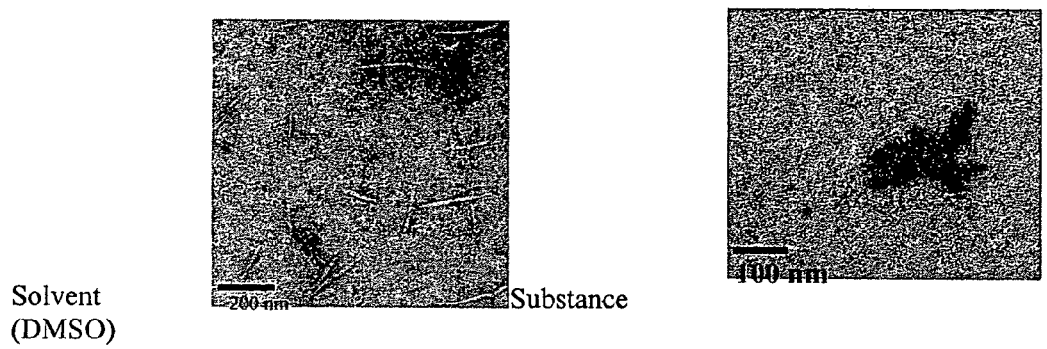

FIG. 7: Inhibition of the amyloid fibril formation of huntingtin (Exon-1) (electron microscopy)

Figure 8:
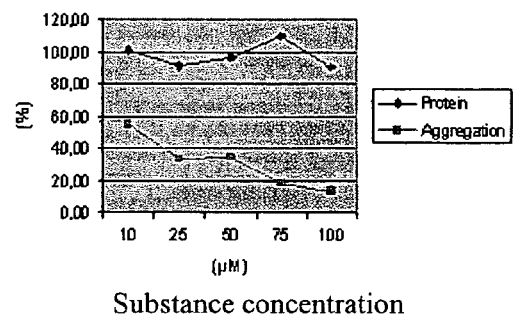

FIG. 8: Inhibition of the aggregation of ataxin-3 in mammalian cells (quantification of SDS-insoluble aggregates by means of membrane filter method)

Figure 9:
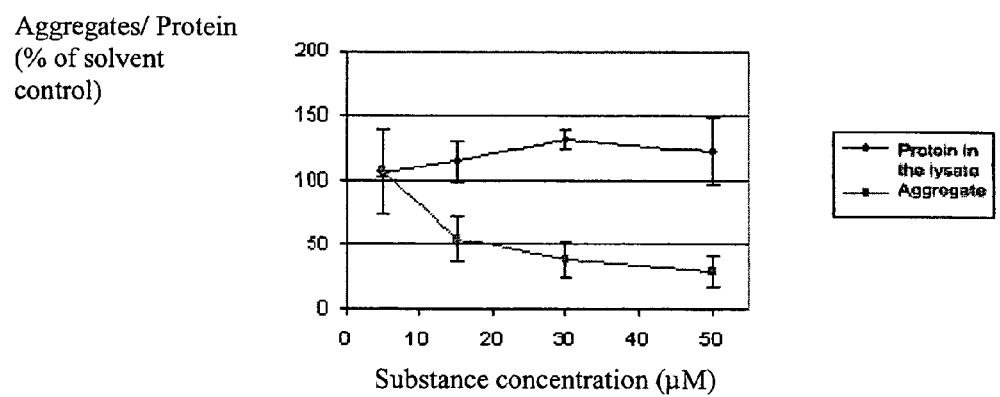

FIG. 9: Inhibition of the aggregation of huntingtin in mammalian cells (quantification of SDS-insoluble aggregates by means of membrane filter method)

Figure 10:
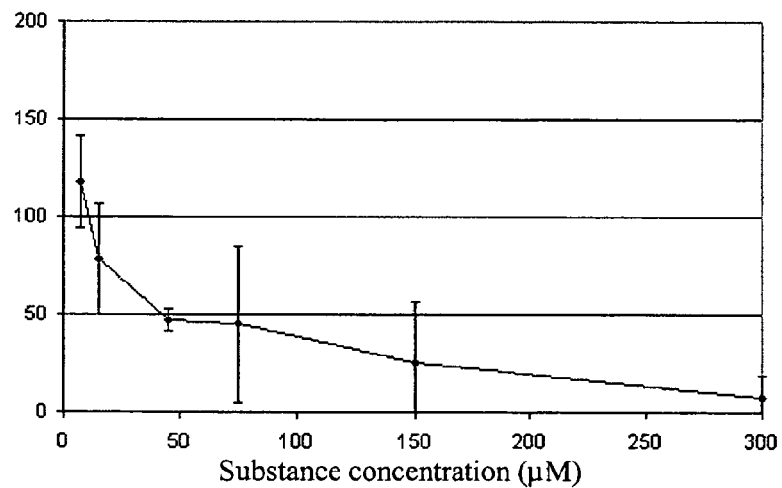

FIG. 10: Inhibition of the aggregation of wild type $A\beta_{1-42}$ (quantification of SDS-insoluble aggregates by means of membrane filter method)

FIG. 11: Inhibition of the aggregation of huntingtin in mammalian cells (quantification of SDS-insoluble aggregates by means of membrane filter method)

Figure 12:
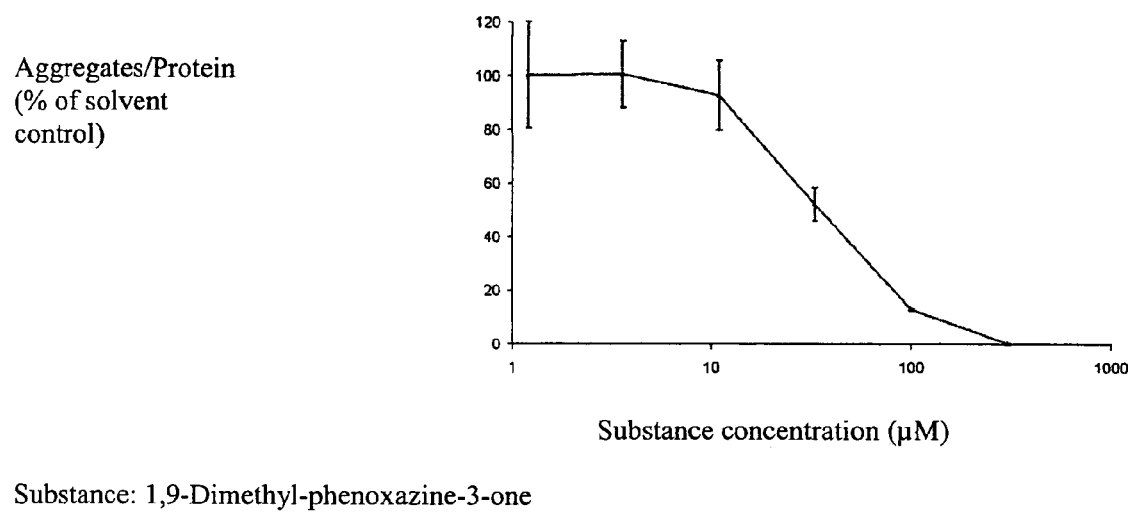

FIG. 12: Inhibition of the aggregation of wild type $A\beta_{1-42}$ (quantification of SDS-insoluble aggregates by means of membrane filter method)

Figure 13:
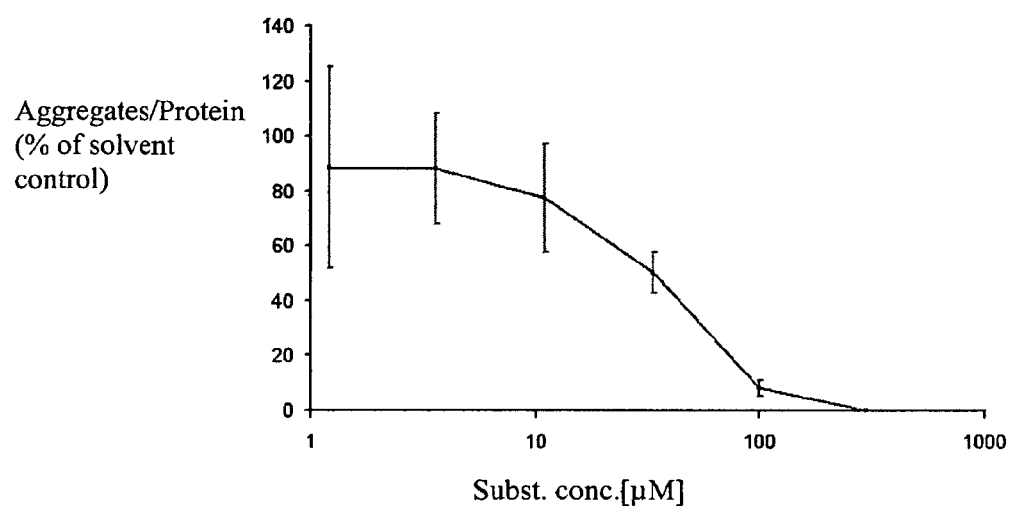

FIG. 13: Inhibition of the aggregation of wild type $A\beta_{1-42}$ (quantification of SDS-insoluble aggregates by means of membrane filter method)

Figure 14:
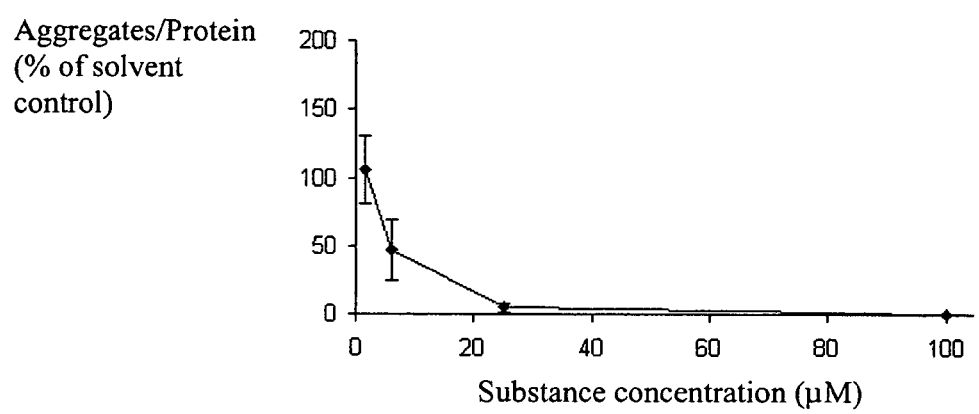

FIG. 14: Inhibition of the aggregation of wild type $A\beta_{1-42}$ (quantification of SDS-insoluble aggregates by means of membrane filter method)

Figure 15:
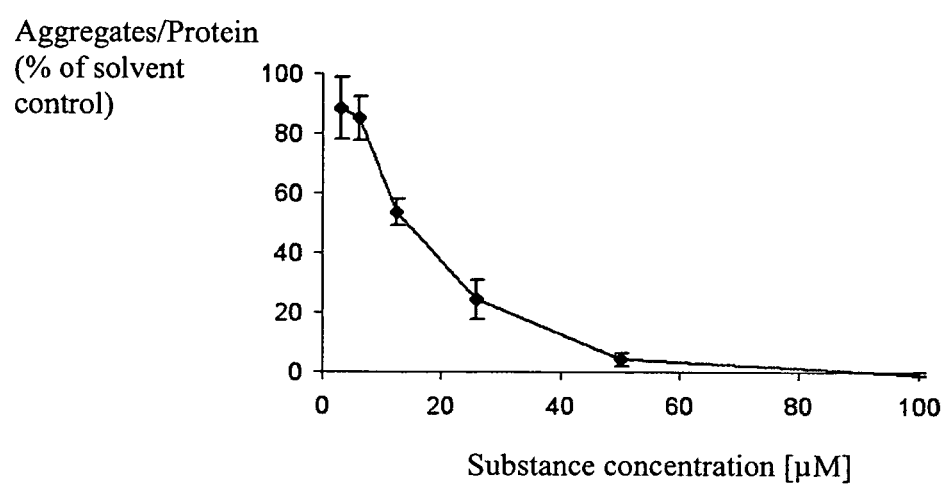

FIG. 15: Inhibition of the aggregation of wild type $A\beta_{1-42}$ (quantification of SDS-insoluble aggregates by means of membrane filter method)

Figure 16:
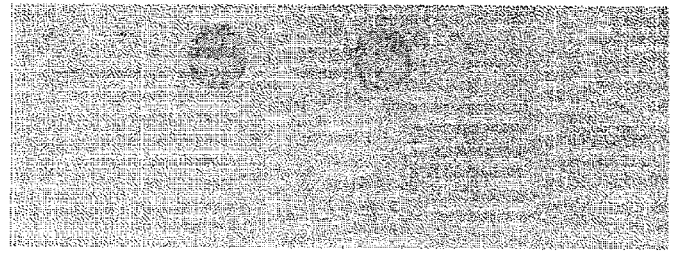
Figure 17:
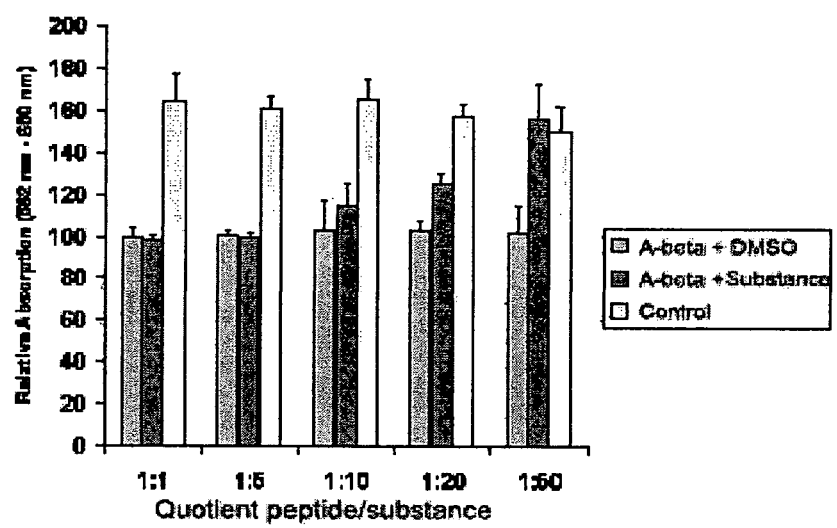

FIG. 16: Binding to amyloid-beta aggregates located on a cellulose acetate membrane FIG. 17: Inhibition of the toxicity of extracellular wild type $A\beta_{1-42}$ by the substances in mammalian cells (neuronally differentiated PC12 cells: Identification by means of MTT test) (quantification of SDS-insoluble aggregates by means of membrane filter method)

Figure 18:
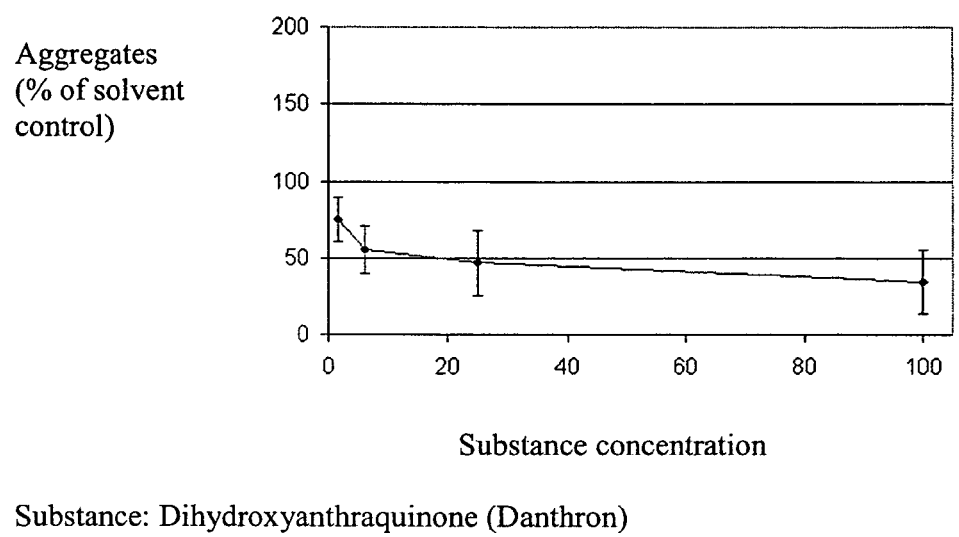

FIG. 18: Inhibition of the aggregation of huntingtin (Exon-1) (quantification of SDS-insoluble aggregates by means of membrane filter method)

Figure 19:
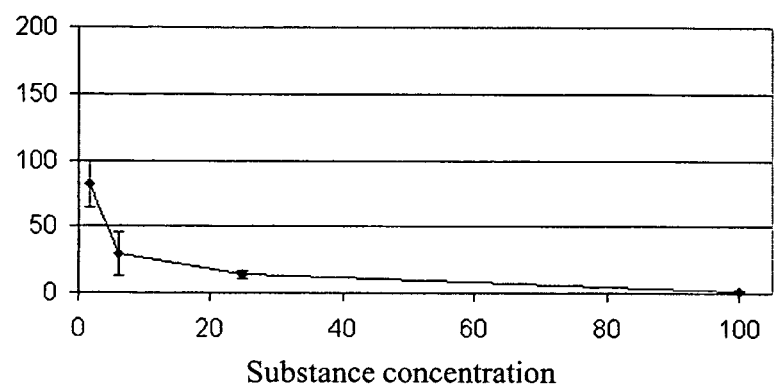

FIG. 19: Inhibition of the aggregation of Huntingtin (Exon-1) (quantification of SDS-insoluble aggregates by means of membrane filter method)

Figure 20:
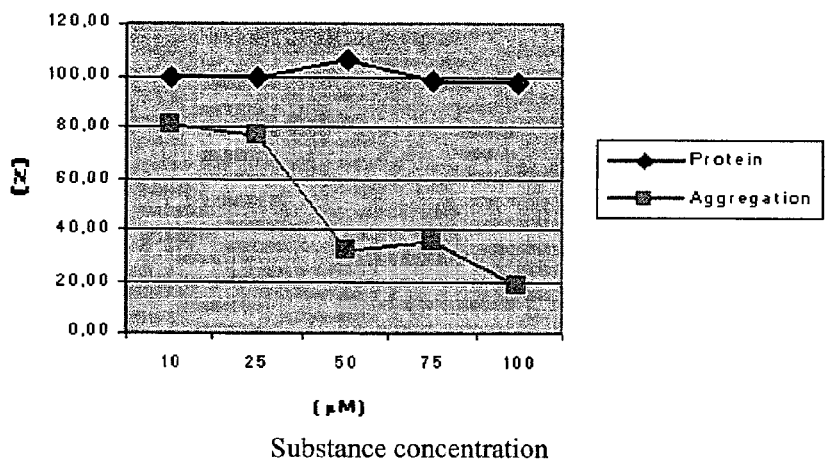

FIG. 20: Inhibition of the aggregation of ataxin-3 in mammalian cells (quantification of SDS-insoluble aggregates by means of membrane filter method)

Figure 21:
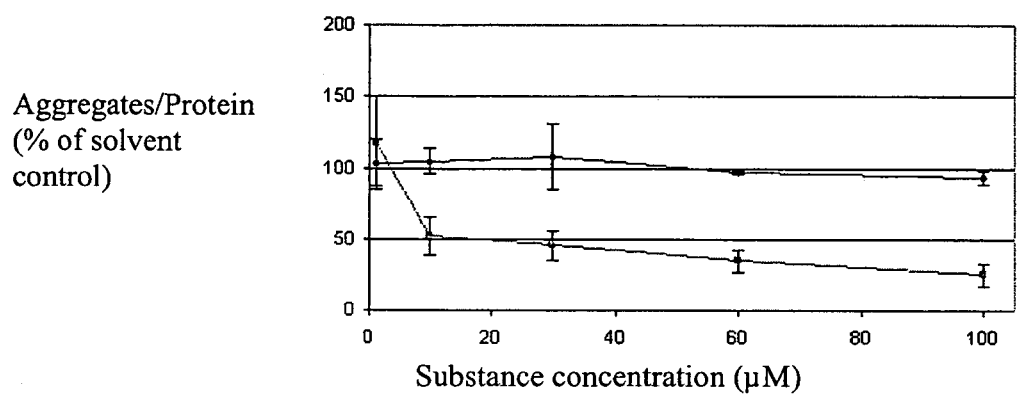

FIG. 21: Inhibition of the aggregation of huntingtin in mammalian cells (quantification of SDS-insoluble aggregates by means of membrane filter method)

Figure 22:
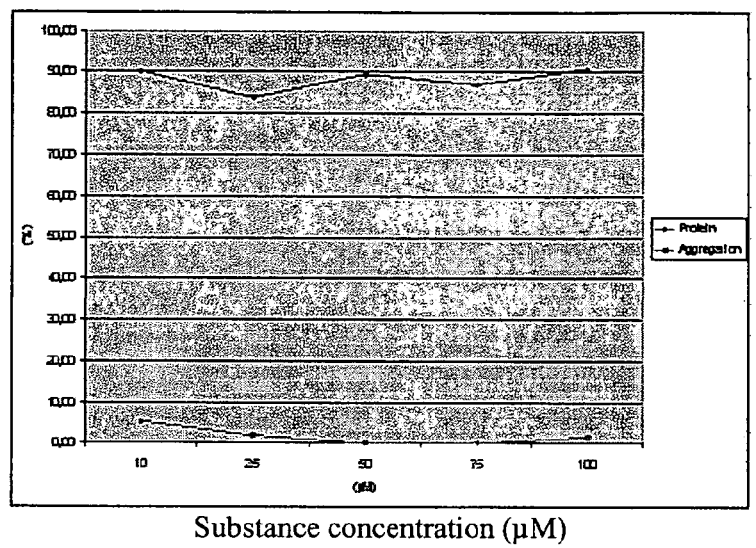

FIG. 22: Inhibition of the aggregation of huntingtin in mammalian cells (quantification of SDS-insoluble aggregates by means of membrane filter method)

Figure 23:
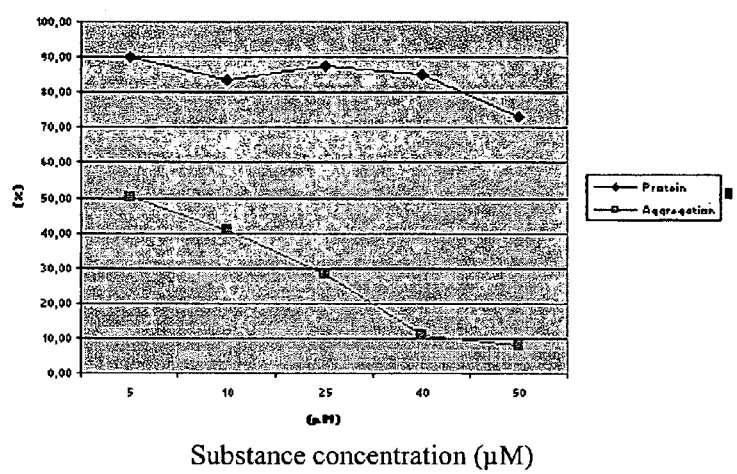

FIG. 23: Inhibition of the aggregation of huntingtin in mammalian cells (quantification of SDS-insoluble aggregates by means of membrane filter method)

Figure 24:
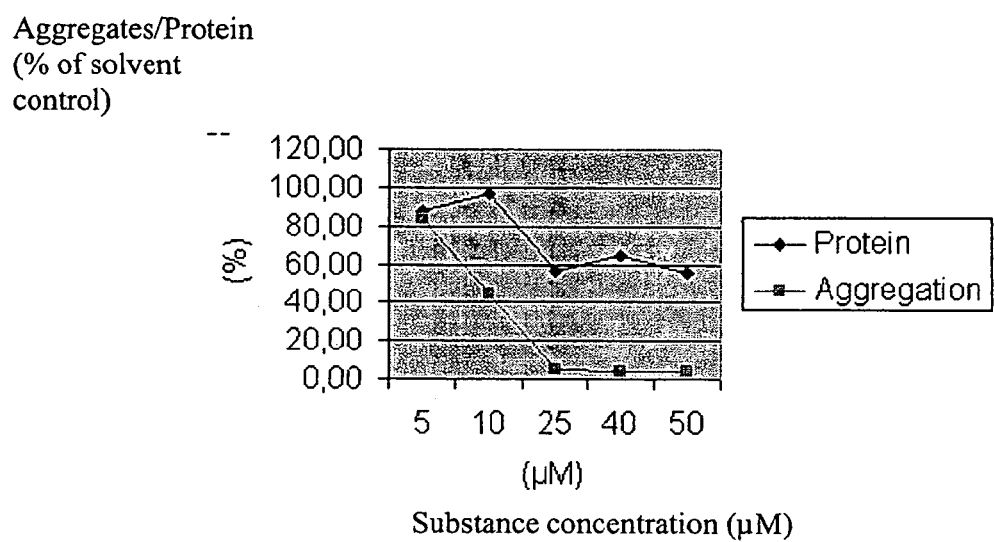

FIG. 24: Inhibition of the aggregation of huntingtin in mammalian cells (quantification of SDS-insoluble aggregates by means of membrane filter method)

Figure 25:
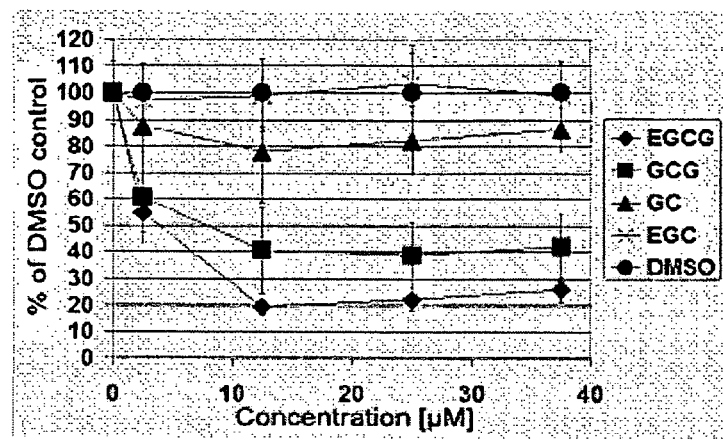

FIG. 25: Inhibition of the aggregation of mutated huntingtin (quantification of SDS-insoluble aggregates by means of membrane filter method)

Figure 26:
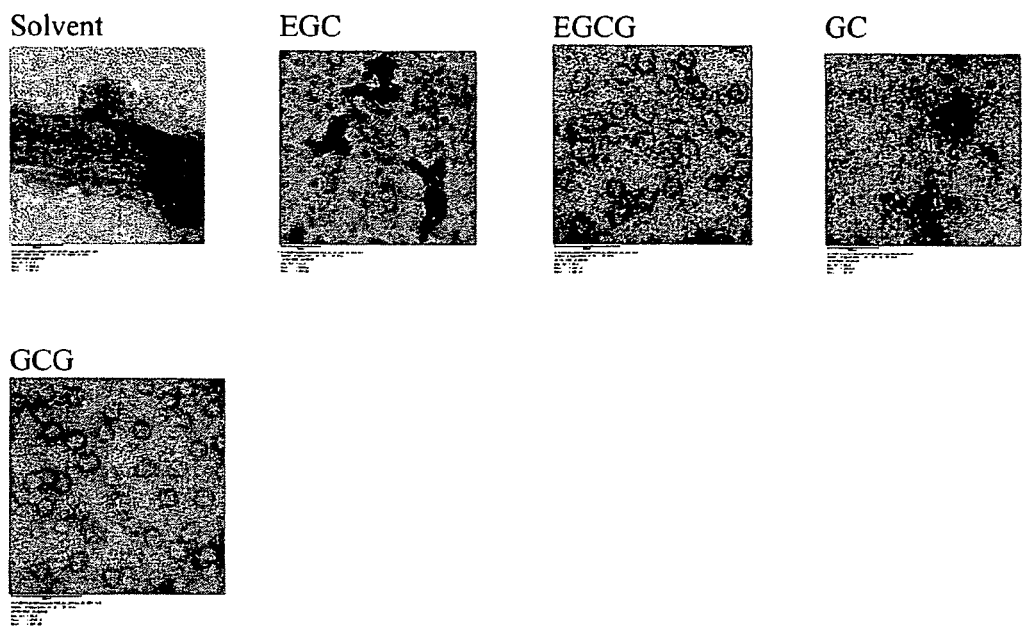

FIG. 26: Inhibition of the aggregation of alpha-synuclein (representation of the amyloid fibrils by means of electron microscopy)

Figure 27:
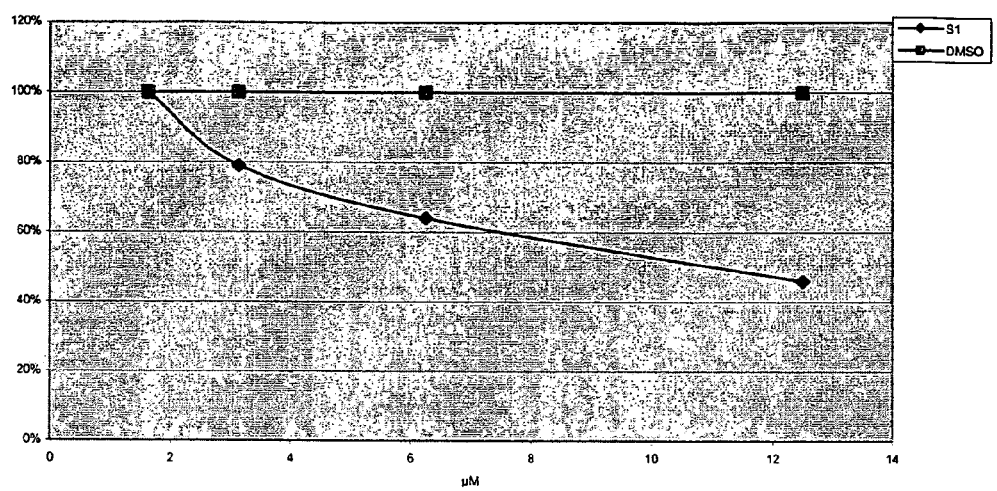

FIG. 27: Inhibition of the aggregation of huntingtin (Exon-1) in mammalian cells (quantification of SDS-insoluble aggregates by means of membrane filter method)

Figure 28:
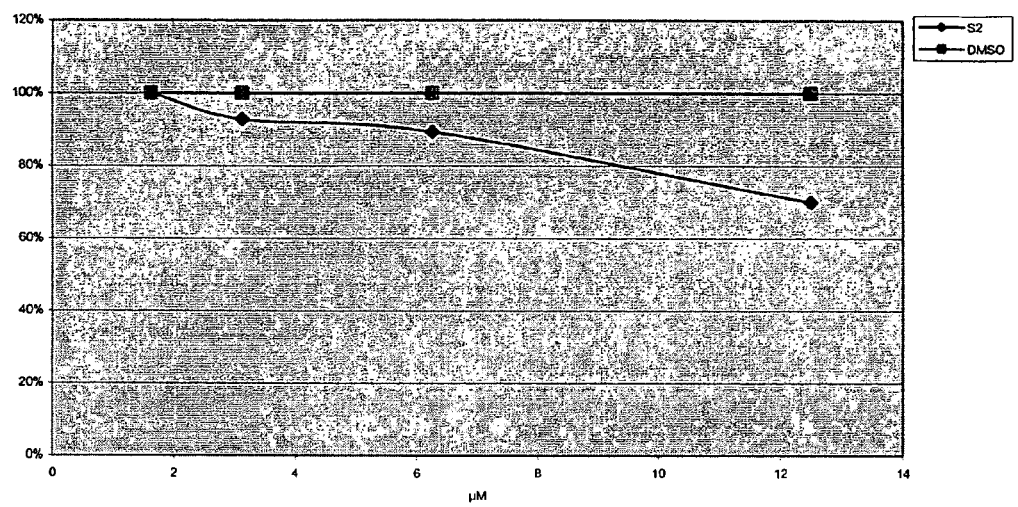

FIG. 28: Inhibition of the aggregation of huntingtin (Exon-1) in mammalian cells (quantification of SDS-insoluble aggregates by means of membrane filter method)

Figure 29:
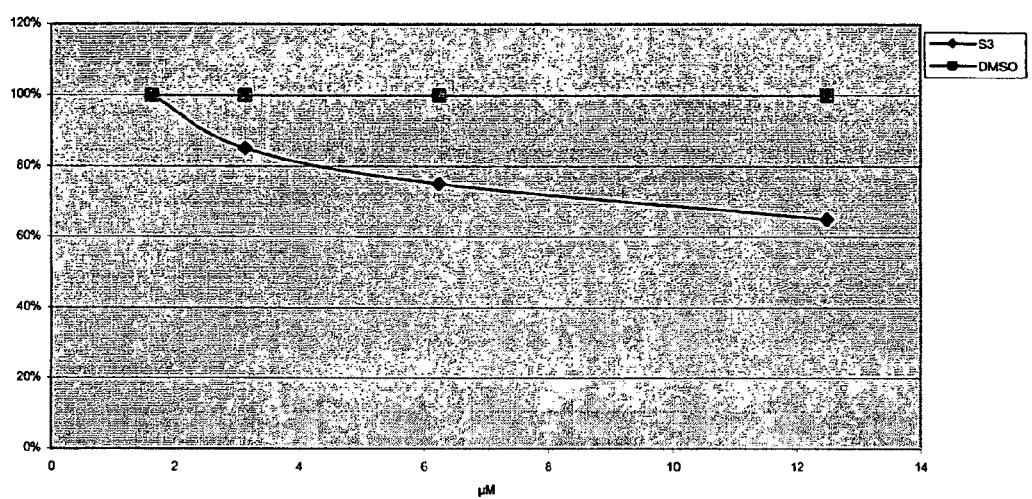

FIG. 29: Inhibition of the aggregation of huntingtin (Exon-1) in mammalian cells (quantification of SDS-insoluble aggregates by means of membrane filter method)

Figure 30:
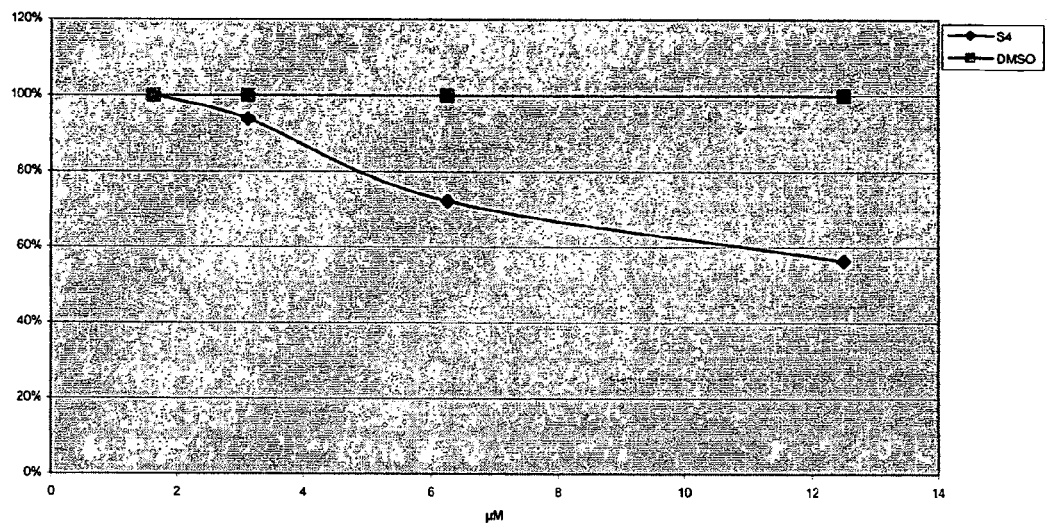

FIG. 30: Inhibition of the aggregation of huntingtin (Exon-1) in mammalian cells (quantification of SDS-insoluble aggregates by means of membrane filter method)

Figure 31:
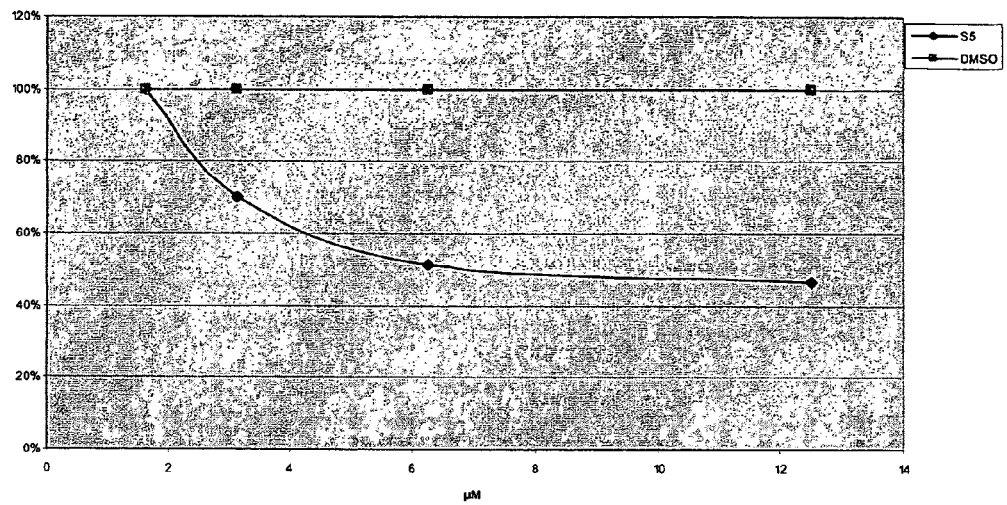

FIG. 31: Inhibition of the aggregation of huntingtin (Exon-1) in mammalian cells (quantification of SDS-insoluble aggregates by means of membrane filter method)

Figure 32:
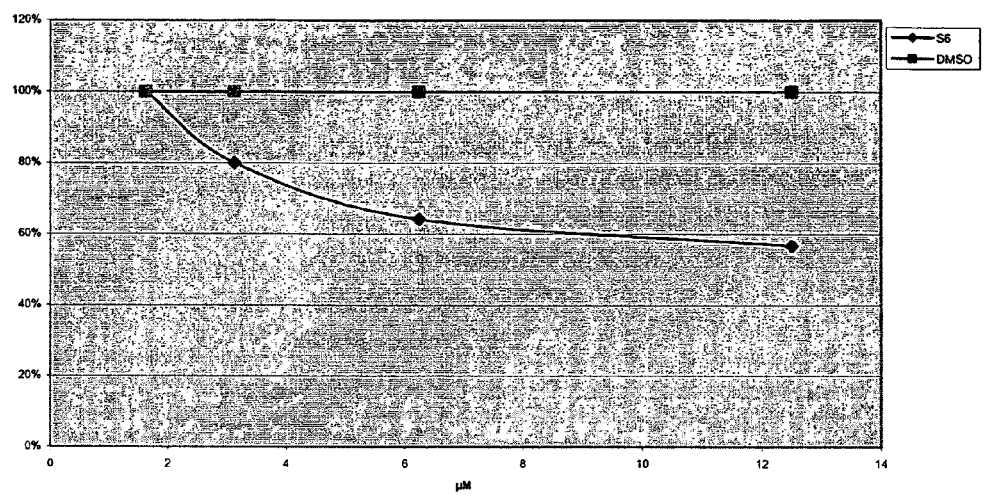

FIG. 32: Inhibition of the aggregation of huntingtin (Exon-1) in mammalian cells (quantification of SDS-insoluble aggregates by means of membrane filter method)

Figure 33:
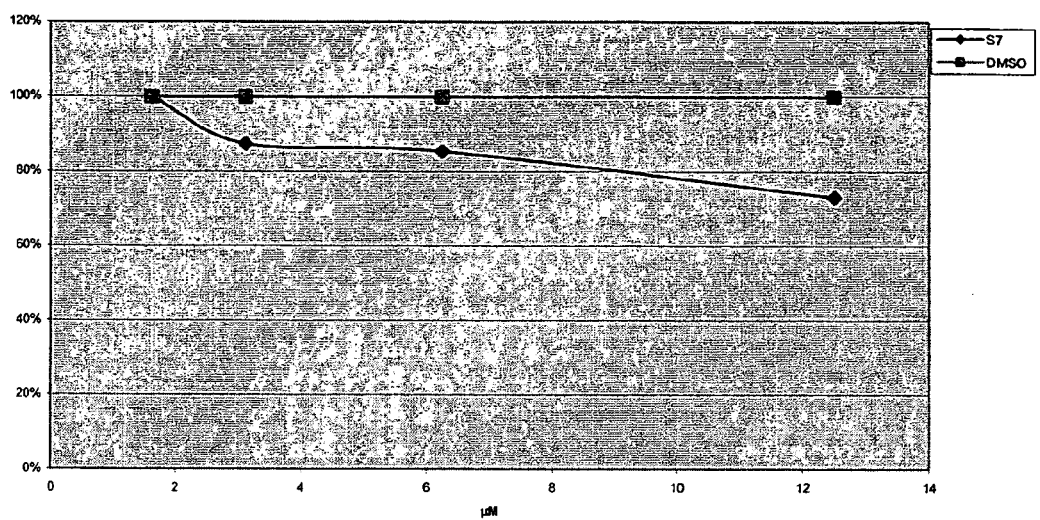

FIG. 33: Inhibition of the aggregation of huntingtin (Exon-1) in mammalian cells (quantification of SDS-insoluble aggregates by means of membrane filter method)

Figure 34:
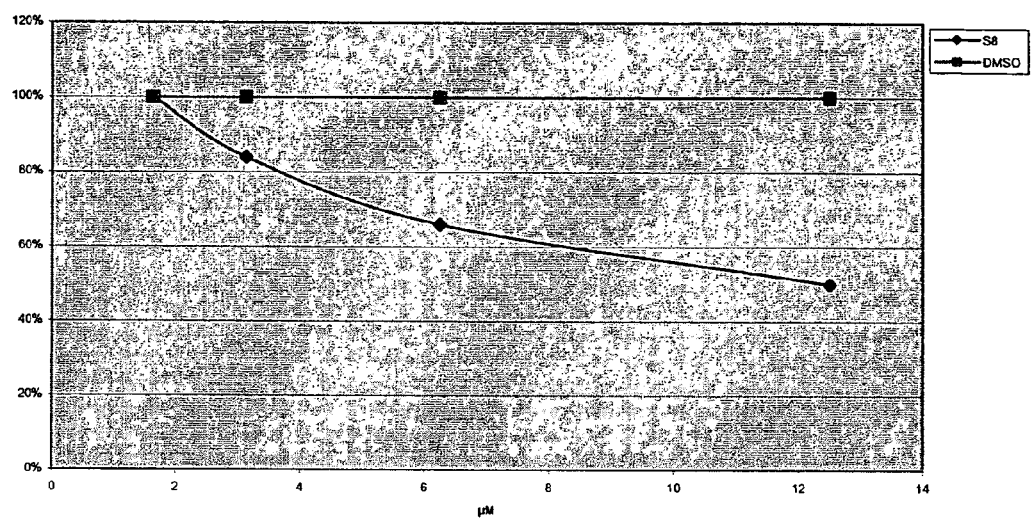

FIG. 34: Inhibition of the aggregation of huntingtin (Exon-1) in mammalian cells (quantification of SDS-insoluble aggregates by means of membrane filter method)

Figure 35:
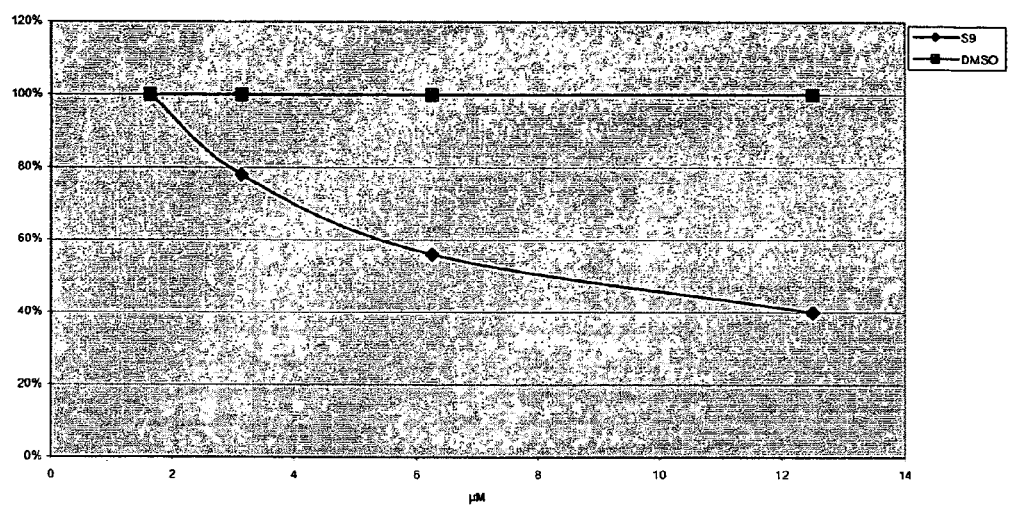

FIG. 35: Inhibition of the aggregation of huntingtin (Exon-1) in mammalian cells (quantification of SDS-insoluble aggregates by means of membrane filter method)

Figure 36:
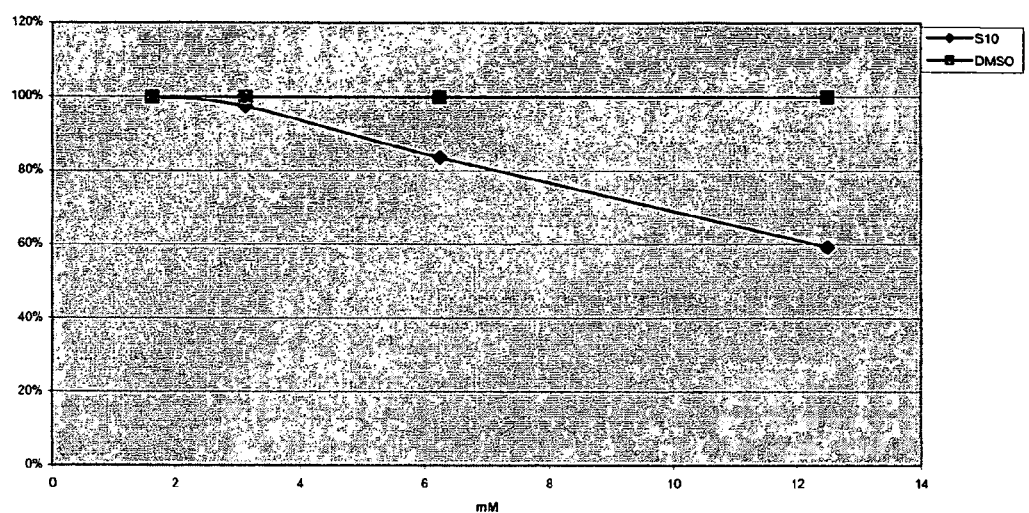

FIG. 36: Inhibition of the aggregation of huntingtin (Exon-1) in mammalian cells (quantification of SDS-insoluble aggregates by means of membrane filter method)

The examples illustrate the invention.

EXAMPLE 1

Material and Methods

For the in vitro experiments, the aggregation inhibiting effect of the compounds on mutant huntingtin was first examined with the help of the GST fusion protein GST-HDQ51. As in the tests described by Heiser et al. (2002), the protein was used for aggregation tests to which either only solvent or solvent and the chemical agent in question was added. Aliquots of these batches were examined by means of the membrane filter test and electron microscopy. By means of one of the two or both methods, an aggregation inhibiting effect of the listed compounds could be verified.

Analogously, the compounds were also examined in aggregation assays with the amyloid β-peptide $A\beta_{1-42}$(E22Q), which is a particularly rapidly aggregating variant of amyloid β, as well as with non-mutated (wild type) $A\beta_{1-42}$. For this purpose, the peptide was incubated at a concentration of 15 µM in a phosphate buffer with a physiological pH value of 7.4 for 42 h at 37° C. and subsequently, aliquots were examined by means of the membrane filter method (Figure) or electron microscopy (Figures) as well. These tests showed that the compounds listed also effectively inhibit the aggregation of the amyloid β-peptide in vitro. Cell viability measurements were carried out in neuronally differentiated PC12 cells to which beta-amyloid and the substances to be tested were added extracellularly in order to examine whether the compounds are able to reduce toxicity caused by amyloid-beta. After 48 h the viability of the cells (approximately corresponds to the number of vital cells) was measured.

The compounds were then tested in several cell culture models of polyglutamine diseases, inter alia Huntington's chorea. For this purpose, COS1 cells were transiently transfected with the plasmid pTL1-CAG51 already described above (Sittler, A., Walter, S., Wedemeyer, N., Hasenbank, R., Scherzinger, E., Eickhoff, H., Bates, G. P., Lehrach, H. and Wanker, E. E. (1998) *Mol Cell* 2, 427-36) and cultivated for 44 h in the presence of solvents or the chemical agents. Subsequently, the amount of aggregate was determined with the help of the membrane filter test as described by Heiser et al. (2002). The compounds described showed an aggregation inhibiting influence in the cell culture model as well (Figures) without having a toxic effect at the concentrations used. The latter could be deduced from the total amount of protein in the cell lysate (FIG. 2B) which was determined with the help of cell extracts.

In addition, it was examined in this cell culture model of Huntington's chorea whether the substances tested substances can cause cell damage by initiating apoptotic processes. For this purpose, the activity of two caspases (caspases-3/-7) was determined fluorometrically after addition of a fluorogenic substrate. The measurements showed that the compounds have positive effects on the activation of caspases (Figures).

For some compounds, a positive effect could be observed in another cell culture model of Huntington's chorea and a cell culture model of spinocerebellar ataxia (type 3). A test system based on the aggregation of an N-terminal ataxin-3 deletion construct (aa 221-360) with 71 glutamines in COS-1 cells was developed to isolate substances inhibiting the ataxin-3 aggregation. The cells were transiently transfected with the ataxin-3 expression construct and incubated in plates with 96 perforations with the added substance at 37° C. in an incubator. After 40 h the cells were harvested and lysated. The lysates were denatured in the presence of 2% SDS and analyzed using the filtration method.

In order to detect the inhibiting effect of the substances on the aggregation of alpha-synuclein, the formation of amyloid fibrils was observed with the help of electron microscopy. For this purpose, the wild type protein or a mutant (A53T) was used.

EXAMPLE 2

Formula I-1

Inhibition of the aggregation of wild type $A\beta_{1-42}$ (quantification of SDS-insoluble aggregates by means of membrane filter method) by 2-(1H-imidazole-4-yl)-1H-perimidine, 1-ethyl-1H-perimidine, 2-pyridine-3-yl-1H-perimidine and 2-p-tolyl-1H-perimidine (see FIG. 3).

Inhibition of the aggregation of wild type $A\beta_{1-42}$ (quantification of SDS-insoluble aggregates by means of membrane filter method) by 1,2-dimethyl-1H-perimidine, 4-(1H-perimidine-2-yl)-benzonitrile, 1H,3H-perimidine-2-thione and 3-(1H-perimidine-2-yl)-phenylamine (see FIG. 4).

Inhibition of toxicity of extracellular wild type $A\beta_{1-42}$ by 3-(1H-perimidine-2-yl)-phenylamine in mammalian cells (neuronally differentiated PC12 cells): Identification by means of MTT test (quantification of SDS-insoluble aggregates by means of membrane filter method) (see FIG. 5).

Inhibition of the aggregation of huntingtin (Exon-1) (quantification of SDS-insoluble aggregates by means of membrane filter method) by (1-methyl-1H-perimidine-2-yl)-methanol (see FIG. 6).

Inhibition of the amyloid fibril formation of huntingtin (Exon-1) (electron microscopy) by 2-pyridine-4-yl-2,3-dihydro-1H-perimidine (see FIG. 7).

EXAMPLE 3

Formula I-2

Inhibition of the aggregation of ataxin-3 in mammalian cells (quantification of SDS-insoluble aggregates by means of membrane filter method) by 8-fluoro-1,2-dimethyl-4,5-dihydro-pyrrolo[3,2,1-ij]quinoline-6-one (see FIG. 8).

Inhibition of the aggregation of huntingtin in mammalian cells (quantification of SDS-insoluble aggregates by means of membrane filter method) by 8-fluoro-1,2-dimethyl-4,5-dihydro-pyrrolo[3,2,1-ij]quinoline-6-one (see FIG. 9).

EXAMPLE 4

Formula I-3

Inhibition of the aggregation of wild type $A\beta_{1-42}$ (quantification of SDS-insoluble aggregates by means of membrane filter method) by 2-furan-2-yl-2,3,4,9-tetrahydro-1H-indenol[2,3-c]pyridine-3-carboxylic acid methyl ester (see FIG. 10).

EXAMPLE 5

Formula I-4

Inhibition of the aggregation of huntingtin in mammalian cells (quantification of SDS-insoluble aggregates by means of membrane filter method) by 3H-phenoxazine, phenoxazin-3-one, 7-amino-1,9-dimethyl-phenoxazine-3-one, beta-amino-orcein, alpha-amino-orcein and alpha-hydroxy-orcein (see FIG. 11).

Inhibition of the aggregation of wild type $A\beta_{1-42}$ (quantification of SDS-insoluble aggregates by means of membrane filter method) by 1,9-dimethyl-phenoxazine-3-one (see FIG. 12).

Inhibition of the aggregation of wild type $A\beta_{1-42}$ (quantification of SDS-insoluble aggregates by means of membrane filter method) by 7-hydroxy-1,9-dimethyl-phenoxazine-3-one (see FIG. 13).

Inhibition of the aggregation of wild type $A\beta_{1-42}$ (quantification of SDS-insoluble aggregates by means of membrane filter method) by alpha-amino-orcein (see FIG. 14).

Inhibition of the aggregation of wild type $A\beta_{1-42}$ (quantification of SDS-insoluble aggregates by means of membrane filter method) by beta-hydroxy-orcein (see FIG. 15).

The following—colored—substances bind directly to amyloid-beta fibrils (see FIG. 16: amyloid-beta aggregates located on a cellulose acetate membrane): Alpha-amino-orcein, alpha-hydroxy-orcein, alpha-amino-orceimine, beta-hydroxy-orcein, beta-amino-orcein, beta-amino-orceimine, gamma-amino-orcein, gamma-hydroxy-orcein, gamma-amino-orceimine, phenoxazine, phenoxazone (see FIG. 16).

Inhibition of the toxicity of extracellular wild type $A\beta_{1-42}$ by the substances in mammalian cells (neuronally differentiated PC12 cells: Identification by means of MTT test) (quantification of SDS-insoluble aggregates by means of membrane filter method) by alpha-amino-orcein (see FIG. 17).

EXAMPLE 6

In this example, the compound 7-amino-8-(2,4-dihydroxy-6-methyl-phenyl)-1,9-dimethyl-phenoxazine-3-one (also referred to as #6 in FIG. 1) and its effects on the aggregation of the huntingtin protein and the amyloid β-peptide in vitro as well as its effects in the cell culture model of Huntington's chorea are described.

For the in vitro experiments, the aggregation inhibiting effect of 7-amino-8-(2,4-dihydroxy-6-methyl-phenyl)-1,9-dimethyl-phenoxazine-3-one on mutant huntingtin was first examined with the help of the GST fusion protein GST-HDQ51. As in the tests described by Heiser et al. (2002), the protein was used for aggregation tests to which either only solvent or solvent and 7-amino-8-(2,4-dihydroxy-6-methyl-phenyl)-1,9-dimethyl-phenoxazine-3-one was added. Aliquots of these batches were examined by means of the membrane filter test (FIG. 1B) and electron microscopy (FIGS. 1E and 1F). By means of both methods, an aggregation inhibiting effect of 7-amino-8-(2,4-dihydroxy-6-methyl-phenyl)-1,9-dimethyl-phenoxazine-3-one could be verified.

Analogously, the compound was also examined in aggregation assays with the amyloid β-peptide Aβ1-42[E22Q] which is a particularly rapidly aggregating variant of amyloid β. For this purpose, the peptide was incubated at a concentration of 15 μM in a phosphate buffer with a physiological pH value of 7.4 for 42 h at 37° C. and subsequently, aliquots were examined by means of the membrane filter method (FIG. 1A) or electron microscopy (FIGS. 1C and 1D) as well. These tests showed that 7-amino-8-(2,4-dihydroxy-6-methyl-phenyl)-1,9-dimethyl-phenoxazine-3-one also effectively inhibits the aggregation of the amyloid β-peptide in vitro.

7-Amino-8-(2,4-dihydroxy-6-methyl-phenyl)-1,9-dimethyl-phenoxazine-3-one was then tested in a cell culture model of Huntington's chorea. For this purpose, COS1 cells were transiently transfected with the plasmid pTL1-CAG51 already described above (Sittler, A., Walter, S., Wedemeyer, N., Hasenbank, R., Scherzinger, E., Eickhoff, H., Bates, G. P., Lehrach, H. and Wanker, E. E. (1998) *Mol Cell* 2, 427-36) and cultivated for 40-44 h in the presence of solvents or 7-amino-8-(2,4-dihydroxy-6-methyl-phenyl)-1,9-dimethyl-phenoxazine-3-one. Subsequently, the amount of aggregate was determined with the help of the membrane filter test as described by Heiser et al. (2002). 7-Amino-8-(2,4-dihydroxy-6-methyl-phenyl)-1,9-dimethyl-phenoxazine-3-one showed an aggregation inhibiting influence in the cell culture model as well (FIG. 2A) without having a toxic effect. The latter could be deduced from the total amount of protein (FIG. 2B) which was determined with the help of cell extracts.

In addition, it was examined in this cell culture model of Huntington's chorea whether 7-amino-8-(2,4-dihydroxy-6-methyl-phenyl)-1,9-dimethyl-phenoxazine-3-one can cause cell damage by initiating apoptotic processes. For this purpose, the activity of two caspases (caspases 3 and 7) was determined fluorometrically after addition of a fluorogenic substrate. The measurements showed that the cultivation in the presence of 7-amino-8-(2,4-dihydroxy-6-methyl-phenyl)-1,9-dimethyl-phenoxazine-3-one not only did not cause cell damage but, to the contrary, had an especially favorable effect on the cells since their caspase activity was reduced (FIG. 2C).

This observation is in line with the observation that in the presence of 7-amino-8-(2,4-dihydroxy-6-methyl-phenyl)-1,9-dimethyl-phenoxazine-3-one the total protein content was increased by almost 20% which can be interpreted as a sign for increased cell growth.

The experiments presented here using 7-amino-8-(2,4-dihydroxy-6-methyl-phenyl)-1,9-dimethyl-phenoxazine-3-one as an example were also carried out analogously with the other compounds. In the case of some compounds, a positive effect could be observed in another cell culture model of Huntington's chorea and in a cell culture model of spinocerebellar ataxia (type 3).

The experiments presented here using 7-amino-8-(2,4-dihydroxy-6-methyl-phenyl)-1,9-dimethyl-phenoxazine-3-one as an example were also carried out analogously with the other compounds (see examples above and below). In the case of some compounds, a positive effect could be observed in another cell culture model of Huntington's chorea and in a cell culture model of spinocerebellar ataxia (type 3).

EXAMPLE 7

Formula I-5

Inhibition of the aggregation of huntingtin (Exon-1) (quantification of SDS-insoluble aggregates by means of membrane filter method) by dihydroxyanthraquinone (danthron) (see FIG. 18).

EXAMPLE 8

Formula I-9

Inhibition of the aggregation of huntingtin (Exon-1) (quantification of SDS-insoluble aggregates by means of membrane filter method) by chrysarobin (see FIG. 19).

EXAMPLE 9

Formula II-2

The compounds were additionally tested in a stably transfected PC12 cell line. This cell line was transfected with an ecdysone-inducible plasmid whose N-terminal codes for huntingtin-Exon-1 marked with GFP with 103 glutamines (Htt103Q-EGFP). The Htt103Q-EGFP expression was induced with muristerone and the cells were subsequently cultivated for 44 h in the presence of solvents or the chemical agents. Subsequently, the amount of aggregate was determined with the help of the membrane filter test as described by Heiser et al. (2002). Furthermore, the amount of aggregate was determined with the help of a fluorescence measurement (data not shown). The compounds described showed an aggregation inhibiting influence in the cell culture model as well (Figures) without having a toxic effect at the concentrations used. The latter could be deduced from the total amount of protein in the cell lysate (FIG. 2B) which was determined with the help of cell extracts.

Inhibition of the aggregation of huntingtin (Exon-1) in mammalian cells (quantification of SDS-insoluble aggregates by means of membrane filter method) by 2-amino-7-oxo-6,7-dihydro-thiazolo[4,5-f]quinoline-8-carbonitrile (see FIG. 27), 2-(3-dimethylamino-propylamino)-7-oxo-6,7-dihydro-thiazolo[4,5-f]quinoline-8-carbonitrile (see FIG. 28), N-(8-cyano-7-oxo-6,7-dihydro-thiazolo[4,5-f]quinoline-2-yl)-N-(3-dimethylamino-propyl)-formamide (see FIG. 29), N-(8-cyano-7-oxo-6,7-dihydro-thiazolo[4,5-f]quinoline-2-yl)-acetamide (see FIG. 30), N-(8-cyano-7-oxo-6,7-dihydro-thiazolo[4,5-f]quinoline-2-yl)-N-(2-dimethylamino-ethyl)-formamide (see FIG. 31), N-(8-cyano-7-oxo-6,7-dihydro-thiazolo[4,5-f]quinoline-2-yl)-N-(2-dimethylamino-ethyl)-acetamide (see FIG. 32), 7-oxo-2-(2-piperidine-1-yl-ethylamino)-6,7-dihydro-thiazolo[4,5-f]quinoline-8-carbonitrile (see FIG. 33), 2-[4-(3-hydroxy-propyl)-piperazine-1-yl]-7-oxo-6,7-dihydro-thiazolo[4,5-f]quinoline-8-carbonitrile (see FIG. 34), 2-[benzyl-(2-dimethylamino-ethyl)-amino]-7-oxo-6,7-dihydro-thiazolo[4,5-f]quinoline-8-carbonitrile (see FIG. 35) and 2-[(2-diethylamino-ethyl)-ethyl-amino]-7-oxo-6,7-dihydro-thiazolo[4,5-f]quinoline-8-carbonitrile (see FIG. 36).

EXAMPLE 10

Formula III-6

Inhibition of the aggregation of ataxin-3 in mammalian cells (quantification of SDS-insoluble aggregates by means of membrane filter method) by thiophene-2-yl-acetic acid 4-(4-acetyl-piperazine-1-yl)-phenyl ester (see FIG. 20).

Inhibition of the aggregation of huntingtin in mammalian cells (quantification of SDS-insoluble aggregates by means of membrane filter method) by thiophene-2-yl-acetic acid 4-(4-acetyl-piperazine-1-yl)-phenyl ester (see FIG. 21).

EXAMPLE 11

Formula IV-1

Inhibition of the aggregation of huntingtin in mammalian cells (quantification of SDS-insoluble aggregates by means of membrane filter method) by 5-[4-(thiazole-2-ylcarbamoyl)-phenyl]-furan-2-carboxylic acid thiazole-2-ylamide (see FIG. 22).

EXAMPLE 12

Formula IV-2

Inhibition of the aggregation of huntingtin in mammalian cells (quantification of SDS-insoluble aggregates by means of membrane filter method) by 4-methyl-2-[3-(3-phenyl-[1,2,4]thiadiazole-5-yl)-ureido]-pentanoic acid ethyl ester (see FIG. 23).

Inhibition of the aggregation of huntingtin in mammalian cells (quantification of SDS-insoluble aggregates by means of membrane filter method) by 4-methyl-2-(3-phenyl-[1,2,4]thiadiazole-5-yl)-pentanoic acid ethyl ester (see FIG. 24).

EXAMPLE 13

Formulas V-1 to V-4

Inhibition of the aggregation of mutated huntingtin (quantification of SDS-insoluble aggregates by means of membrane filter method) by EGCG (Epigallocatechin gallate), GCG (Gallocatechin gallate), GC (Gallocatechin) and EGC (Epigallocatechin) (see FIG. 25).

Inhibition of the aggregation of alpha-synuclein (representation of the amyloid fibrils by means of electron microscopy) by EGCG (Epigallocatechin gallate), GCG (Gallocatechin gallate), GC (Gallocatechin) and EGC (Epigallocatechin) (see FIG. 26).

The invention claimed is:
1. Pharmaceutical or diagnostic composition comprising active substance of formula VI-2

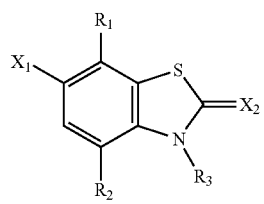

Formula VI-2 wherein $R_1$ and $R_3$ are selected from
(i) H, OH, $NH_2$ or a halogen atom;
(ii) single- or multi-branched or straight-chain alkyl or heteroalkyl groups with one or two rings and up to 10 carbon atoms;

(iii) cyclic alkyl or heteroalkyl groups with 1 or 2 rings or aryl or heteroaryl groups with up to 10 carbon atoms each; and wherein $R_2$ is selected from (i) OH, $NH_2$ or a halogen atom;

(ii) single- or multi-branched or straight-chain alkyl or heteroalkyl groups with one or two rings and up to 10 carbon atoms;

(iii) cyclic alkyl or heteroalkyl groups with 1 or 2 rings or aryl or heteroaryl groups with up to 10 carbon atoms each; and wherein for the structure of Formula VI-2, the alkyl, heteroalkyl, aryl or heteroaryl groups comprise 0, 1, 2, 3 or 4 substituents, each selected from a group consisting of Cl, Fl, Br and I, $X_1$ is selected from the group consisting of H, F, I, Br, Cl, OH, OA, SH, SA, $NH_2$, $NHA_1$, $NA_1A_2$, and A; wherein A, $A_1$, and $A_2$ are independently a branched, straight-chain or cyclic alkyl group with 1, 2, 3, 4, 5, or 6 carbon atoms, an aromatic group with 1, 2, 3, 4, 5, 6, or 7 carbon atoms or combinations thereof, wherein individual carbon atoms are optionally replaced with 1, 2, 3, or 4 S, N, or O atoms, and $X_2$ is O or S.

2. The pharmaceutical or diagnostic composition according to claim 1, wherein the halogen atoms are selected from the group consisting of I, Cl, Br and F.

3. The pharmaceutical or diagnostic composition according to claim 1, wherein the alkyl, heteroalkyl, aryl or heteroaryl groups comprise 1, 2, 3 or 4 heteroatoms each.

4. The pharmaceutical or diagnostic composition according to claim 3, wherein the heteroatoms are selected from a group consisting of N, O, and S.

5. The pharmaceutical or diagnostic composition according to claim 1, wherein the alkyl, heteroalkyl, aryl or heteroaryl groups comprise 1, 2, 3 or 4 substituents each.

6. The pharmaceutical or diagnostic composition according to claim 5, wherein the substituents are selected from a group consisting of Cl, F, Br and I.

7. The pharmaceutical or diagnostic composition according to claim 1, wherein $R_1$ and $R_2$, $R_2$ and $R_3$, are bridged via further atoms.

8. The diagnostic composition according to claim 1, wherein the active substance is labeled.

9. The diagnostic composition according to claim 8, wherein the labeled active substance is radioactive-labeled.

10. The pharmaceutical or diagnostic composition according to claim 1, wherein the pharmaceutical or diagnostic composition furthermore comprises one or more pharmaceutically acceptable carriers, diluents or excipients.

11. A method for the treatment or diagnosis of a polyglutamine disease comprising administering a pharmaceutical or a diagnostic composition according to claim 1 to a subject.

12. The method according to claim 11, wherein the subject is a human being.

13. The method according to claim 11, wherein the polyglutamine disease comprises Huntington's chorea, spinocerebellar ataxias of types 1, 2, 3, 6, 7 and 17, dentatorubral pallidoluysian atrophy or spinobulbar muscular atrophy (Kennedy syndrome).

* * * * *